US010577574B2

(12) United States Patent
Wikswo et al.

(10) Patent No.: US 10,577,574 B2
(45) Date of Patent: Mar. 3, 2020

(54) INTERCONNECTIONS OF MULTIPLE PERFUSED ENGINEERED TISSUE CONSTRUCTS AND MICROBIOREACTORS, MULTI-MICROFORMULATORS AND APPLICATIONS OF THE SAME

(71) Applicant: VANDERBILT UNIVERSITY, Nashville, TN (US)

(72) Inventors: John P. Wikswo, Brentwood, TN (US); Frank E. Block, III, Nashville, TN (US); Philip C. Samson, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 16/012,900

(22) Filed: Jun. 20, 2018

(65) Prior Publication Data

US 2018/0298319 A1    Oct. 18, 2018

Related U.S. Application Data

(60) Division of application No. 15/191,092, filed on Jun. 23, 2016, now Pat. No. 10,023,832, which is a
(Continued)

(51) Int. Cl.
*C12M 3/06* (2006.01)
*C12M 3/00* (2006.01)
(Continued)

(52) U.S. Cl.
CPC ........... *C12M 23/16* (2013.01); *A01N 1/0247* (2013.01); *B01L 3/5027* (2013.01); *C12M 23/12* (2013.01);
(Continued)

(58) Field of Classification Search
CPC ...... C12M 23/16; C12M 23/12; C12M 23/58; C12M 23/44; C12M 41/48; C12M 29/00;
(Continued)

(56) References Cited

U.S. PATENT DOCUMENTS

2004/0164010 A1* 8/2004 Bayer ................. B01F 13/0059
    210/141
2007/0039866 A1* 2/2007 Schroeder ........ G01N 27/44769
    210/265
(Continued)

FOREIGN PATENT DOCUMENTS

CN    102257124 A    11/2011
EP      2730645 A2    5/2014
(Continued)

OTHER PUBLICATIONS

European Patent Office, "The Extended European Search Report for EP Application No. 18167976.2", The Hague, dated Nov. 16, 2018.
(Continued)

*Primary Examiner* — Michael L Hobbs
(74) *Attorney, Agent, or Firm* — Locke Lord LLP; Tim Tingkang Xia, Esq.

(57) ABSTRACT

The invention relates to a system of fluidic valves and pumps and associated fluidic channels integratable into a bio-object microfluidics module. The module includes input and output buses; upstream and downstream interconnection bus control valves (CVs) coupled to the input and output buses, respectively. It may include arterial, venous, wash and waste bus lines, each connecting between the upstream and downstream interconnection bus CVs. It may also include an input CV connecting to the arterial bus line, upstream interconnection bus CV, bio-object and inlets, and an output CV connecting to the bio-object, input CV, downstream interconnection bus CV and outlets; and a pump connecting between the input CV and bio-object. The system of fluidic
(Continued)

valves and pumps can be arranged to provide MicroFormulator functionality enabling precise mixtures of drugs, chemicals, or biochemicals to be delivered in a time-dependent fashion to biological entities housed in individual wells or chambers.

17 Claims, 49 Drawing Sheets

Related U.S. Application Data continuation-in-part of application No. 13/877,925, filed as application No. PCT/US2011/055432 on Jul. 16, 2013, now abandoned, said application No. 15/191,092 is a continuation-in-part of application No. 14/363,074, filed as application No. PCT/US2012/068771 on Jun. 5, 2014, now Pat. No. 10,078,075, said application No. 15/191,092 is a continuation-in-part of application No. 14/646,300, filed as application No. PCT/US2013/071026 on May 20, 2015, now Pat. No. 9,874,285, said application No. 15/191,092 is a continuation-in-part of application No. 14/651,174, filed as application No. PCT/US2013/071324 on Jun. 10, 2015, now Pat. No. 9,618,129.

(60) Provisional application No. 62/183,571, filed on Jun. 23, 2015, provisional application No. 62/193,029, filed on Jul. 15, 2015, provisional application No. 62/276,047, filed on Jan. 7, 2016, provisional application No. 62/295,306, filed on Feb. 15, 2016, provisional application No. 61/390,982, filed on Oct. 7, 2010, provisional application No. 61/569,145, filed on Dec. 9, 2011, provisional application No. 61/697,204, filed on Sep. 5, 2012, provisional application No. 61/717,441, filed on Oct. 23, 2012, provisional application No. 61/729,149, filed on Nov. 21, 2012, provisional application No. 61/808,455, filed on Apr. 4, 2013, provisional application No. 61/822,081, filed on May 10, 2013.

(51) Int. Cl.
| | | |
|---|---|---|
| *A01N 1/02* | (2006.01) | |
| *C12M 1/00* | (2006.01) | |
| *C12M 1/32* | (2006.01) | |
| *C12M 1/36* | (2006.01) | |
| *F04B 43/00* | (2006.01) | |
| *B01L 3/00* | (2006.01) | |

(52) U.S. Cl.
CPC ............ *C12M 23/44* (2013.01); *C12M 23/58* (2013.01); *C12M 29/00* (2013.01); *C12M 41/48* (2013.01); *F04B 43/0045* (2013.01); *B01L 3/502715* (2013.01)

(58) Field of Classification Search
CPC .............. B01L 3/5027; B01L 3/502715; F04B 43/0045; A01N 1/0247; A01N 1/02; A01N 1/0205; A01N 1/0273; A01N 1/0263; A01N 1/021
See application file for complete search history.

(56) References Cited

U.S. PATENT DOCUMENTS

| | | | |
|---|---|---|---|
| 2011/0002812 A1* | 1/2011 | Asogawa | B01L 3/502715 422/68.1 |
| 2011/0212453 A1* | 9/2011 | Agarwal | G01N 35/00029 435/6.12 |
| 2012/0085644 A1* | 4/2012 | Renzi | B01L 3/502715 204/450 |
| 2012/0264134 A1 | 10/2012 | Ionescu-Zanetti et al. | |

FOREIGN PATENT DOCUMENTS

| | | |
|---|---|---|
| WO | 2003027223 A2 | 4/2003 |
| WO | 2013086329 A1 | 6/2013 |
| WO | 2013086505 A1 | 6/2013 |
| WO | 2014081840 A1 | 5/2014 |
| WO | 2015006751 A1 | 1/2015 |

OTHER PUBLICATIONS

Chinese Patent Office, "1st Chinese Office Action and Search Report for CN Application No. 201710014601.1", China, dated Dec. 12, 2018.

\* cited by examiner

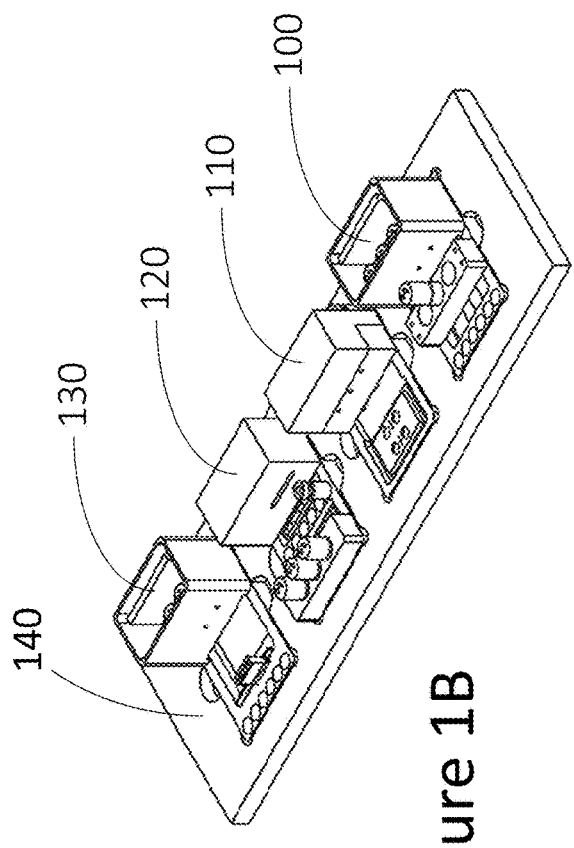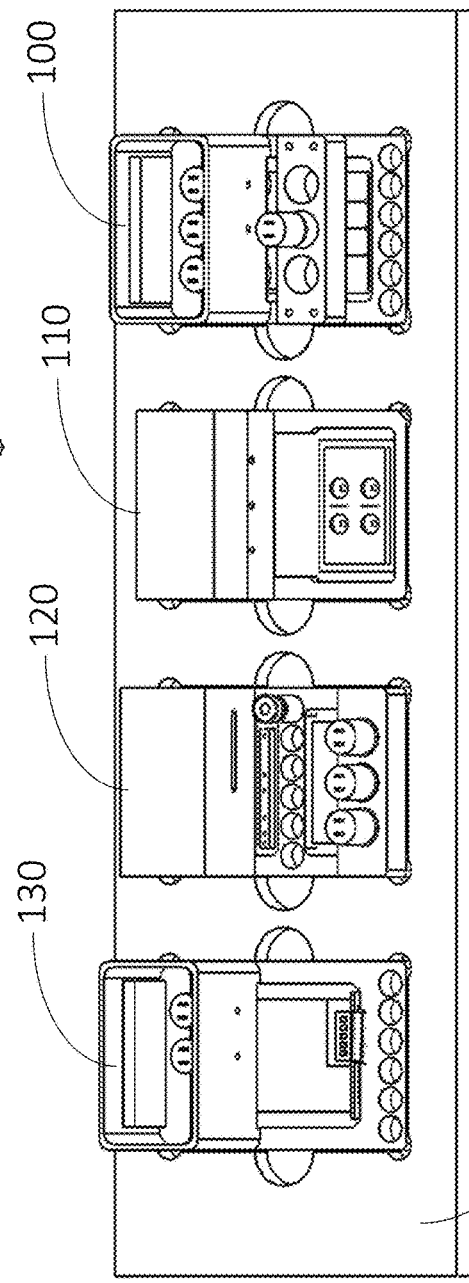

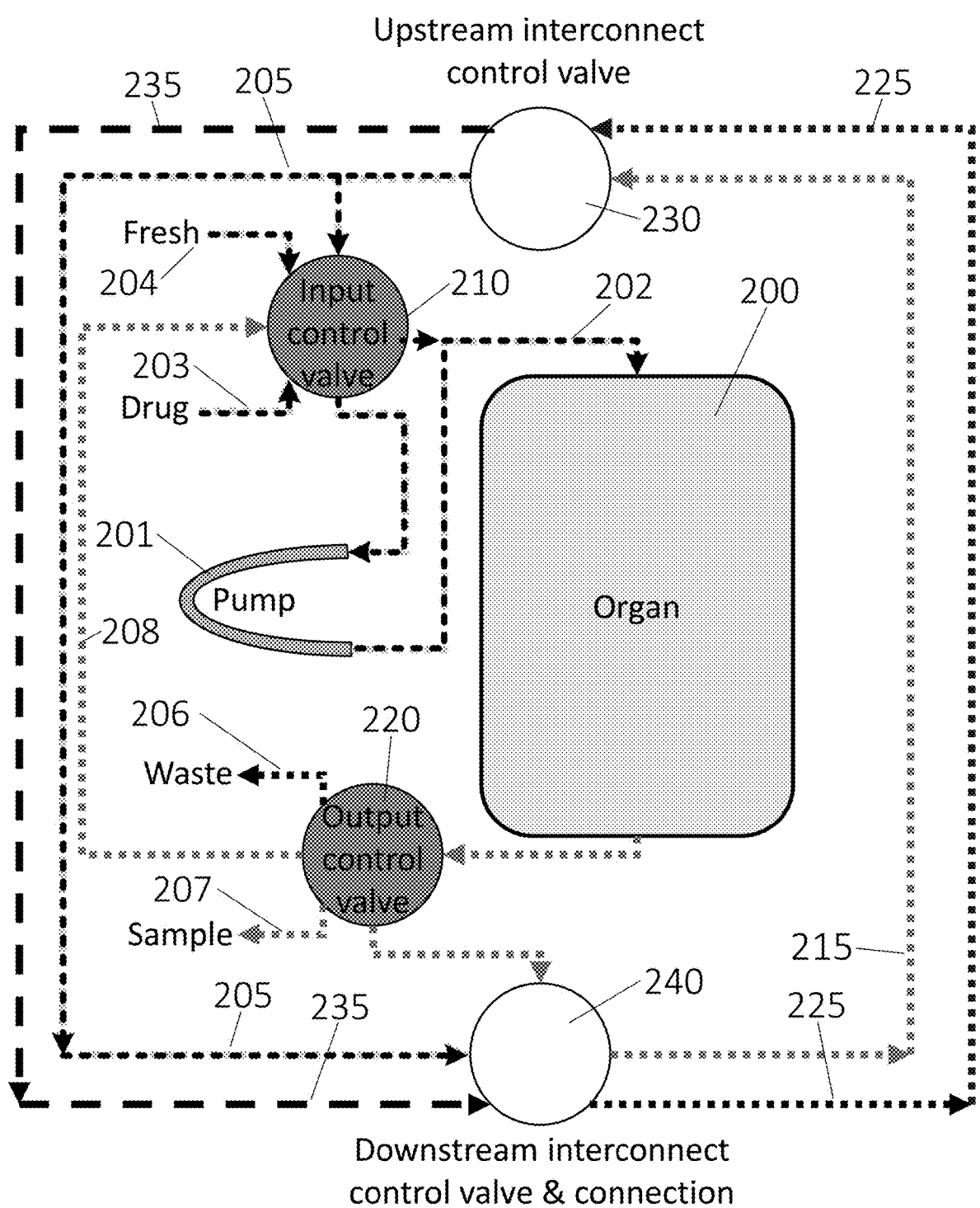

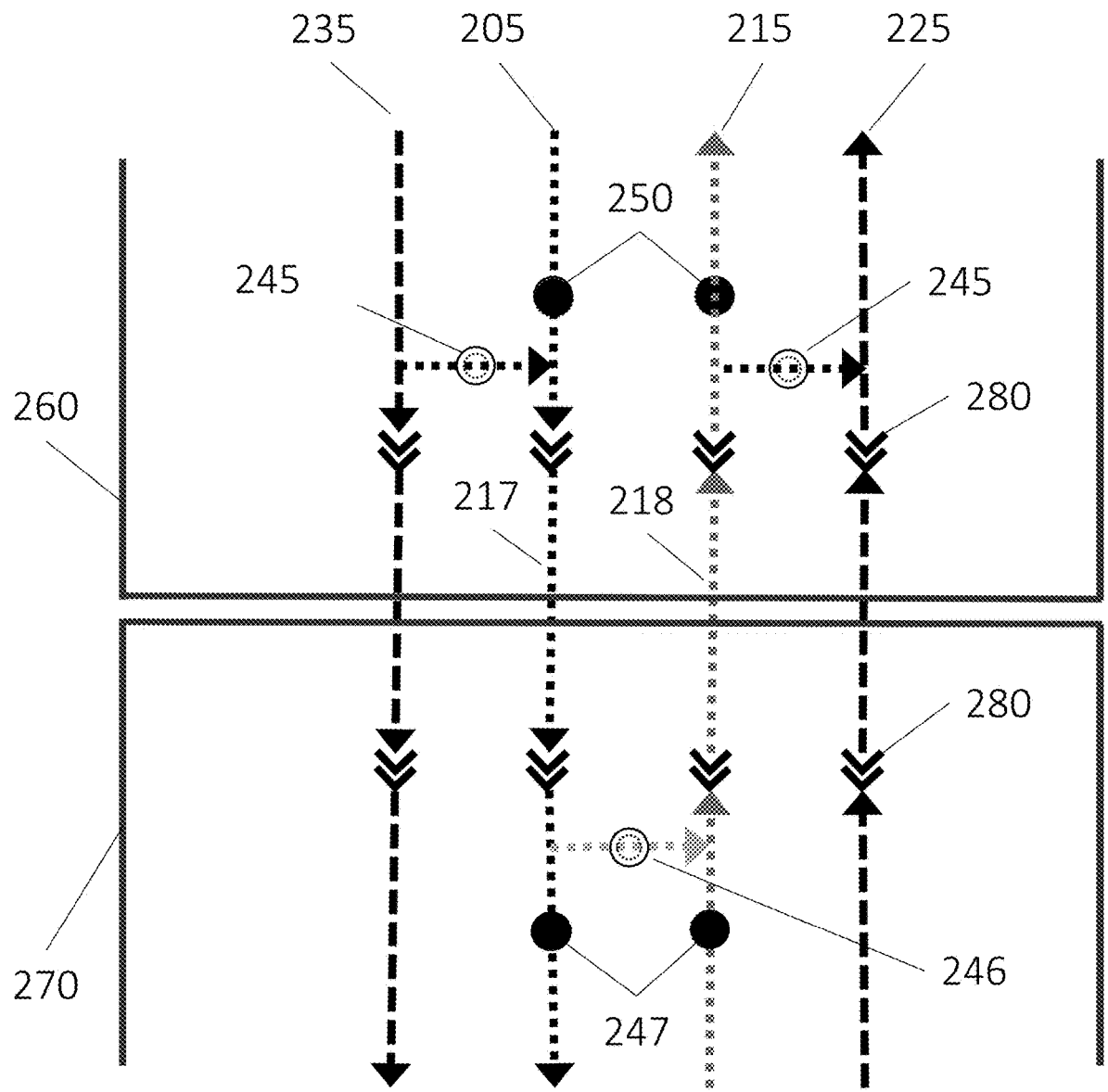

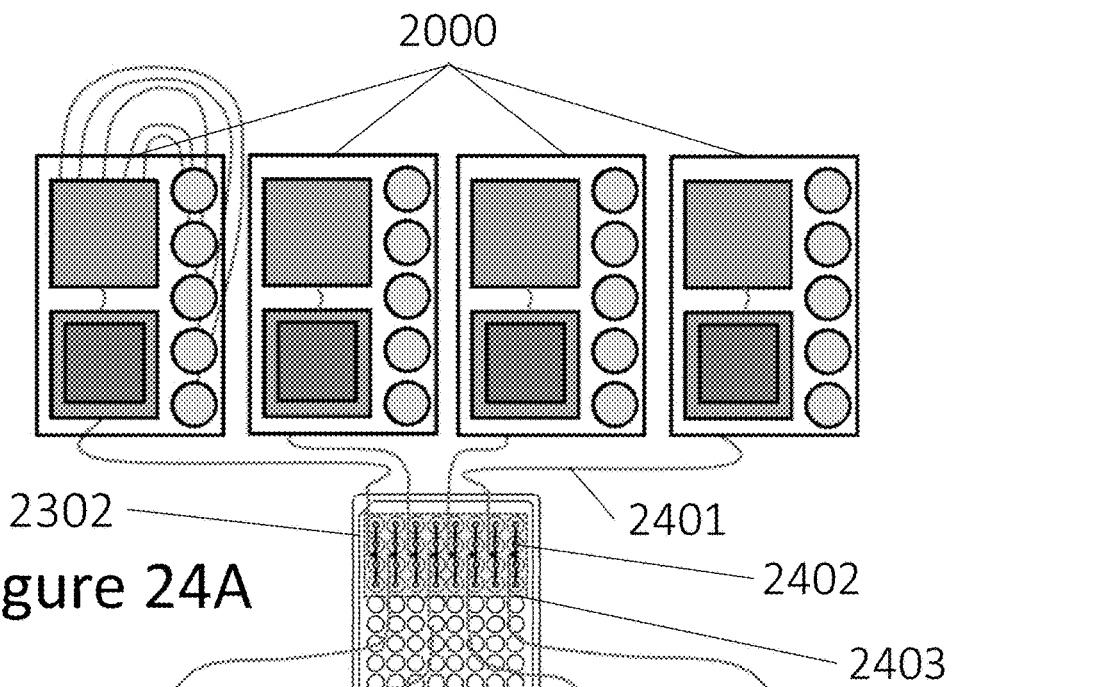
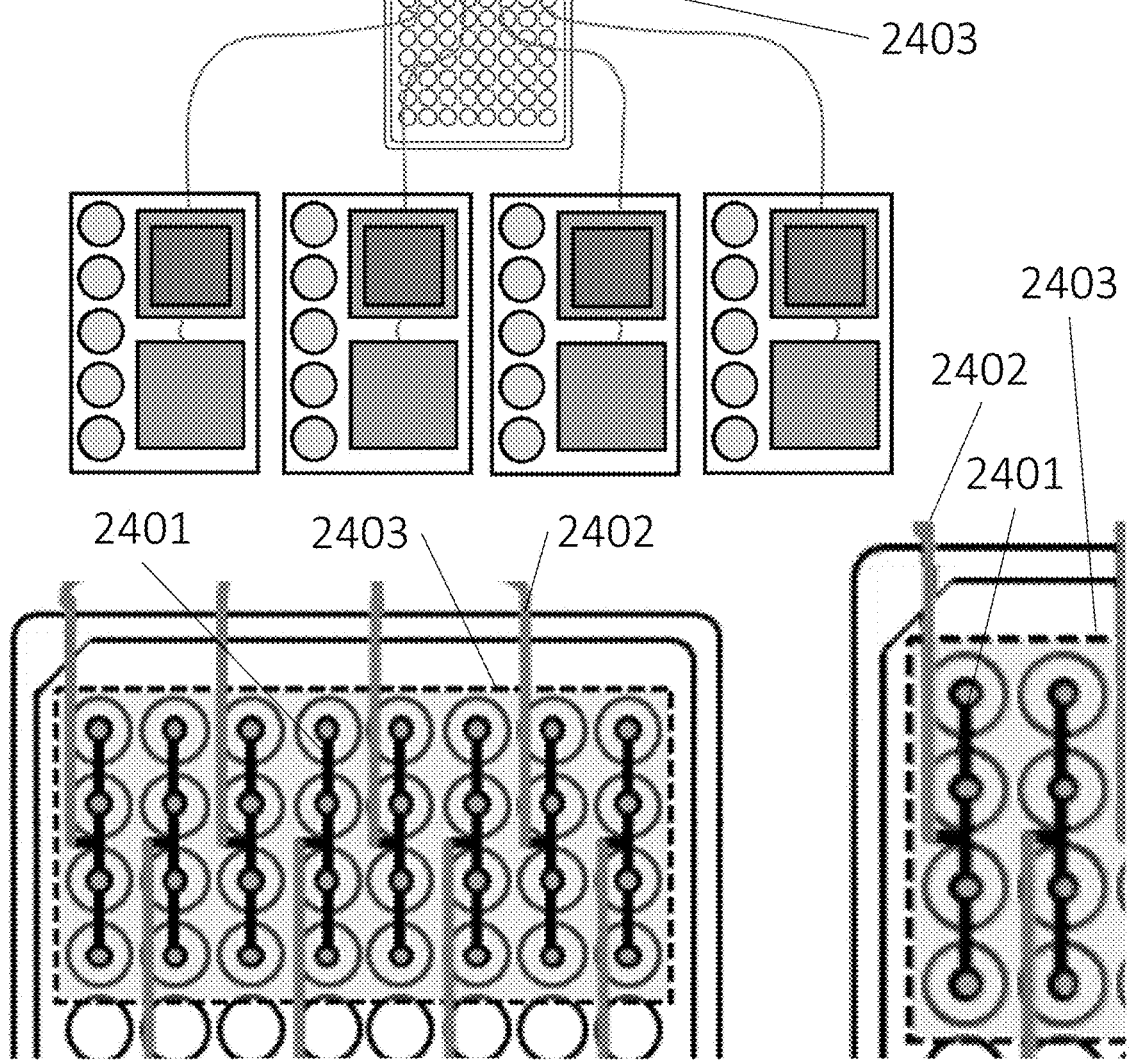
Figure 24A
Figure 24B
Figure 24C

Figure 25A
2402
Figure 25B
2502
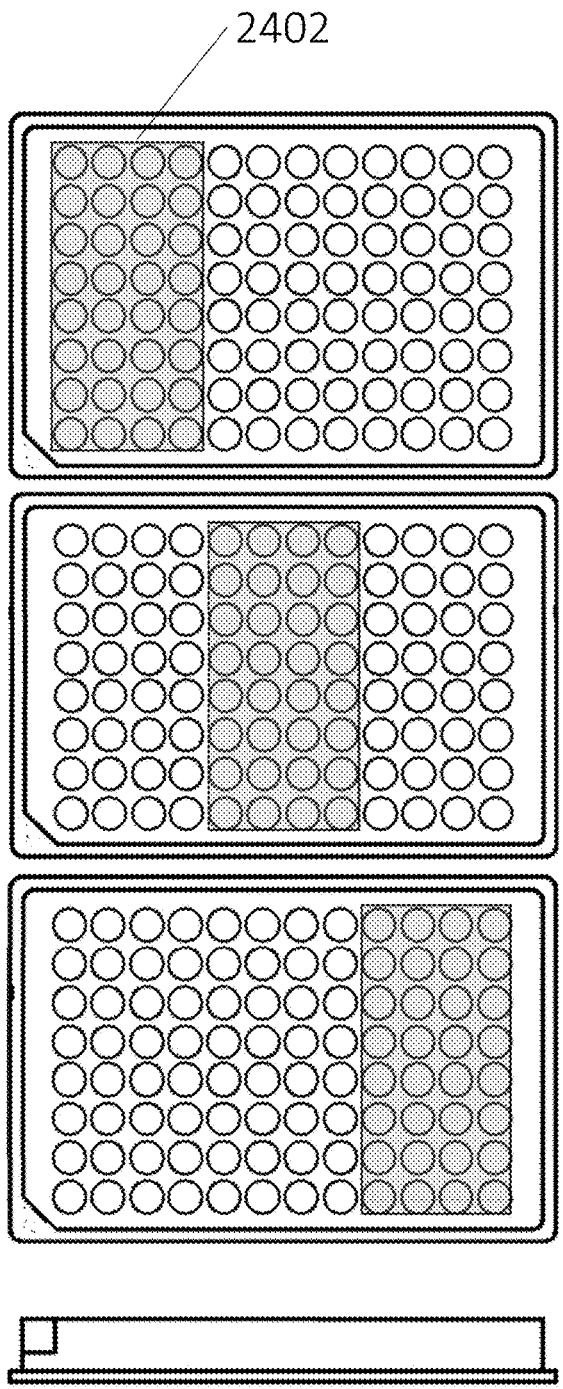
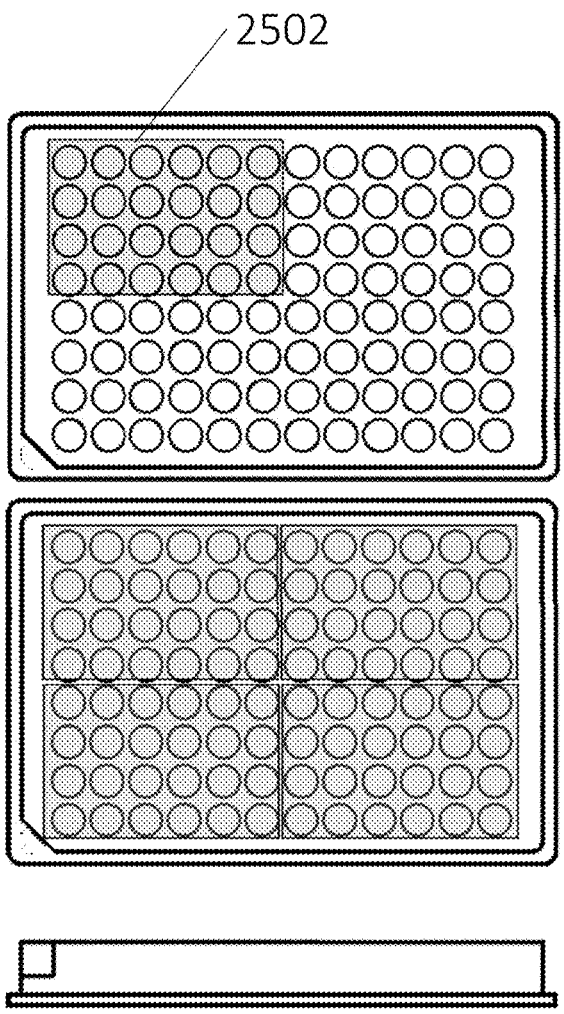

Figure 32A 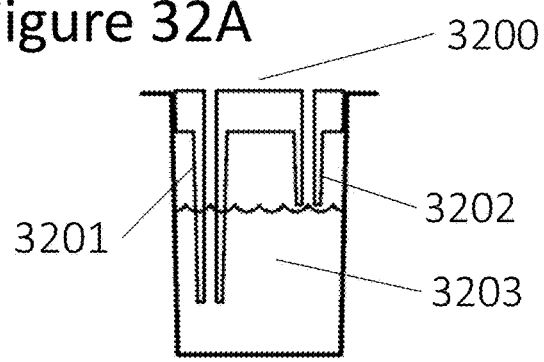 Figure 32B 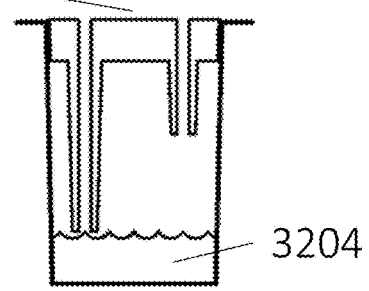
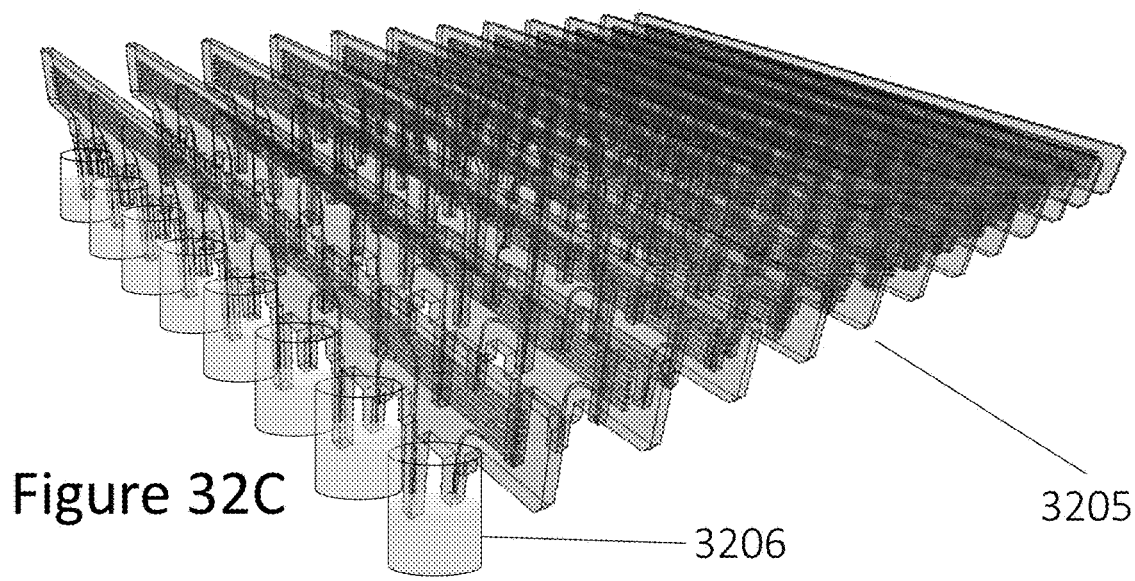
Figure 32C
Figure 32D
Figure 32E
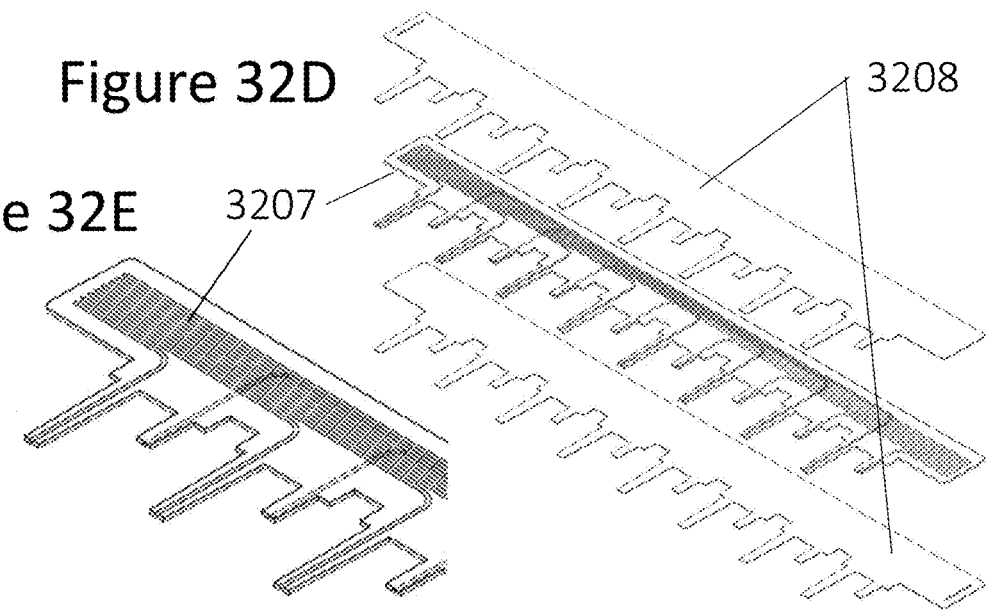

INTERCONNECTIONS OF MULTIPLE PERFUSED ENGINEERED TISSUE CONSTRUCTS AND MICROBIOREACTORS, MULTI-MICROFORMULATORS AND APPLICATIONS OF THE SAME

CROSS-REFERENCE TO RELATED PATENT APPLICATIONS

This application is a divisional patent application of, and claims benefit of U.S. patent application Ser. No. 15/191,092 (the '092 Application), filed Jun. 23, 2016, now U.S. Pat. No. 10,023,832, which itself claims priority to and the benefit of, pursuant to 35 U.S.C. § 119(e), U.S. Provisional Patent Application Ser. Nos. 62/183,571, 62/193,029, 62/276,047 and 62/295,306, filed Jun. 23, 2015, Jul. 15, 2015, Jan. 7, 2016 and Feb. 15, 2016, respectively. Each of the above-identified applications is incorporated herein in its entirety by reference.

The '092 Application is also a continuation-in-part application of U.S. patent application Ser. No. 13/877,925 (the '925 application), Ser. No. 14/363,074 (the '074 application), Ser. No. 14/646,300 (the '300 application) and Ser. No. 14/651,174 (the '174 application), filed Jul. 16, 2013, Jun. 5, 2014, May 20, 2015 and Jun. 10, 2015, respectively. The '925 application, now abandoned, is a national stage entry of PCT Application Serial No. PCT/US2011/055432, filed Oct. 7, 2011, which claims priority to and the benefit of U.S. Provisional Patent Application Ser. No. 61/390,982, filed Oct. 7, 2010. The '074 application, now U.S. Pat. No. 10,078,075, is a national stage entry of PCT Application Serial No. PCT/US2012/068771, filed Dec. 10, 2012, which claims priority to and the benefit of U.S. Provisional Patent Application Ser. Nos. 61/569,145, 61/697,204 and 61/717,441, filed Dec. 9, 2012, Sep. 5, 2012 and Oct. 23, 2012, respectively. The '300 application, now U.S. Pat. No. 9,874,285, is a national stage entry of PCT Application Serial No. PCT/US2013/071026, filed Nov. 20, 2013, which claims priority to and the benefit of U.S. Provisional Patent Application Ser. Nos. 61/729,149, 61/808,455, and 61/822,081, filed Nov. 21, 2012, Apr. 4, 2013 and May 10, 2013, respectively. The '174 application, now U.S. Pat. No. 9,618,129, is a national stage entry of PCT Application Serial No. PCT/US2013/071324, filed Nov. 21, 2013, which claims priority to and the benefit of U.S. Provisional Patent Application Ser. Nos. 61/808,455 and 61/822,081, filed Apr. 4, 2013 and May 10, 2013, respectively. Each of the above-identified applications is incorporated herein in its entirety by reference.

Some references, which may include patents, patent applications, and various publications, are cited and discussed in the description of the present invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT OF FEDERALLY SPONSORED RESEARCH

The present invention was made with government support under Contract Nos. W911NF-12-2-0036, awarded by the Defense Advanced Research Projects Agency, DTRA100271A-5196 and HDTRA1-09-1-00-13, awarded by the Defense Threat Reduction Agency, and 1UH2-TR000491-01, awarded by the National Institutes of Health. The government has certain rights in the invention.

FIELD OF THE INVENTION

The present invention relates generally to a microfluidic system, and more particularly to MicroFormulators, interconnections of multiple perfused engineered tissue constructs and microbioreactors, and applications of the same.

BACKGROUND INFORMATION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

There is a growing literature on the use of interconnected organs-on-chips or tissue chip constructs to discover and develop drugs, determine drug safety and toxicology, develop tissue engineered constructs, and program the differentiation of induced pluripotent stem cells. In current systems presently coupling different organs together to study organ-organ and organ-drug-organ interactions, the interconnections are primarily in the form of on-chip microfluidic channels to connect organs that are on the same chip, or tubing that connects organs on different chips. The difficulty with this approach is that with the fixed channels, organs cannot be inserted, removed, or replaced because all of the organs are on a single microfluidic chip and, were a single organ to fail, all of the organs on the chip may need to be discarded. If separate organs are connected by tubing, it is difficult to make or break connections without either losing fluid or introducing bubbles. Furthermore, the volume of tubing is typically much greater than that of microfluidic channels and leads to well-known difficulties with meeting the design requirements that the total fluidic volume be properly scaled to that of the organs under study. Finally, the addition and removal of tubing from open holes present serious problems in the sterilization of the device, in that pathogens that have contaminated the surface of the device can be pushed into the fluid path by the act of insertion of the tubing. There is no easy way to sterilize such an insertion-based tubing system Commercial fluidic systems, such as those used in trucks, trains, and industrial processes, use an interconnect that is a two-part connector with spring-actuated valves in each half, so that flow is arrested from either side when the two parts are separated. It is difficult to implement this technique in the realm of small physical dimensions, tubing diameters, tubing lengths, and small tubing volumes required for interconnected organs-on-chips. Furthermore, there is no easy way to sterilize such systems both before and after making and breaking connections.

Therefore, there is a need to interconnect separate Integrated Organ Microfluidics (IOM) modules in a sterile, low-volume manner that avoids fluid loss and introduction of air bubbles and allows ready sterilization of the interior and exterior of the fluid interconnect pathways.

In addition, in vitro cell culture is a mainstay of the drug discovery and development processes, toxicology, and biological discovery. At present, high throughput screening (HTS) uses a centralized robot to move well plates between separate single-operation stations, most importantly the fluid-handling robot. The limitation of this approach is that it is difficult or impossible to perform multiple operations on multiple well plates simultaneously. The economics of this approach is that in a system with N well plates, a single well plate can occupy any single station, e.g., fluid handing robot or scanner, for no more than 1/Nth of the duration of the experiment. This makes the long-term, physiologically realistic drug-delivery pharmacokinetics difficult to realize in an HTS well-plate environment.

Furthermore, the ability to vary the concentration of key drugs, nutrients, or toxins over an extended period of time is critical to understanding a variety of biological processes. There are a number of fields in biology and medicine wherein it is desired to perfuse two- and three-dimensional tissue constructs over long periods of time using culture media that contains concentrations of nutrients, growth factors, drugs, and toxins that may vary in time. One example of this is use of organoid culture to identify the optimum drug and drug dosing schedule and concentration to best treat the cancer of a particular patient. At present, this can be done by dissociating a biopsy sample or a resected tumor into individual cells and allowing the resulting heterogeneous population of cells to self-assemble into spherical organoids that are typically between 100 and 500 microns in diameter. A single organoid is placed in each well of a 96 or 384 well plate and is maintained in culture for intervals of time ranging between seven days and four weeks. The growth of the organoid and its response to drugs and toxins are then monitored. This is a time-consuming process because it requires daily media exchanges and carefully timed delivery of drugs to each well. The complexity of the process limits the number of wells that can be maintained, and reduces the probability of identifying the optimum drug and drug-delivery schedule. The combinatorics become even more problematic if the treatment regimen requires two drugs delivered at different times. Furthermore, it is difficult to delivery time-dependent, physiologically realistic drug delivery protocols over hours to days using a pipetting robot. Without continuous perfusion, the size of the organoid that can be supported with only daily media changes is limited, and hence there is a need to be able to continuously and independently perfuse each well of a multi-well plate.

A similar set of problems arises with the determination of the optimum sequence and concentrations for the different growth factors, nutrients, and small molecules and drugs that are delivered to induced pluripotent stem cells (iPSCs) to cause them to differentiate into a particular cellular phenotype. At present, this is done using automated fluid-handling robots, but the size and cost of the robot and the requirement that large numbers of well plates must be serviced by a single robot limits the number of combinations of growth factors, etc., that can be assayed. With pipette delivery by a central fluid-handling robot, the delivery of the required growth factors, etc., is in the form of a bolus dose, which may trigger different responses in the cells than would a steady or slowly varying concentration.

The measurement of the toxicity of drugs and environmental and industrial toxins is similarly limited by the throughput of a central fluid-handling robot that is required to both perfuse the cells or organoids or tissue constructs and deliver a range of drugs or toxins to the cells or organoids with a physiologically realistic temporal concentration profile.

Therefore, a heretofore unaddressed need exists in the art to address the aforementioned deficiencies and inadequacies.

SUMMARY OF THE INVENTION

In one aspect, the invention relates to an integrated bio-object microfluidics module. The bio-object includes an organ, a group of cells, tissues, or the like. In one embodiment, the integrated bio-object microfluidics module includes an input bus, and an output bus, being connectable to an interface that allows the integrated bio-object microfluidics module to be connected to another integrated bio-object microfluidics module, or other microfluidic module of a similar design; an upstream interconnection bus control valve fluidic coupled to the input bus, and a downstream interconnection bus control valve fluidic coupled to the output bus; an arterial bus line, a venous bus line, a wash bus line, and a waste bus line, each fluidically connecting between the upstream interconnection bus control valve and the downstream interconnection bus control valve; an input control valve fluidically connecting to the arterial bus line, the upstream interconnection bus control valve, the bio-object and a plurality of inlets, and an output control valve fluidically connecting to the bio-object, the input control valve, the downstream interconnection bus control valve and a plurality of outlets; and a pump fluidically connecting between the input control valve and the bio-object.

The plurality of inlets is adapted for providing a plurality of fluids, and the plurality of outlets is adapted for collecting waste and sample for analysis.

Each of the input control valve, the output control valve, the upstream interconnection bus control valve and the downstream interconnection bus control valve comprises a plurality of control ports, each control port being individually controllable in an open state in which a flow of fluid is allowed or a closed state in which a flow of fluid is occluded, such that the integrated bio-object microfluidics module is selectively operable in one of a Run Isolated Mode, a Run Interconnected Mode, and a Sterilize/Wash Mode.

In one embodiment, each of the input control valve, the output control valve, the upstream interconnection bus control valve and the downstream interconnection bus control valve comprises a multiport, rotary planar valve.

In one embodiment, each of the upstream interconnection bus control valve and the downstream interconnection bus control valve comprises a plurality of toggle valves.

In one embodiment, each toggle valve comprises a compression actuator, and a handle engaged with the compression actuator for controlling the compression actuator to operably compress a microfluidic channel underneath.

In another embodiment, each toggle valve is a double-pole, single-throw opposite toggle valve comprising a foreground compression actuator, a background compression actuator, and a handle engaged with the foreground compression actuator and the background compression actuator for controlling them to compress a foreground microfluidic channel and a background microfluidic channel, respectively.

In yet another embodiment, each toggle valve comprises a body defining a central axle hole, two ball detents, a compression actuator and a handle respectively extending from the body such that the actuator and the handle are angled, wherein the body is rotatable into one of two states controlled by the two ball detents so as to actuate the compression actuator to occlude the microfluidic channel underneath.

In one embodiment, the integrated bio-object microfluidics module further has a microcontroller for individually controlling each port of the input control valve, the output control valve, the upstream interconnection bus control valve and the downstream interconnection bus control valve. In one embodiment, the microcontroller is provided with a wireless communication protocol.

In another aspect, the present invention relates to an interconnect system usable for fluidically connecting a first microfluidics module to a second microfluidics module. In one embodiment, the interconnect system has a first interface and a second interface for the first microfluidics module and the second microfluidics module, respectively. Each interface includes a first surface, an opposite, second surface, and a body defined therebetween; connection busses defined through the body, the connection busses being fluidically connecting to a wash bus line, an arterial bus line, a venous bus line, and a waste bus line of a respective microfluidics module through interface tubing ports on the first surface of each interface; and an alignment pin and an alignment hole spatially formed on the second surface of each interface such that when connected, the alignment pin of the first interface fits into the alignment hole of the second interface, and vice versa, and the wash bus line, the arterial bus line, the venous bus line, and the waste bus line of the first microfluidics module are fluidically connected to those of the second microfluidics module, respectively, through the connection busses on the second surface of the first and second interfaces.

In one embodiment, each interface comprises a pair of magnets formed on the second surface for facilitating alignment and attachment of the first and second interfaces.

In one embodiment, the connection busses on the second surface of each interface are configured such that the waste line of the first microfluidics module is occluded by a flow stopping peg, and/or the wash line of the second microfluidics module is occluded by a rubber stopper.

In one embodiment, the arterial bus line and the venous line of one of the first and second microfluidics modules are fluidically connectable via internal tubing or selectively occluded.

In yet another aspect, the present invention relates to a microfluidics module tray. In one embodiment, the microfluidics module tray comprises a plurality of microfluidics modules arranged in an array; and a plurality of interfaces, each interface being recited above, wherein each two adjacent microfluidics modules are interconnected by respective two interfaces.

In one embodiment, the plurality of microfluidics modules comprises at least one integrated bio-object microfluidics module.

In one embodiment, the plurality of microfluidics modules further comprises at least one of a Cardiopulmonary Assist Module, a MicroFormulator ($\mu$F), and a MicroClinical Analyzer ($\mu$CA).

In a further aspect, the present invention relates to a system for individually addressing each and every well or sets of wells in sub-zones of a well plate. In one embodiment, the system comprises at least one MicroFormulator. Each MicroFormulator has a plurality of reservoirs; at least one selector valve fluidically coupled to the plurality of reservoirs to select at least one reservoir; and at least one pump fluidically coupled to the at least one selector valve to withdraw fluid from the selected reservoir and deliver it to at least one output tube, wherein the at least one output tube is connectable to a well of the well plate for addressing the well with the fluid output from the at least one output tube.

In one embodiment, the at least one selector valve comprises a multiport, rotary planar valve.

In one embodiment, the multiport, rotary planar valve comprises a missing-ball, normally open rotary planar valve (NO-RPV), or a fixed-ball, rotating-actuator, normally closed rotary planar valve (NC-RPV).

In one embodiment, the at least one selector valve is configured to select different reservoirs at different periods of time.

In one embodiment, the at least one pump is driven such that the fluid of the selected reservoir outputs from the at least one output tube at a predetermined flow rate.

In one embodiment, the predetermined flow rate varies with time.

In one embodiment, the at least one selector valve comprises a first selector valve fluidically coupled to the plurality of reservoirs to select at least one reservoir, and a second selector valve fluidically coupled to the at least one pump for directing the fluid of the selected reservoir output from the at least one pump to one of the multiple output tubes, wherein each output tube in turn is connectable to an individual well of the well plate.

In one embodiment, the at least one MicroFormulator comprises a first MicroFormulator and a second MicroFormulator, configured such that the first MicroFormulator delivers the fluid of the selected reservoir individually to each well of the well plate and a second, MicroFormulator independently removes the fluid from each well of the well plate.

In one embodiment, the at least one MicroFormulator comprises eight MicroFormulators, each MicroFormulator configured to individually address 12 wells of the well plate.

In one embodiment, the system further includes at least one splitter fluidically coupled to the at least one output tube and respective wells of the well plate for addressing the respective wells with the fluid output from the at least one output tube.

In one embodiment, the system further includes comprising a microcontroller for individually controlling the at least one selector valve and the at least one pump. The microcontroller is provided with a wireless communication protocol.

In yet a further aspect, the present invention relates to a microfluidics module molded from an elastomeric material. In one embodiment, the microfluidics module comprises a fluidic circuit having channels, chambers, vials, wells and fluid ports formed such that when at least one selector valve and at least one pump are placed on the fluidic circuit, the fluidic circuit together with the at least one selector valve and the at least one pump operably construe at least one MicroFormulator for individually addressing each of the wells.

In one embodiment, the microfluidics module enables individually addressing each of the wells with time-division multiplexing.

In one embodiment, the microfluidics module further comprises multiple flat layers bonded sequentially or simultaneously to define the fluidic circuit.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

FIGS. 1B and 1C show schematically perspective and top views, respectively, of an implementation of interconnected organs according to one embodiment of the present invention.

FIG. 2A shows schematically a layout of the fluidic connections into, within, and out of a generic organ Perfusion Controller according to one embodiment of the present invention.

FIG. 2C shows schematically a diagram of the Sterilize/Wash Mode showing how the Sterilize/Wash Mode of the interconnect system is achieved by proper setting of the valves on both sides of the interconnect according to one embodiment of the present invention.

FIG. 24A shows eight single-channel µFs, each connected by means of a length of tubing to a four-well splitter mounted in a rigid sub-plate to address one-third of a well plate at a time according to one embodiment of the present invention.

FIGS. 24B and 24C show two close-up views of a portion of the system shown in FIG. 24A.

FIGS. 25A and 25B show schematically the process applied to one-third (FIG. 25A) or one-quarter (FIG. 25B) of a well plate at a time using an appropriately configured sub-plate, respectively, according to embodiments of the present invention.

FIGS. 32A-32E show an implementation of a mass-produced needle array that provides push-pull fluidic access to each well in a 96-well plate according to embodiments of the present invention. FIGS. 32A and 32B show that the fluid level does not exceed the level set by the short needle and is not less than the level of fluid set by the long needle. FIG. 32C shows how the needle arrays required to push-pull address all wells in a well plate could be created using a set of 12 parallel, planar needle arrays, each of which has eight needle pairs that couple to a single row of eight wells in a 96-well plate. FIGS. 32 D and 32E show how a single needle array could be created using hot embossing and thermal bonding.

DETAILED DESCRIPTION OF THE INVENTION

Figure 1A:
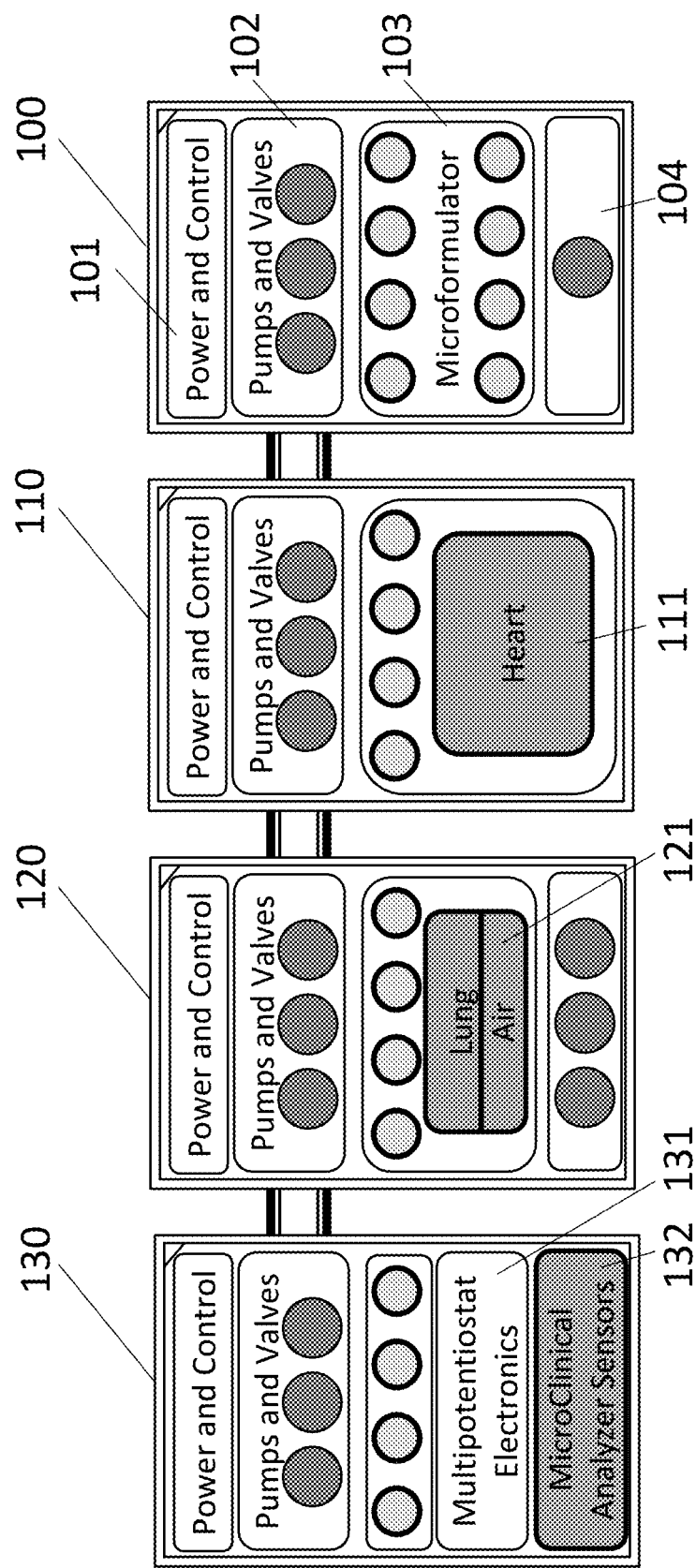
FIG. 1A shows schematically a block diagram of a simple two organ-on-chip system with a Perfusion Controller for each organ and an on-board MicroFormulator (µF) and MicroClinical Analyzer (µCA) according to one embodiment of the present invention.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the terms "MicroClinical Analyzer," "MicroChemical Analyzer," and their abbreviation "µCA" are exchangeable. The term "Perfusion Controller" and its abbreviation "PC" are exchangeable. The term "MicroFormulator" and its abbreviation "µF" are exchangeable. The term "Rotary Planar Peristaltic Micropump" and its abbreviation "RPPM" are exchangeable. The term "Rotary Planar Valve" and its abbreviation "RPV" are exchangeable. The term "Integrated Organ Microfluidics" and its abbreviation "IOM" are exchangeable. The term "Organ-on-Chip" and its abbreviation "OoC" are exchangeable. The term "tissue chip" and its abbreviation "TC" are exchangeable.

As used herein, the terms "fluidic path" and "fluidic channel" are exchangeable, and refer to a passage, a conduit, a groove, a furrow, or the like that allow a fluid to flow through it. Similarly, "bus line," "bus," and "line" can be used interchangeably and refer to a common fluidic supply line or a set of common fluidic supply lines.

The description is now made as to the embodiments of the present invention in conjunction with the accompanying drawings. In accordance with the purposes of the present invention, as embodied and broadly described herein, the present invention relates to systems and methods for the control of fluids in the long-term culture of cells in a wide variety of situations, including perfused engineered tissue constructs, also known as tissue chips or organs-on-chips, microbioreactors for culturing adherent or non-adherent cells with or without a supporting matrix, and well plates in any of their many configurations, including well plates with transwell inserts. Each of these applications has in common the need to (a) provide long-term perfusion (many days to weeks) of cells being grown at a high density, (b) minimize the volume of media to which the cells are exposed so as to minimize the dilution of factors that are secreted by the cells being grown, (c) support the controlled interaction and exchange of fluids between different reservoirs, (d) support the connection and disconnection of systems' components without the introduction of bubbles or microbial contamination, and (e) avoid large variations in the concentrations of nutrients and metabolic waste products, as would occur with only daily media changes as in conventional cell culture.

These points can be addressed in part by systems that are constructed using, for example, the Rotary Planar Peristaltic Micropump (RPPM) and Rotary Planar Valve (RPV) technologies described in PCT publication No. WO 2012/048261, entitled "PERISTALTIC MICROPUMP," by Gould et al., which includes the MicroFormulators. In certain embodiments, the present invention utilizes the normally closed rotary planar valve (NC-RPV) disclosed in PCT publication No. WO 2014/123600, entitled "NORMALLY CLOSED MICROVALVE AND APPLICATIONS OF THE SAME," by Block, et al. In certain embodiments, the present invention builds upon this foundation, as well as that described in PCT publication Nos. WO 2013/086505, entitled "INTEGRATED ORGAN-ON-CHIP SYSTEM AND APPLICATIONS OF THE SAME," by Wikswo et al., WO 2013/086486, entitled "INTEGRATED HUMAN ORGAN-ON-CHIP MICROPHYSIOLOGICAL SYSTEMS," by Wikswo et al., and WO 2014081840, entitled "ORGAN ON CHIP INTEGRATION AND APPLICATIONS OF THE SAME," by Block III et al., which present more details regarding Perfusion Controllers and MicroClinical Analyzers for monitoring cellular metabolic activity for organs-on-chips and other applications. Both PCT publication Nos. WO 2012/048261 and WO 2013/086505 provide detailed descriptions of various implementations of MicroFormulators that are capable of preparing custom formulations of cell culture media, including drugs, toxins, and growth factors, with the output being delivered to a single bioreactor, organ-on-a-chip, or other fluidic reservoir, or single set of such interconnected devices. Each of the above-identified PCT publications is incorporated herein in its entirety by reference. According to the present invention, the concept of the MicroFormulator is extended to provide the ability to deliver fluid, upon demand, to any one of multiple fluidic devices, whether they are bioreactors, organs-on-chips, individual wells in a well plate, or other fluidic reservoirs, and also independently remove fluid from these same reservoirs.

In certain aspects, the present invention relates to various means to improve the interconnection and control of multiple organs-on-chips, microbioreactors, MicroFormulators, Perfusion Controllers, MicroClinical Analyzers, and individual wells in a multi-well plate. In certain embodiments, the present invention provides means for sterile interconnection of multiple perfused engineered tissue constructs, microbioreactors, well plates and other microfluidic instruments and controllers.

The combination of computer-controlled pumps and valves provides coordinated fluid delivery and removal from multiple instances of small-volume reservoirs, whether they are an organ-on-chip or separate wells in a well plate. In certain aspects, the present invention addresses the need for regulating the flow of fluid into and out of the multiplicity of fluidic reservoirs required to maintain multiple, interconnected organs-on-chip bioreactors to ensure that an individual bioreactor can have its media recirculated as desired and volumes in multiple bioreactor reservoirs remain in balance so that the cross-connection of different organs and their associated media can be controlled. These operations in turn require computer software that can account for the pump delivery and withdrawal rates, and the volumes of fluid in the reservoirs, bioreactors, and tubing.

In one aspect, the invention relates to an integrated bio-object microfluidics module. The bio-object includes an organ, a group of cells, tissues, or the like. In one embodiment, the integrated bio-object microfluidics module includes an input bus, and an output bus, being connectable to an interface that allows the integrated bio-object microfluidics module to be connected to another integrated bio-object microfluidics module, or other microfluidic module of a similar design; an upstream interconnection bus control valve fluidic coupled to the input bus, and a downstream interconnection bus control valve fluidic coupled to the output bus; an arterial bus line, a venous bus line, a wash bus line, and a waste bus line, each fluidically connecting between the upstream interconnection bus control valve and the downstream interconnection bus control valve; an input control valve fluidically connecting to the arterial bus line, the upstream interconnection bus control valve, the bio-object and a plurality of inlets, and an output control valve fluidically connecting to the bio-object, the input control valve, the downstream interconnection bus control valve and a plurality of outlets; and a pump fluidically connecting between the input control valve and the bio-object.

The plurality of inlets is adapted for providing a plurality of fluids, and the plurality of outlets is adapted for collecting waste and sample for analysis Each of the input control valve, the output control valve, the upstream interconnection bus control valve and the downstream interconnection bus control valve comprises a plurality of control ports, each control port being individually controllable in an open state in which a flow of fluid is allowed or a closed state in which a flow of fluid is occluded, such that the integrated bio-object microfluidics module is selectively operable in one of a Run Isolated Mode, a Run Interconnected Mode, and a Sterilize/Wash Mode.

In one embodiment, the integrated bio-object microfluidics module further has a microcontroller for individually controlling each port of the input control valve, the output control valve, the upstream interconnection bus control valve and the downstream interconnection bus control valve. In one embodiment, the microcontroller is provided with a wireless communication protocol. In one embodiment, each of the input control valve, the output control valve, the upstream interconnection bus control valve and the downstream interconnection bus control valve comprises a multiport, rotary planar valve.

In one embodiment, each of the upstream interconnection bus control valve and the downstream interconnection bus control valve comprises a plurality of toggle valves.

In one embodiment, each toggle valve comprises a compression actuator, and a handle engaged with the compression actuator for controlling the compression actuator to operably compress a microfluidic channel underneath. In another embodiment, each toggle valve is a double-pole, single-throw opposite toggle valve comprising a foreground compression actuator, a background compression actuator, and a handle engaged with the foreground compression actuator and the background compression actuator for controlling them to compress a foreground microfluidic channel and a background microfluidic channel, respectively. In yet another embodiment, each toggle valve comprises a body defining a central axle hole, two ball detents, a compression actuator and a handle respectively extending from the body such that the actuator and the handle are angled, wherein the body is rotatable into one of two states controlled by the two ball detents so as to actuate the compression actuator to occlude the microfluidic channel underneath.

In another aspect, the present invention relates to an interconnect system usable for fluidically connecting a first microfluidics module to a second microfluidics module. In one embodiment, the interconnect system has a first interface and a second interface for the first microfluidics module and the second microfluidics module, respectively. Each interface includes a first surface, an opposite, second surface, and a body defined therebetween; connection busses defined through the body, the connection busses being fluidically connecting to a wash bus line, an arterial bus line, a venous bus line, and a waste bus line of a respective microfluidics module through interface tubing ports on the first surface of each interface; and an alignment pin and an alignment hole spatially formed on the second surface of each interface such that when connected, the alignment pin of the first interface fits into the alignment hole of the second interface, and vice versa, and the wash bus line, the arterial bus line, the venous bus line, and the waste bus line of the first microfluidics module are fluidically connected to those of the second microfluidics module, respectively, through the connection busses on the second surface of the first and second interfaces.

In one embodiment, each interface comprises a pair of magnets formed on the second surface for facilitating alignment and attachment of the first and second interfaces.

In one embodiment, the connection busses on the second surface of each interface are configured such that the waste line of the first microfluidics module is occluded by a flow stopping peg, and/or the wash line of the second microfluidics module is occluded by a rubber stopper.

In one embodiment, the arterial bus line and the venous line of one of the first and second microfluidics modules are fluidically connectable via internal tubing or selectively occluded.

In yet another aspect, the present invention relates to a microfluidics module tray. In one embodiment, the microfluidics module tray comprises a plurality of microfluidics modules arranged in an array; and a plurality of interfaces, each interface being recited above, wherein each two adjacent microfluidics modules are interconnected by respective two interfaces.

In one embodiment, the plurality of microfluidics modules comprises at least one integrated bio-object microfluidics module.

In one embodiment, the plurality of microfluidics modules further comprises at least one of a Cardiopulmonary Assist Module, a MicroFormulator, and a MicroClinical Analyzer.

In a further aspect, the present invention relates to a system for individually addressing each and every well or sets of wells in sub-zones of a well plate. In one embodiment, the system comprises at least one MicroFormulator. Each MicroFormulator has a plurality of reservoirs; at least one selector valve fluidically coupled to the plurality of reservoirs to select at least one reservoir; and at least one pump fluidically coupled to the at least one selector valve to withdraw fluid from the selected reservoir and deliver it to at least one output tube, wherein the at least one output tube is connectable to a well of the well plate for addressing the well with the fluid output from the at least one output tube.

In one embodiment, the system further includes comprising a microcontroller for individually controlling the at least one selector valve and the at least one pump. The microcontroller is provided with a wireless communication protocol.

In one embodiment, the at least one selector valve comprises a multiport, rotary planar valve. In one embodiment, the multiport, rotary planar valve comprises a missing-ball, normally open rotary planar valve (NO-RPV), or a fixed-ball, rotating-actuator, normally closed rotary planar valve (NC-RPV).

In one embodiment, the at least one selector valve is configured to select different reservoirs at different periods of time.

In one embodiment, the at least one pump is driven such that the fluid of the selected reservoir outputs from the at least one output tube at a predetermined flow rate. In one embodiment, the predetermined flow rate varies with time.

In one embodiment, the at least one selector valve comprises a first selector valve fluidically coupled to the plurality of reservoirs to select at least one reservoir, and a second selector valve fluidically coupled to the at least one pump for directing the fluid of the selected reservoir output from the at least one pump to one of the multiple output tubes, wherein each output tube in turn is connectable to an individual well of the well plate.

In one embodiment, the at least one MicroFormulator comprises a first MicroFormulator and a second MicroFormulator, configured such that the first MicroFormulator delivers the fluid of the selected reservoir individually to each well of the well plate and a second MicroFormulator independently removes the fluid from each well of the well plate.

In one embodiment, the at least one MicroFormulator comprises eight MicroFormulators, each MicroFormulator configured to individually address 12 wells of the well plate.

In one embodiment, the system further includes at least one splitter fluidically coupled to the at least one output tube and respective wells of the well plate for addressing the respective wells with the fluid output from the at least one output tube.

In yet a further aspect, the present invention relates to a microfluidics module molded from an elastomeric or other material. In one embodiment, the microfluidics module comprises a fluidic circuit having channels, chambers, vials, wells and fluid ports formed such that when at least one selector valve and at least one pump are placed on the fluidic circuit, the fluidic circuit together with the at least one selector valve and the at least one pump operably construe at least one MicroFormulator for individually addressing each of the wells.

In one embodiment, the microfluidics module enables individually addressing each of the wells with time-division multiplexing.

In one embodiment, the microfluidics module further comprises multiple flat layers bonded sequentially or simultaneously to define the fluidic circuit.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

EXAMPLE I

Systems and Methods for Sterile Fluidic Interconnection of Multiple Perfused Engineered Tissue Constructs and Microbioreactors Certain aspects of the present invention relate to systems and methods for sterile interconnection of multiple perfused engineered tissue constructs and microbioreactors, particularly those utilized in Integrated Organ Microfluidics (IOM) modules that are interconnected to create a human-on-a-chip. In certain embodiments, the present invention addresses issues with sterilization, fluid containment, bubble generation and excess volumes associated with standard techniques that use simple microfluidic channels or tubing to connect organs. The novelty of the present invention is the use of interconnects that are configured as a parallel circuit with a wash line, an arterial line, a venous line, and a waste line. The present invention would be of potential value in any system or process that utilizes long-term culture of tissue-engineered organ constructs, especially for processes that need to add and remove analytical or control modules during the course of tissue culture. Similarly, the present invention would be of direct applicability to processes directed towards the differentiation of induced pluripotent stem cells (iPSC) to create cells of the chosen organ phenotype. Organ construct conditioned media can be temporarily or permanently fluidically interfaced with removable organ constructs by utilizing the present invention, thus providing influences that may guide the differentiation path of cells contained in organ constructs.

The same system of parallel fluidic channels and valves can also be used to insert and remove analytical instruments, such as a MicroClinical Analyzer (µCA) or a MicroFormulator (µF), from a bioreactor or an interconnected system of bioreactors or organs-on-chips.

According to embodiments of the present invention, the IOM interconnects can be as simple as an arterial and a venous line that connects all of the organs, a wash line that can deliver sterilizing solution and a washing solution, and a waste line which collects the sterilizing and wash solutions from each interconnect and returns it to a waste reservoir.

In recognition that it may be difficult to make and break a fluidic connection without the introduction of air, the system utilizes a pair of venting/flushing lines that can also provide, if desired, sterilizing fluid such as alcohol to sterilize the interface and the interconnect.

One of the key features of the present invention is that each interconnect is operated by a pair of rotary planar valves (RPVs) or mechanical toggle compression valves that control the fluid through the interconnect. Once the interconnects are connected, this pair of valves allows the sterilizing and wash solutions to be passed through all of the previously exposed interconnect tubing, followed by a wash solution that removes the sterilizing solution from each interconnect. Once the sterilization process is complete, these two rotary valves can be turned to the run position, at which point the wash and waste lines are isolated from the arterial and venous lines such that the wash and waste fluid can move the length of the coupled IOM system independent of the arterial and venous fluids, which can also run the length of the system through their respective channels. The use of rotary normally closed microfluidic valves simplifies the implementation of these valves in that the channels are always closed unless specifically actuated to allow fluid to be passed through them.

In one embodiment, each interconnect and its associated valves can be symmetrical such that the outlet of one module can mate with the input of another, and the modules can be inverted input-for-output without affecting the connectivity. Alternatively, the IOMs and their ports can be configured such that the IOMs can be interconnected only with a single orientation, but in an arbitrary IOM module order.

FIG. 1A shows a schematic illustration of an assembly of a set of coupled IOMs with arterial and venous connections as disclosed in PCT publication No. WO 2014081840, which is incorporated herein in its entirety by reference. Such a connected organ-on-chip system is termed a homunculus. Other than stating that a valved interconnect system would be used, there are no details provided as to how these connections are made. This figure shows a block diagram of a simple two organ-on-chip, with each having its own Perfusion Controller, and with on-board MicroFormulator (µF) and MicroClinical Analyzer (µCA). The µF 100 includes a power and control unit 101, pumps and control valves 102, a microfluidic with fluidic storage capabilities 103, and an input selector valve 104. A heart organ-on-chip Perfusion Controller 110 contains similar pumps and control valves and a heart chip 111. A lung organ-on-chip Perfusion Controller 120 contains similar pumps and control valves and a lung chip 121 which has both cells and the ability to oxygenate any blood surrogate in the device. A monitoring µCA 130 is capable of on-device measurements through the use of multipotentiostat electronics 131 and a sensor array 132. No connection details are provided.

FIGS. 1B and 1C show two views of an implementation of interconnected organs as shown in FIG. 1A. A µF 100, heart organ-on-chip Perfusion Controller 110, lung organ-on-chip Perfusion Controller 120, and MicroClinical Analyzer 130 realize the most basic two-organ homunculus. The organs are located on a connecting baseplate 140 in fluidic connection with each other, but with no illustrated details as to the nature of the connections.

FIG. 2A shows a layout of the fluidic connections into, within, and out of a generic organ Perfusion Controller (PC) according to one embodiment of the present invention. A generic organ 200 is directly driven by a local Perfusion Controller pump 201 via an input feed line 202. Input to this pump is selected by an input control valve 210 which can select either drug 203, fresh media 204 or input from the arterial bus 205, for example. Output from the organ 200, controllable via the output control valve 220, can either be delivered to waste 206, collected as a sample for further analysis 207, recirculated 208 to the input control valve, or sent to the venous bus 215, for example. The organ chip has the ability to address the arterial bus line 205 and the venous bus line 215. Different topologies of valves could implement these and other functions for localized control of each organ.

Input from the arterial bus line 205 can be selected by the upstream interconnection bus valve 230 and routed by the input control valve 210 to be delivered to the organ chip 200.

Similarly, output from the organ 200 can be selected by the output control valve 220 and routed by the downstream interconnection bus control valve 240 to the venous bus line 215.

Note that flow of the arterial and venous lines is clockwise in this possible realization of the interconnectable Perfusion Controller.

Flow of liquid through the wash bus 235 and the waste bus 225 is controlled by a pump at the end of these two busses in the interconnected system, as described below.

Figure 2B:
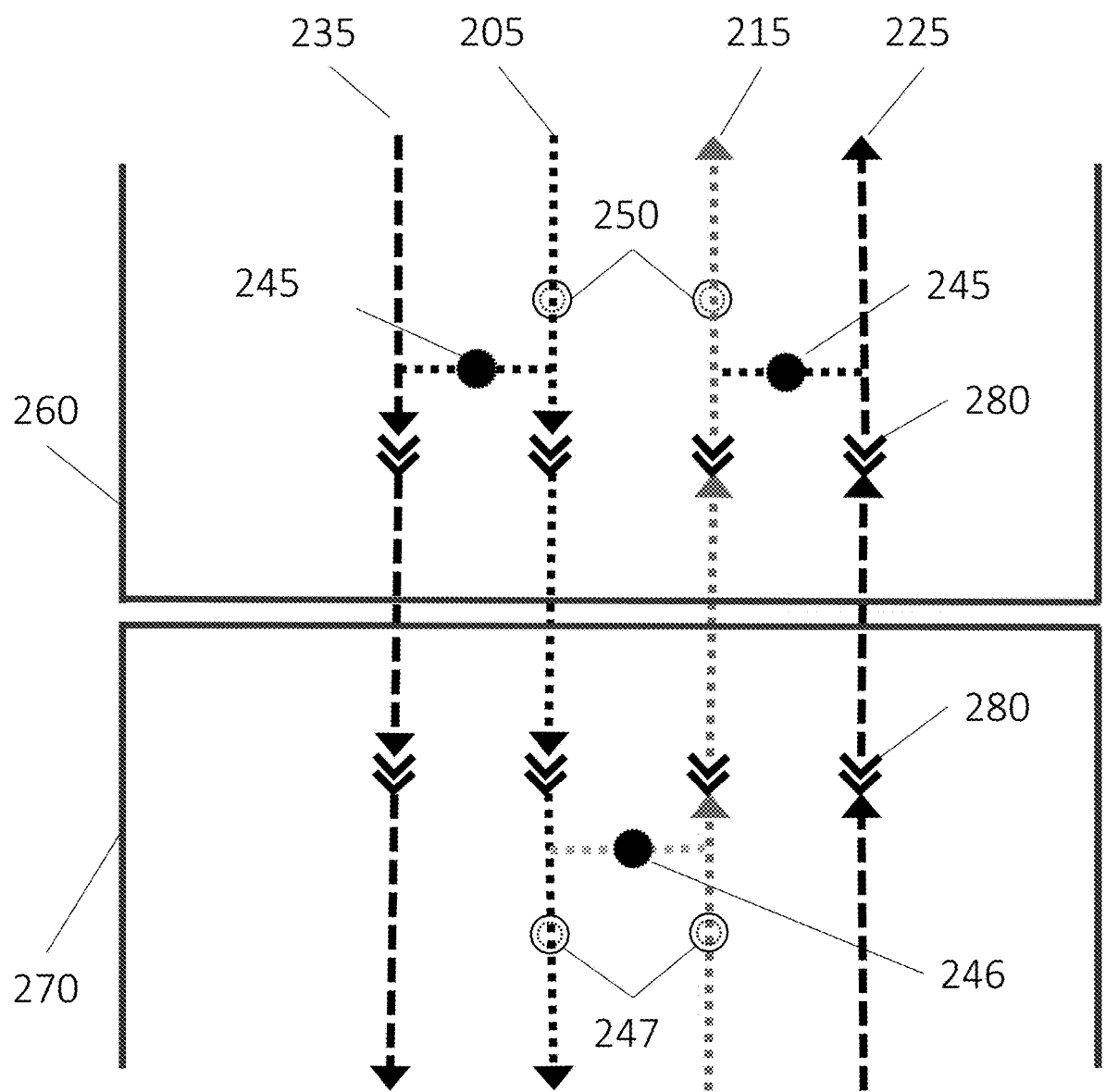
FIG. 2B shows schematically a diagram of the Run Interconnected Mode showing an interconnect between two separate modules with the interconnecting system valves and fluidic bus lines according to one embodiment of the present invention.

FIG. 2B is a diagram of an interconnect between two separate modules 260 and 270, whether they are Perfusion Controllers, MicroClincal Analyzers, MicroFormulators, Cardiopulmonary Assist Modules, or other devices, with the interconnecting system valves and fluidic bus lines. There are four parallel lines that cross between the upper proximal module 260 and lower distal module 270: a wash line 235 for delivery of a detergent, sterilant, and rinse solutions; an arterial line 205 to deliver fresh media; a venous line 215 to return conditioned media to the Cardiopulmonary Assist Module; and a waste line 225 into which the detergent, sterilant, and rinse solutions are removed from the system. Solid circles are closed valves, and open circles are open valves. The arrowheads designate that fluid is flowing in that direction. Line segments without fluid flow are without arrowheads. Hence this system provides fluidic connection for wash/sterilize/rinse 235 and arterial 205 solutions to flow from the proximal module 260 to the distal module 270, and venous 215 and waste 225 solutions to flow from the distal module 270 to the proximal module 260. The double-headed arrows 280 represent the interruptible connection between modules 260 and 270. These lines are controlled by open (open circles) control valve points 250 and 247 and closed (solid circles) control valve points 245 and 246 to route fluid either independently along the parallel lines in the Run Interconnected Mode (as shown in FIG. 2B), or to wash the interconnects in the SterilizeWash Mode (as shown in FIG. 2C), or the Run Isolated Mode. FIG. 2B shows the parallel wash, arterial, venous, and waste lines, with valves 245 closed to block the horizontal exchange of fluid between these lines.

FIG. 2C is a schematic illustration of the Sterilize/Wash Mode showing how the Sterilize/Wash Mode and the Run Mode of the interconnect system are achieved by toggling of valves on both the 260 and 270 sides of the interconnect. In the Sterilize/Wash Mode, valves blocking the horizontal connections 245 and 246 are now open, allowing flow of wash/sterilize/rinse solution 235 through the arterial 217 and venous 218 interconnect lines, which are now isolated from the corresponding lines in the body of the module by closed valves 247 and 250. Note that there is an asymmetry between the valves at the bottom (downstream) side of 260 and the top (upstream) side of 270. The valves 245 in the upper TOM 260 engage and disengage connections between wash and arterial, and venous and waste, in the fluidics within IOM 260. In the lower IOM 270, there is simply a valved connection 246 between the arterial and venous interconnect lines to enable the sterilization and wash fluids to pass through all four interconnect lines, thereby sterilizing and washing the entire interconnect, while valves 247 to shut off the arterial and venous lines so that sterilize/wash fluid cannot enter the organ fluidics in 270. Note that there may be short stubs of fluid immediately adjacent to a closed control point that are not washed by through-flow, but the short length of these stubs and the convective and diffusive movement of sterilizing and washing solutions during the sterilization and wash steps will render these stubs both sterile and then washed.

Figure 3:
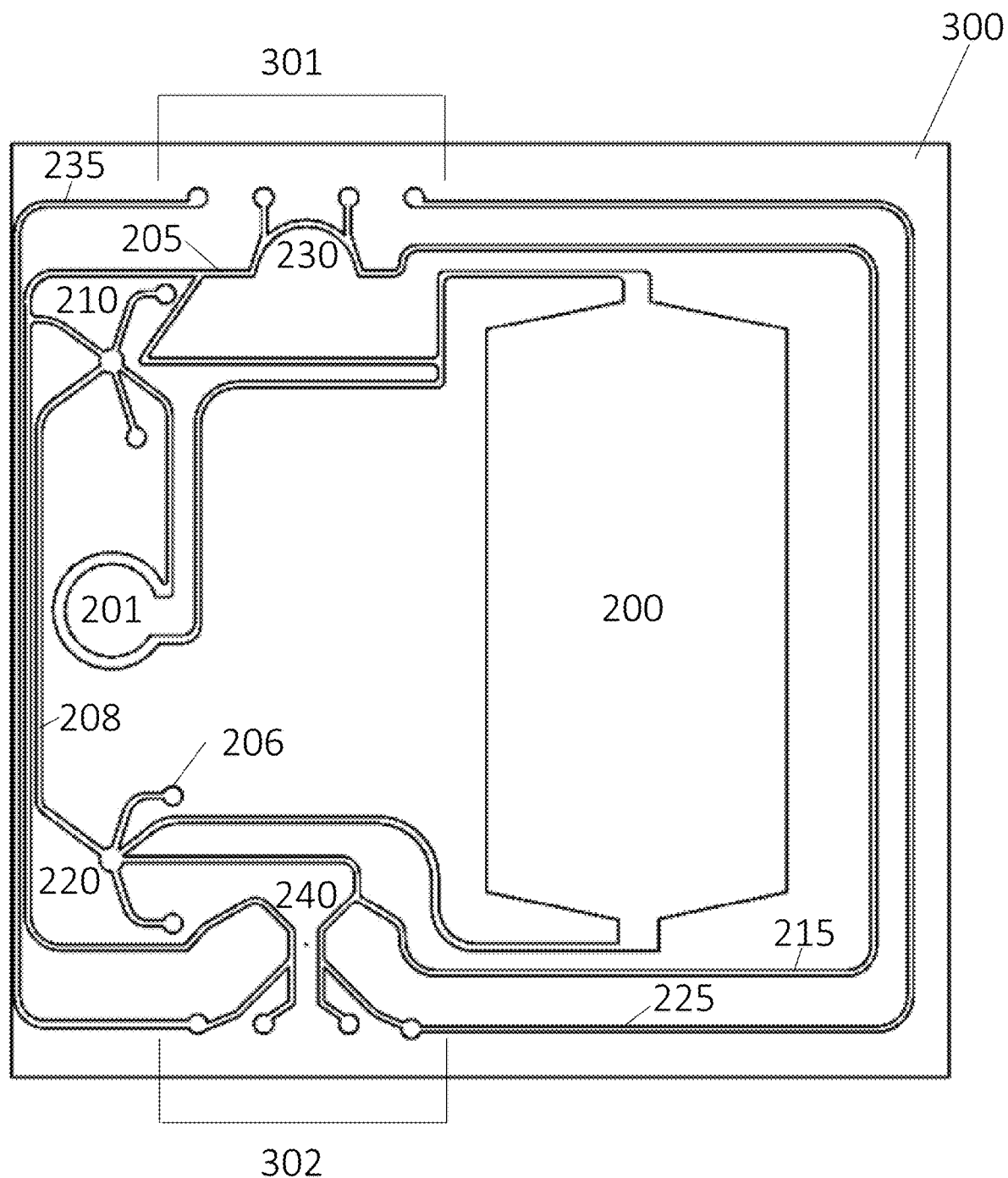
FIG. 3 shows schematically an IOM chip that is representative of an embodiment of a monolithic microfluidic chip according to one embodiment of the present invention.

FIG. 3 identifies the lines, pumps, valves, and connection busses in an IOM chip that is representative of an embodiment of a monolithic microfluidic chip 300 which could be used with a generic organ as part of an interconnecting Perfusion Controller and implement all of the capabilities described in FIG. 2A with a single microfluidic module, thereby being capable of controlling both the interconnects and the standard functions associated with an IOM Perfusion Controller. The organ 200 in this embodiment of the present invention is central to the device to facilitate imaging. The organ 200 is perfused by an imbedded pump 201 and input valve 210. Waste from the organ is routed to the output control valve 220 where it is either recirculated 208 or delivered to waste 206 or captured for further analysis. An input bus 301 and an output bus 302 are connected to an interface which allows this microfluidic chip to be connected to any other microfluidic chip of similar design.

Figure 4:
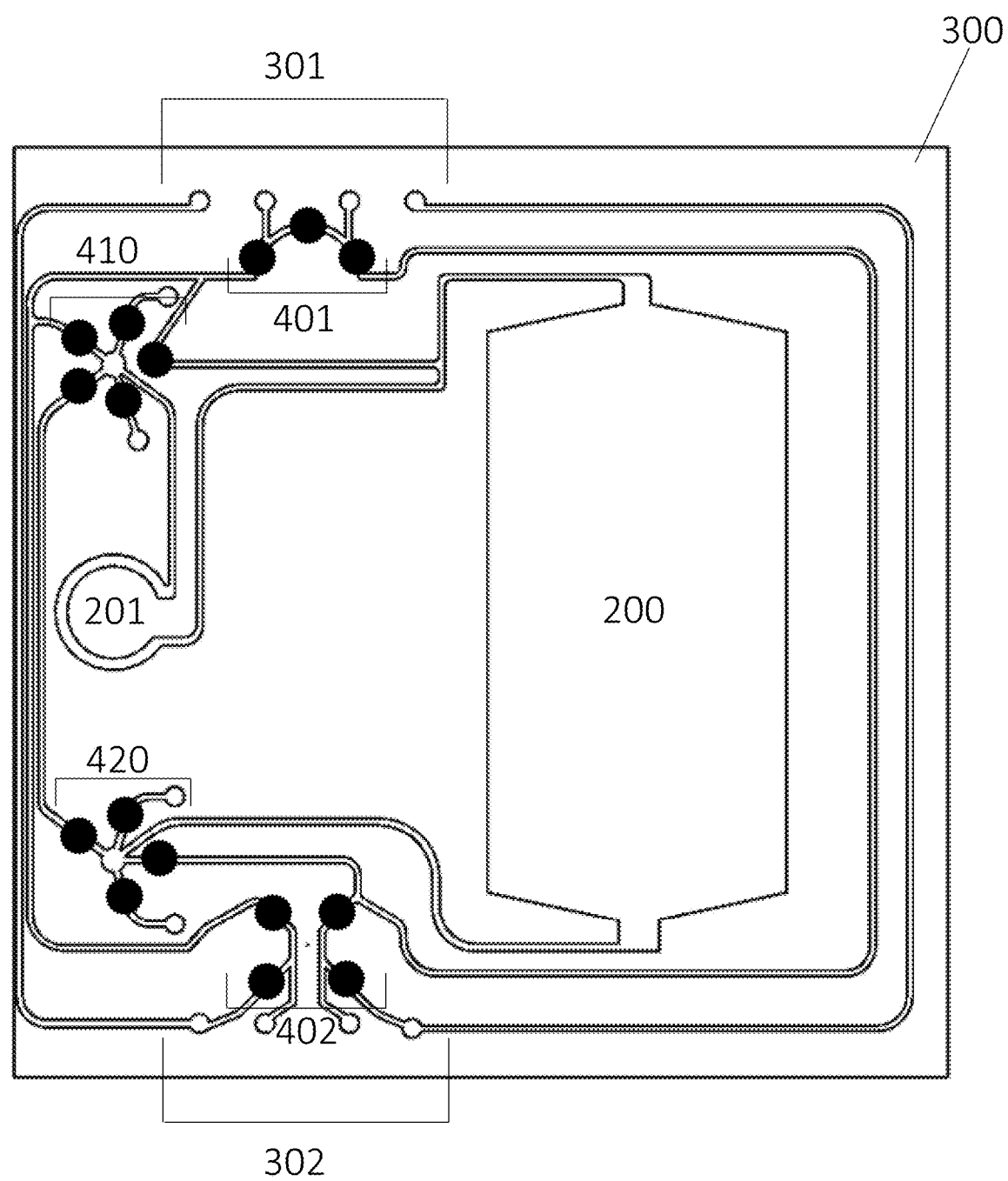
FIG. 4 shows the locations of the valve-actuating control points on a monolithic microfluidic chip according to one embodiment of the present invention.

FIG. 4 identifies in this embodiment of the monolithic microfluidic chip 300 the three control points 401 for the input bus 301, four control points 402 for the output bus 302, five control points 410 for the input control valve, and four control points 420 for the output control valve. Each of 401, 402, 410, and 420 represents an independent multiport valve, herein implemented as an RPV. In this drawing, all of these control points are shown as solid circles. As we will show later, in any particular configuration some of these control points will be open (open circles) and others will be closed (solid circles).

Figure 5:
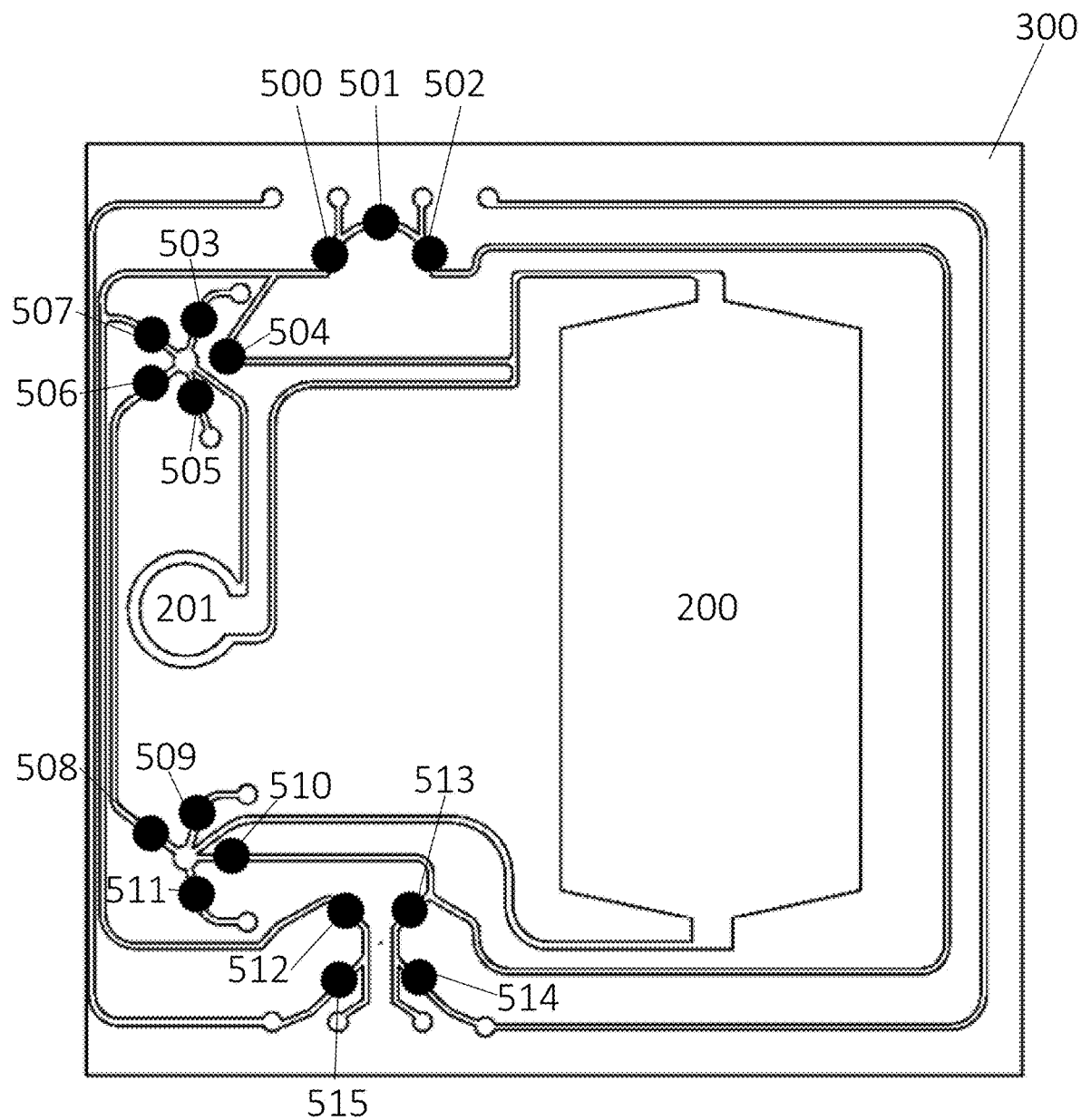
FIG. 5 shows an identification of each control point of each of the four valve systems embedded in the monolithic microfluidic chip according to one embodiment of the present invention.

FIG. 5 provides the identification as a solid circle of each control point (port) of each of the four valve systems 401, 402, 410, and 420 in FIG. 4 embedded in the monolithic microfluidic chip: control point 500 allows flow from the system's arterial bus to the on-chip arterial line; control point 501 allows direct connection between the arterial and venous on-chip bus lines; control point 502 allows flow from the system's venous bus to the on-chip venous line; control point 503 allows the input control valve to selectively obtain fluid from an off-chip reservoir of fresh media or other substance; control point 504 allows the input control valve to bypass the pump and allow the system's arterial line direct fluidic connection to the organ; control point 505 allows the input control valve to selectively obtain fluid from an off-chip reservoir of drug or other substance; control point 506 allows the input control valve to recirculate fluid from the organ, directly on-chip; control point 507 allows the input control valve to selectively pump fluid from the system's arterial line to the organ; control point 508 allows the output control valve to recirculate fluid from the organ, directly on-chip; control point 509 allows the output control valve to selectively deliver fluid to waste or other off-chip reservoirs; control point 510 allows the output control valve to selectively deliver fluid from the organ to the system's venous bus line; control point 511 allows the output control valve to selectively deliver fluid to sample analysis or other off-chip reservoirs; control point 512 facilitates connection between the output bus and the input bus arterial line and the output bus arterial line; control point 513 facilitates connection between the output bus and either the input bus venous line bypassing the organ or the output from the organ; control point 514 allows non-sterile waste to be flushed from the interconnect system; and control point 515 allows a sterilizing solution to be flushed across the interconnection bus ports. In this figure, all control ports are currently actuated (closed), while in practice, as shown below, some would be open and others closed.

Figure 6:
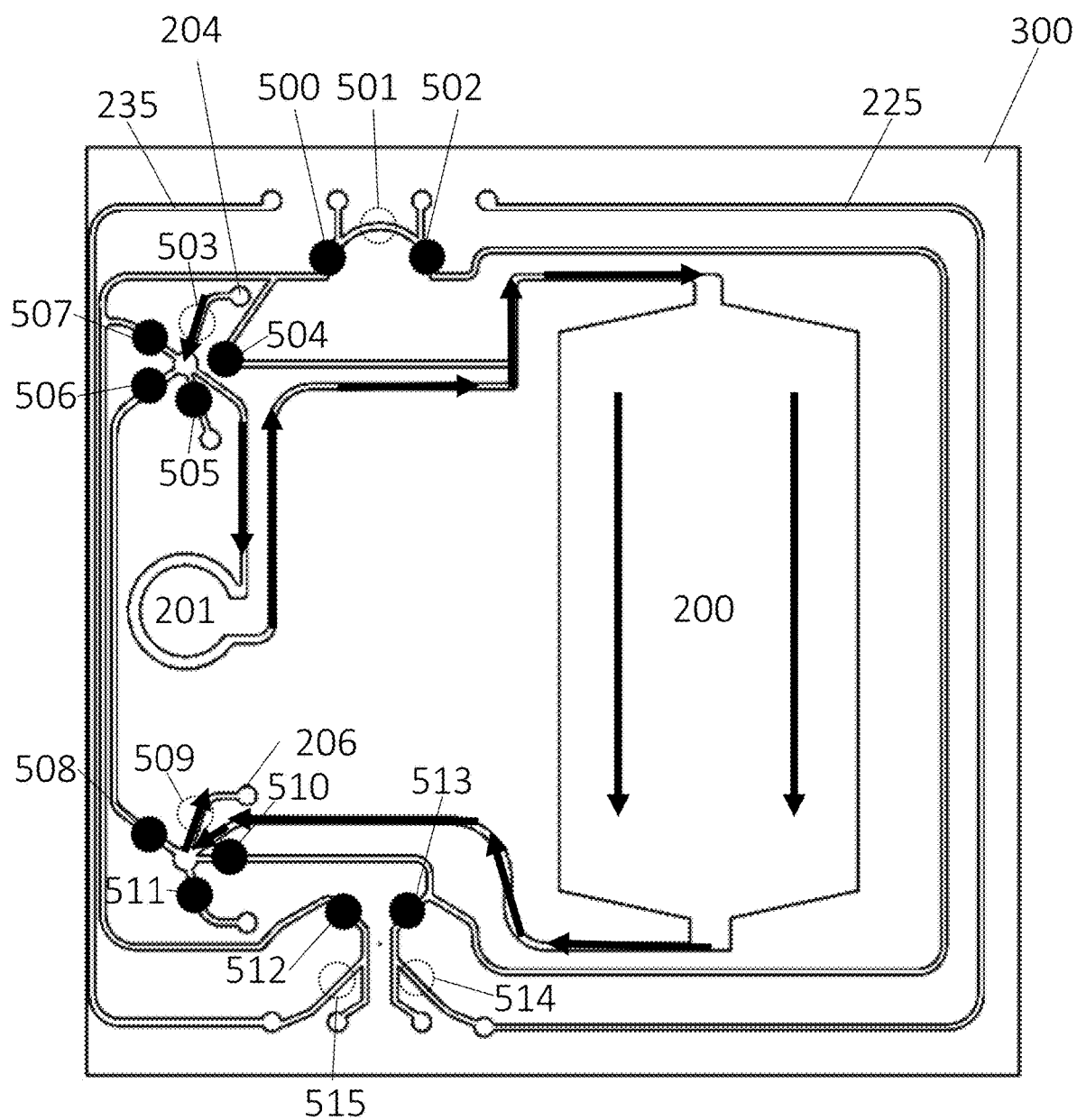
FIG. 6 shows the flow of fluids within the organ module when operating in the Isolated Organ Mode with media and waste coming from and going to external reservoirs according to one embodiment of the present invention.

FIG. 6 specifies the flow of fluids within the organ module 300 when operating in the Isolated Organ Mode. In this configuration, the input bus and output bus are isolated from the organ (control points/ports 500 and 502 are closed, blocking flow from an adjacent IOM). The arterial and venous input connections are shunted on the input side (control point/port 501, open), isolating the organ from the rest of the system, yet still allowing flow in an upstream IOM from the arterial side to the venous side via the shunt. In this configuration the organ can run independently from the system, and therefore can be removed or inserted into the system without altering the perfusion of the organ. The output bus has disabled connections to the organ's on-chip arterial and venous busses. The sterilize wash bus lines 515 and waste bus control ports 514 are open and allow connection to a small segment of the output arterial and venous interconnect lines, in preparation for sterilizing the lines. During operation in the Isolated Organ Mode, the five control points 503-507 for the input control valve, and four control points 508-511 for the output control valve can be adjusted as desired, i.e., the organ can be perfused by either fresh media (503, illustrated from port 204) or conditioned by a drug 505 or otherwise interfaced with off-chip reservoirs. The conditioned media post-organ can either be delivered to off-chip waste via (509, illustrated to port 206) or collected as an off-chip sample 511 for further analysis.

Figure 7A:
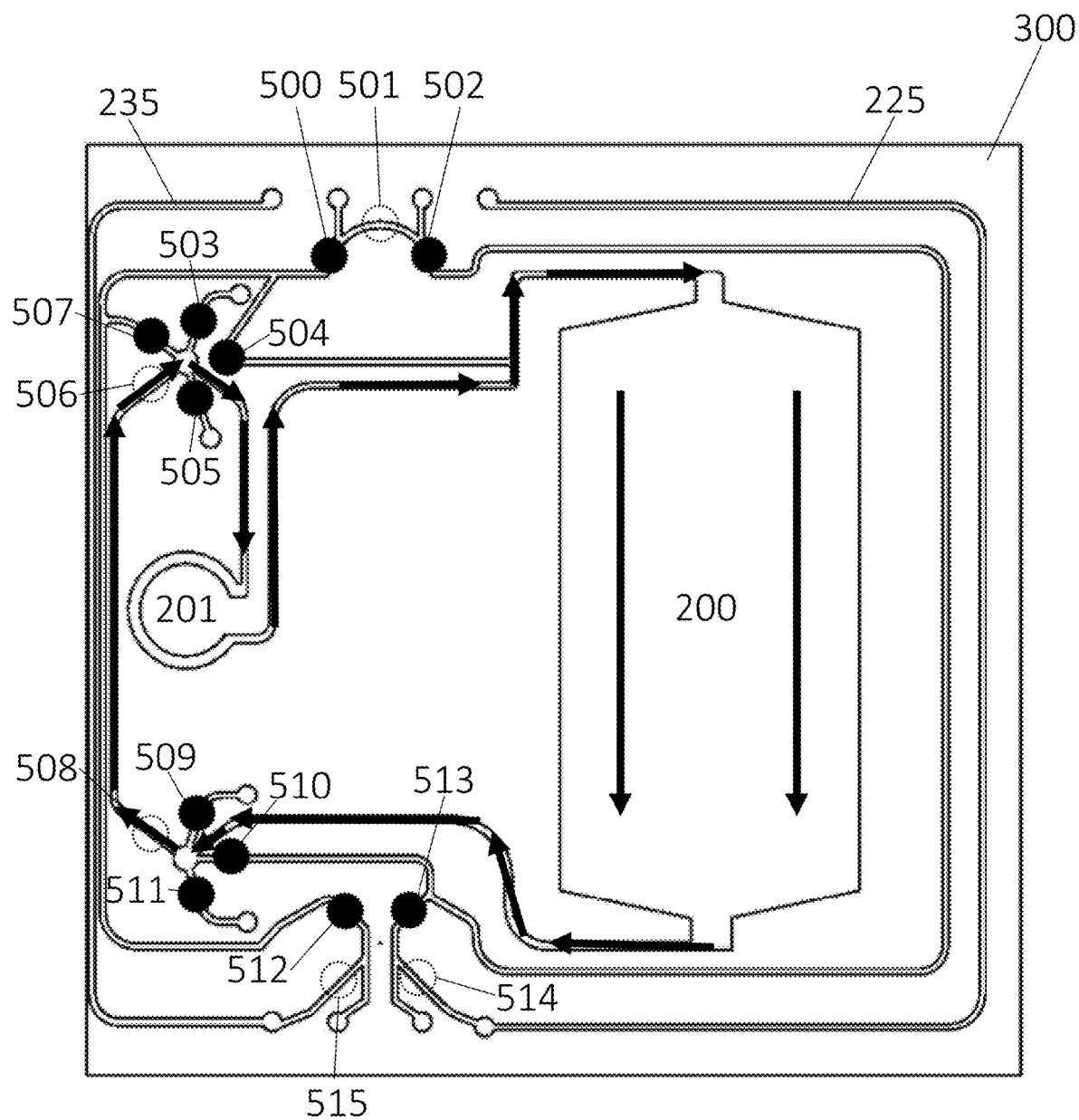
FIGS. 7A-7C show another variant of the Isolated Organ Mode in which the interconnects can be flushed while the organ is operating locally according to embodiments of the present invention.
Figure 7B:
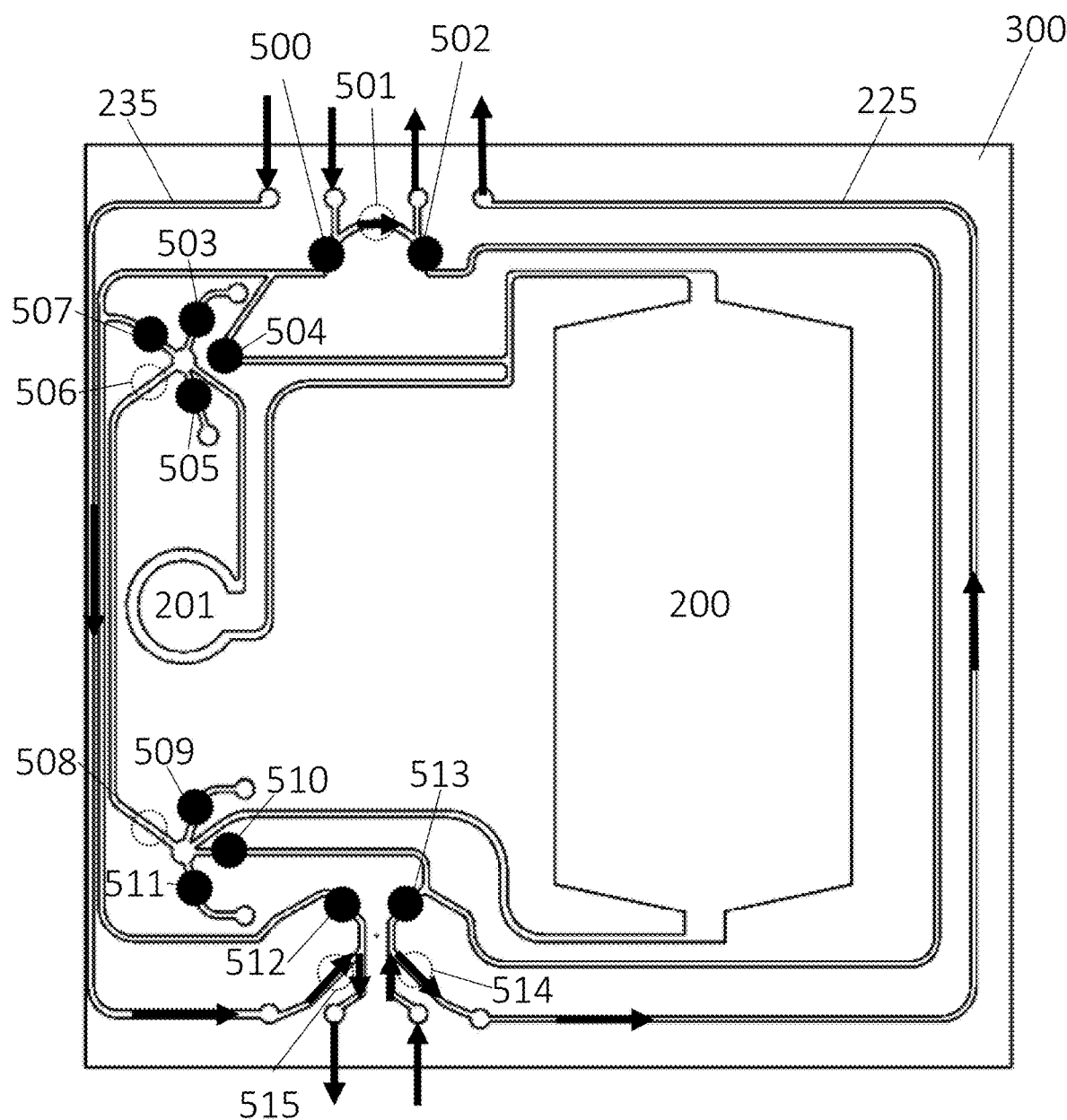
Figure 7C:
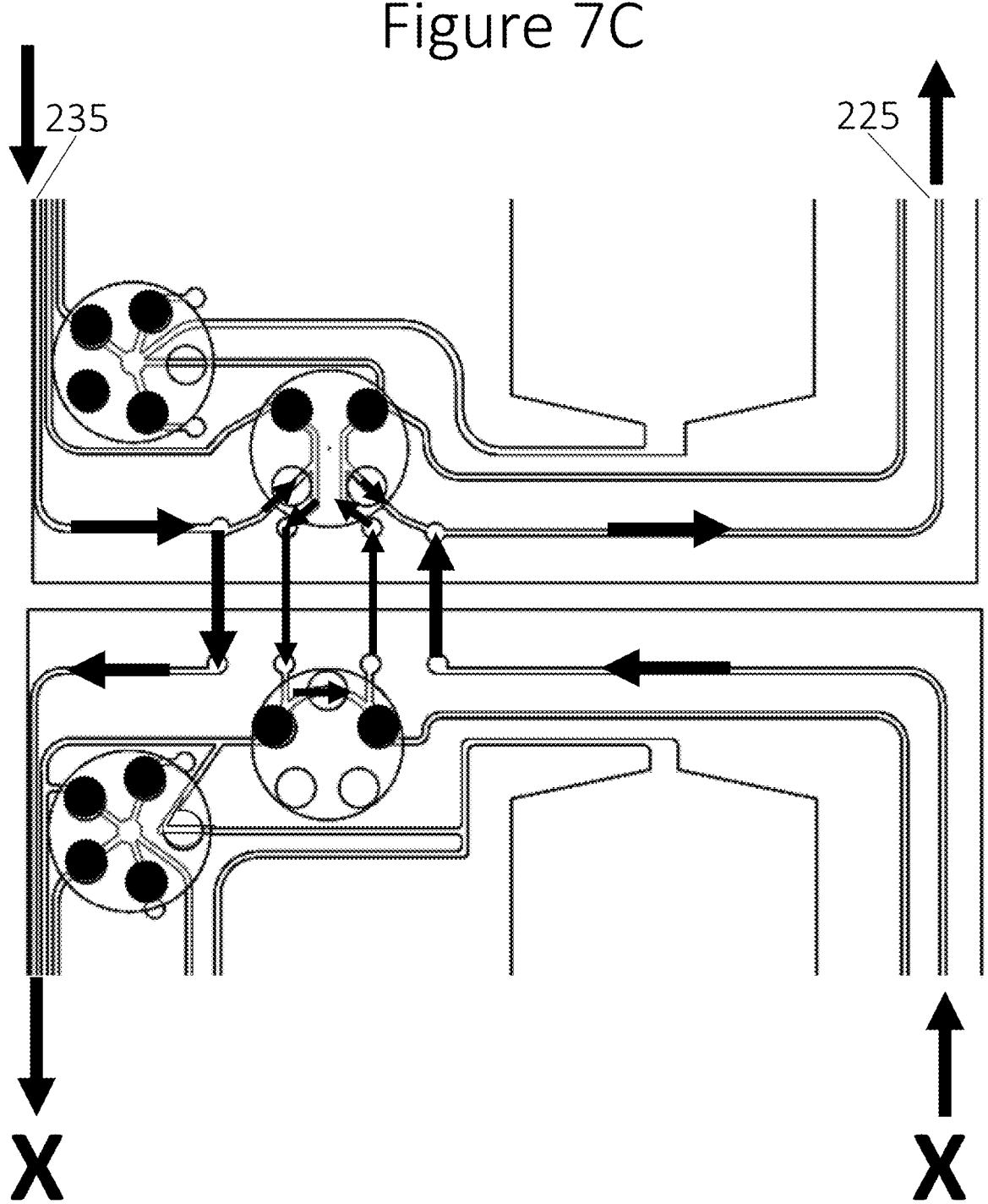

FIGS. 7A-7C show another variant of the Isolated Organ Mode in which the interconnects can be flushed while the organ is operating locally with on-board recirculation. In this configuration, the input bus and output bus are isolated from the organ (control points/ports 500 and 502 are closed, blocking flow). The upstream arterial and venous input connections are shunted on the input side (control point/port 501, open), isolating the organ from the rest of the system, yet still allowing flow from the arterial side to the venous side of upstream organs via the shunt. In this configuration the organ can run independently from the system, and therefore can be removed or inserted into the system without altering the perfusion of the organ. The output bus has disabled connections to the organ's on-chip arterial and venous busses. The sterilize wash bus valve 515 and the waste bus valve 514 isolate the small segment of the output arterial and venous lines that would be otherwise be blocked by control point 501, in preparation for sterilizing the lines by passing sterilant/rinse media down the wash line 235 and the waste line 225.

The organ can be perfused by either fresh media (503, illustrated) or conditioned by a drug (505) or otherwise interfaced with off-chip reservoirs.

The conditioned media post-organ can either be delivered to off-chip waste via control point/port 509, or collected as an off-chip sample (511) for further analysis.

In this specific configuration, the organ is set to recirculate its fluid for organ conditioning. The input control valve is set to allow flow from the recirculation line 506. The output control valve is set to deliver fluid from the organ back to the input control valve via control port 508.

While the organ is being recirculated internally, this valve configuration enables the flow of sterilizing and washing fluids through the interconnects between sequential organ modules, as shown by the fluid flow arrows in FIG. 7B. The sterilize/wash valve 515 and the waste valve 514 are used to connect the sterilize/wash line 235 and the waste line 225 to a small segment of the output arterial and venous lines that would otherwise be blocked by valve 501, thereby allowing the flow of sterilizing and rinsing fluids through the interconnects and then into the waste line in preparation for sterilizing and then washing the interconnects.

FIG. 7C illustrates how these flows move between two adjacent modules. The wider arrows indicate the faster flows down the entire wash line 235 and the entire waste line 225, while the thinner lines represent the flows through an individual interconnect. Note that the connecting organ could have the wash and waste lines occluded downstream (X) to promote flow across the newly made connection, unless the system has sufficient flow and pressure to allow multiple organ interconnects to be washed in parallel.

Figure 8:
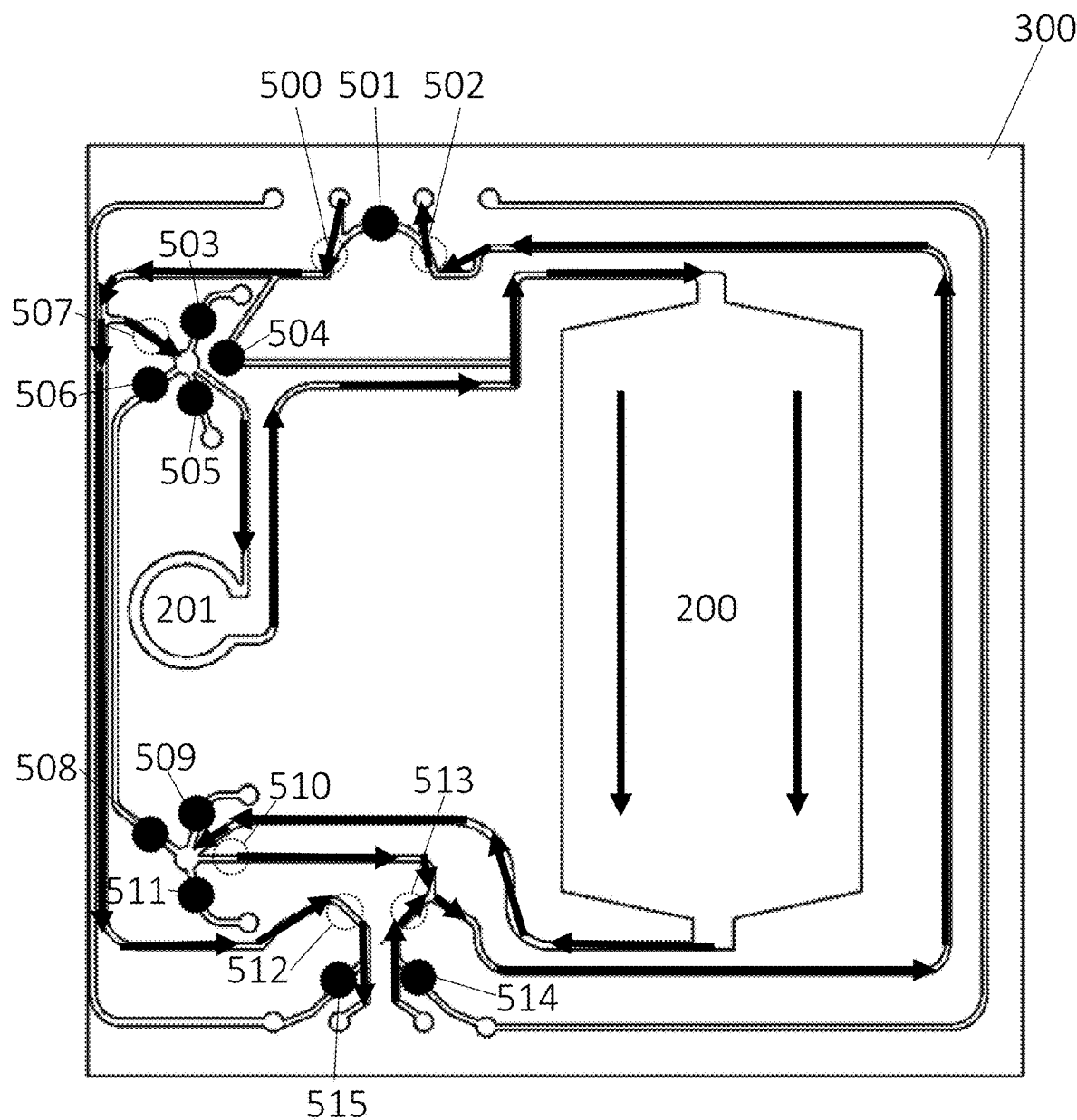
FIG. 8 shows the valve configuration for coupling multiple organs or other modules together with common, parallel perfusion according to one embodiment of the present invention.

In order to couple multiple organs or other modules together with common, parallel perfusion, the valves can be configured as shown in FIG. 8. The organ is perfused from the arterial bus, by means of the on-board pump 201. In this configuration, the interconnect input bus is set to allow the organ to receive fluid from the arterial bus 500 and deliver fluid to the venous bus 502. Control point/port 501 is closed.

The input valve is set to draw fluid from the arterial bus via open port 507. Fluid from the arterial bus is pumped through pump 201 and into the organ 200. On-chip arterial bus line fluid is also delivered to the output interconnection bus via open port 512.

The fluid exiting the organ is routed through the output control valve through port 510 to the venous bus line where it is mixed with fluid from the system's venous bus (control port 513, open) and is returned to the upstream organ through the input interconnect bus (flow is upward in this line).

Figure 9:
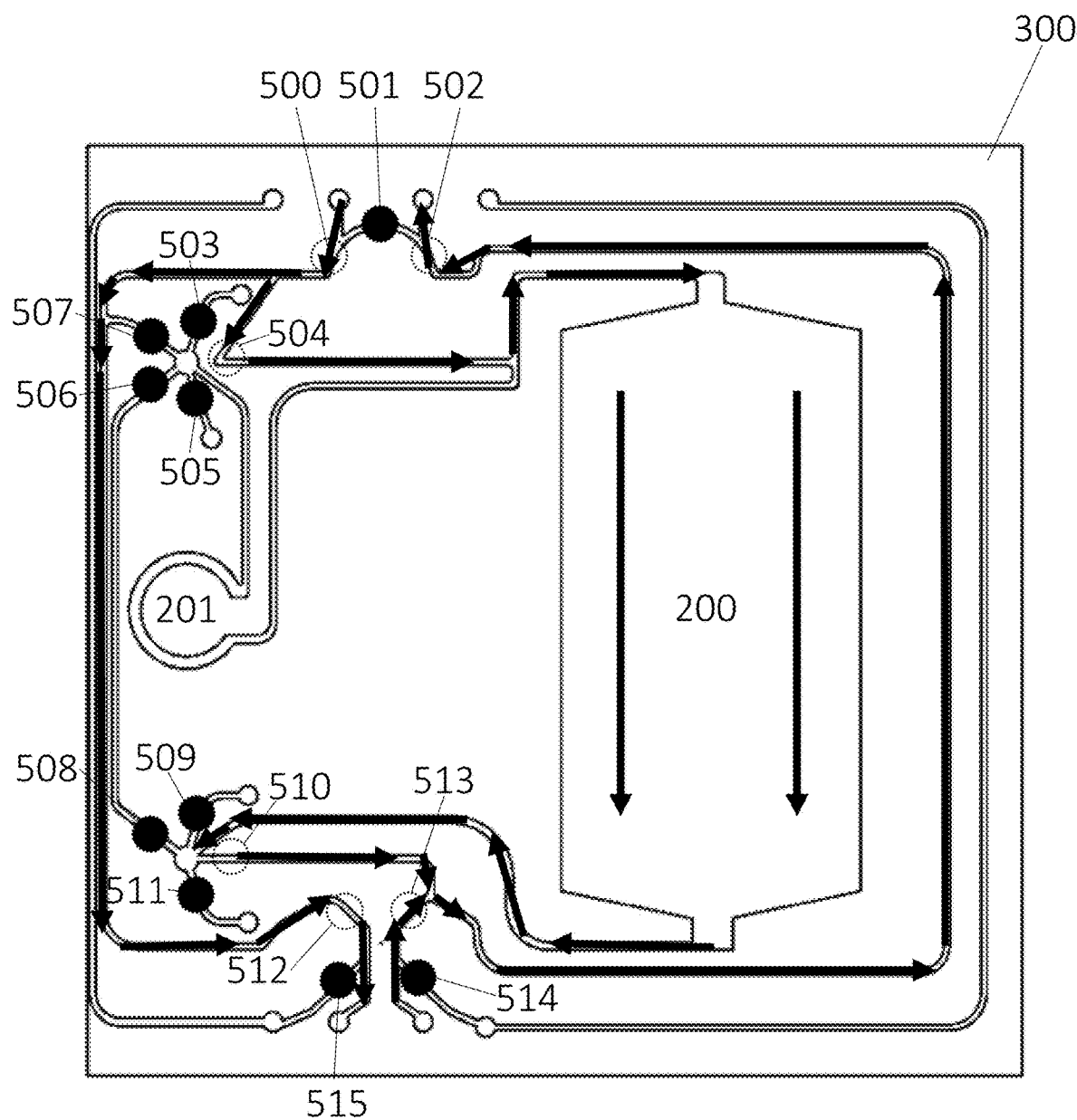
FIG. 9 shows how an organ can be perfused directly from the arterial side, off pump, and using the pressure in the arterial line to drive fluid through the organ according to one embodiment of the present invention.

FIG. 9 shows how an organ can be perfused directly from the arterial side, off pump, and using the pressure in the arterial line to drive fluid through the organ. In this configuration, the interconnect input bus is set to allow the organ to receive fluid directly from the arterial bus 500 and deliver fluid to the venous bus 502. Control port 501 is closed.

The input valve is set to draw fluid directly from the arterial line via port 504, thus bypassing the pump. On-chip arterial line fluid is also delivered to the output interconnection bus via open port 512. For this to function properly, the pressure in the arterial line 500 must be sufficient to drive perfusion through the organ 200.

The fluid exiting the organ is routed through the output control valve through port 510 to the venous bus line where it is mixed with fluid from the system's venous bus (513, open) and is returned to the upstream organ through the input bus (flow is upward in this line).

Figure 10:
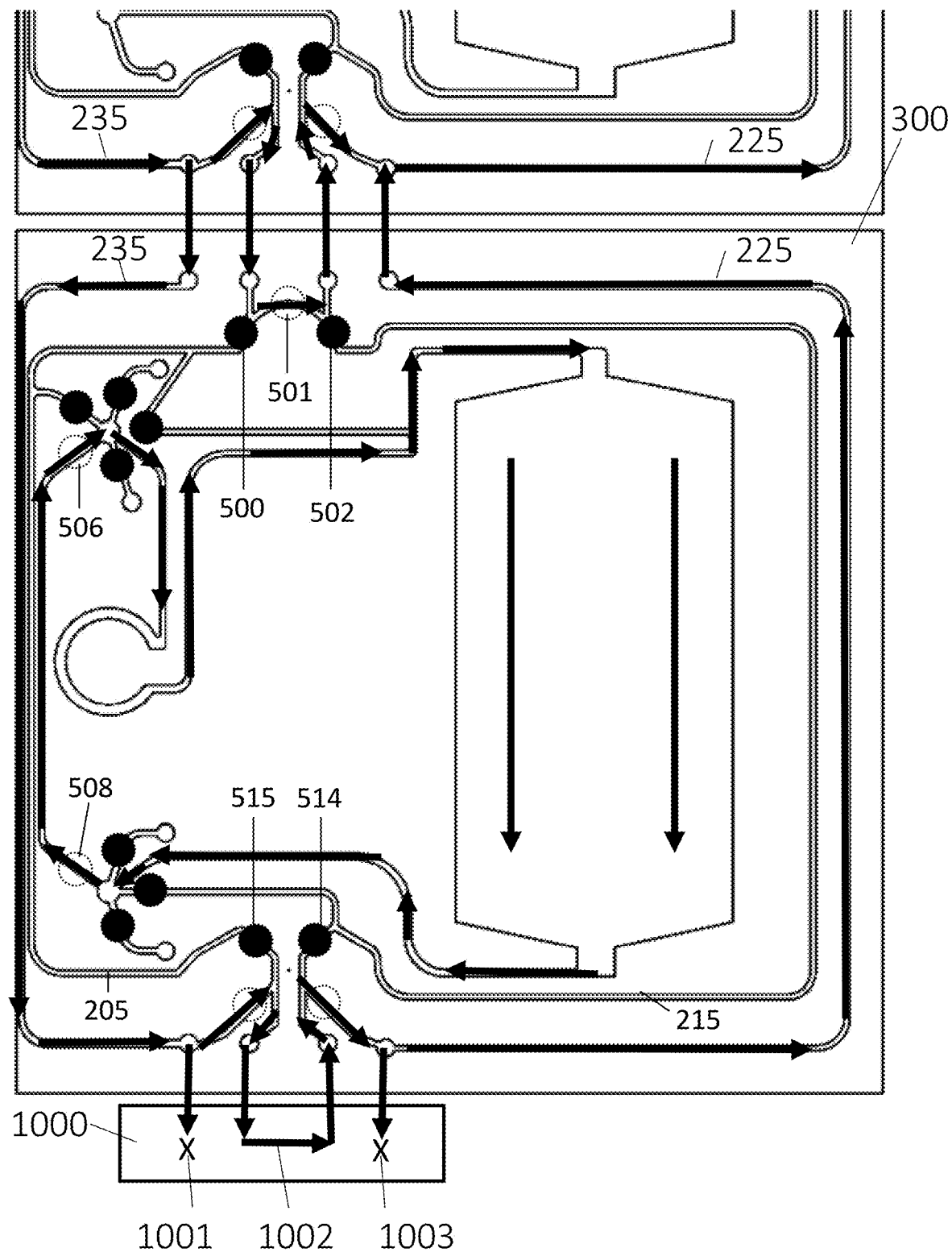
FIG. 10 shows steps to initialize organ connection in the Sterilize/Wash Mode while using Internal Recirculation according to one embodiment of the present invention.

FIG. 10 presents the first step in the sequence of events required to connect organs. The steps to initialize organ connection are as follows: (1) each organ, set in Organ Isolation Mode, is connected together; (2) sterilizing solution from the wash line is pumped into each interconnected Perfusion Controller from an upstream module; and (3) waste is returned to the upstream module via the internal waste bus.

This configuration will allow sterilization wash solution to be pumped across the newly formed interface between organ N-1 and organ N. A terminal cap 1000 applied to the final interconnected Perfusion Controller allows the arterial and venous bus lines to be bridged by a bridge 1002 and successfully sterilized in this embodiment. The bridge 1002 can be selectively disengaged. The wash and waste lines are occluded by controls 1001 and 1003, respectively.

In this configuration, the input bus and output bus are isolated from the organ (control ports 500 and 502 are closed, blocking flow). The arterial and venous input connections are shunted on the input side (control port 501 is opened), isolating the organ from the rest of the system, yet still allowing flow from the arterial side to the venous side via the shunt. In this configuration the organ can run independently from the system, and therefore can be removed or inserted into the system without altering the perfusion of the organ. The output bus has disabled connections to the organ's on-chip arterial and venous busses. The sterilize wash bus line 515 and waste bus line 514 are connected to a small segment of the output arterial and venous lines 205 and 215, in preparation for sterilizing the lines.

In this specific configuration, the organ is set to recirculate its fluid for organ conditioning. The input control valve is set to allow flow from the recirculation line 506. The output control valve is set to deliver fluid from the organ back to the input control valve via control port 508.

Figure 11:
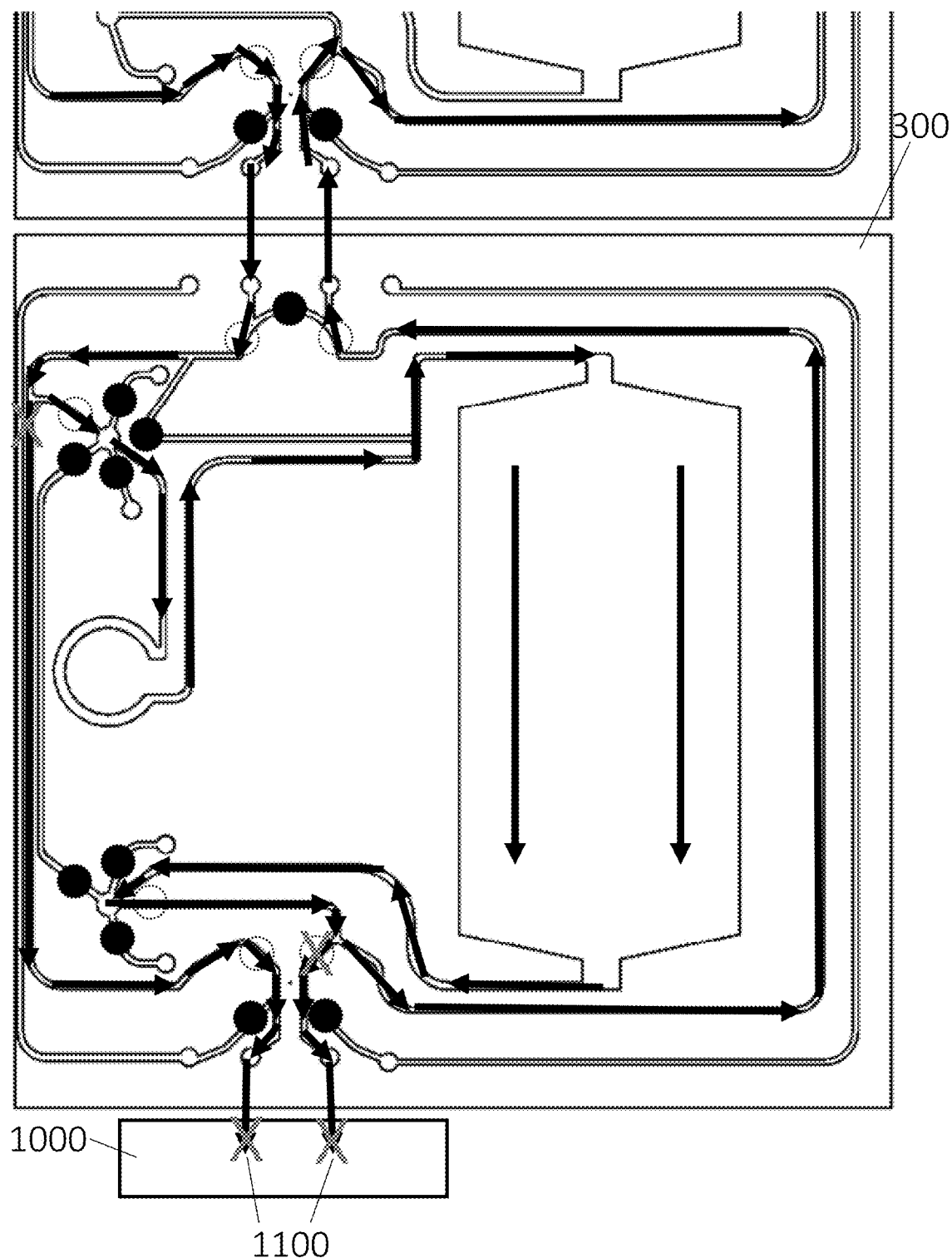
FIG. 11 shows the fluid flows in the last organ of a series operating in the Run Organ in Arterial/Venous Mode according to one embodiment of the present invention.

FIG. 11 shows the fluid flows in the last organ of a series operating in the Run Organ in Arterial/Venous Mode. In this configuration, the organ can sample from the arterial line and its conditioned fluid returns to the system's venous bus. All ports of the output bus are occluded by the output bus cover 1000 and the shunt between the arterial and venous ports is closed by stoppers 1100.

Figure 12:
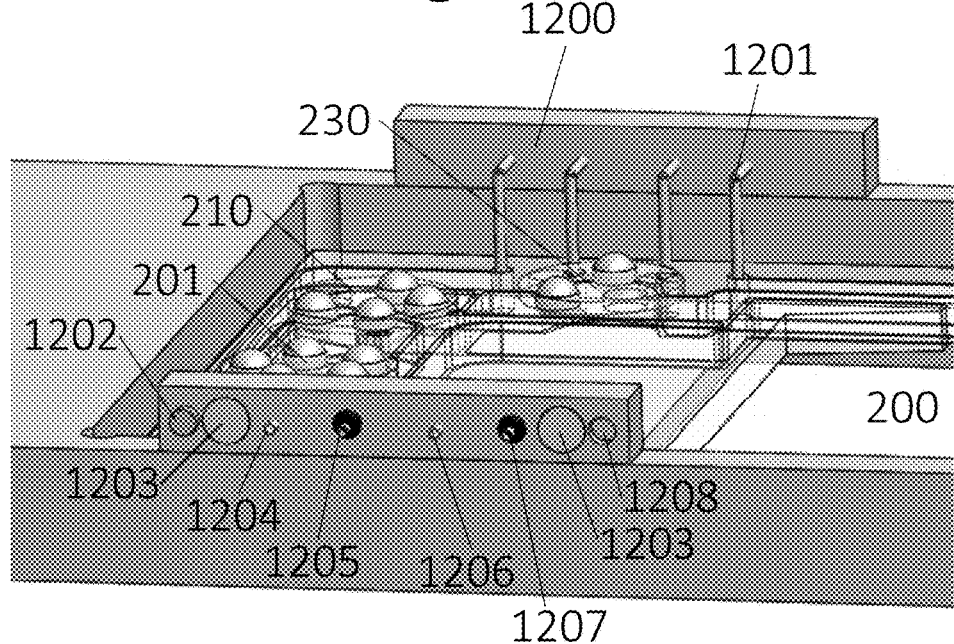
FIG. 12 shows a three-dimensional rendering of the interconnect system mounted on the sides of an IOM module according to one embodiment of the present invention.

FIG. 12 shows a three-dimensional rendering of the interconnect system mounted on the sides of an IOM module as one embodiment of the present invention, in which the connection busses 1200 of each interconnecting model, interfaced to the monolithic microfluidic chip via tubing 1201, mates in tandem with each other via alignment pin 1202 and receptacle 1208 and magnet pairs 1203. In another embodiment, the alignment pins could provide electrical power for driving any on-module pumps, valves, or electronics.

The connection busses 1200 contain fluidic connections for wash line 1204, arterial line 1205, venous line 1206, and waste line 1207. O-rings are presented in some embodiments for facilitating sealing of the fluidic connection, as shown on connection ports 1205 and 1207. In the exemplary embodiment, the interconnect system comprises, among other things, the following components: at least one input and output bus connector interconnection interface 1200, at least one tubing connection from monolithic microfluidic chip to interconnection interface 1201, at least one upstream interconnection bus control valve 230, at least one input control valve 210, at least one pump 201, at least one alignment and charging pin 1202, at least one N/S magnet pair to aid in connection and alignment 1203, at least one wash line 1204, an arterial line with O-ring connection seal 1205, at least one venous line 1206, and at least one waste line with O-ring connection seal 1207.

Note that the connections shown in FIG. 12 could be modified to provide interconnects with a larger number of fluid pathways, for example individual organ-organ connections such as those which occur between the intestine and the liver, the liver bile duct and the stomach, or connections that form a line that would allow drugs to be delivered to specific organs from a MicroFormulator that is connected to the system but not immediately adjacent to the organ in question.

Similarly, the interconnects could provide electrical power, compressed air, or other organ supporting elements that might need to be passed from organ to organ or shared between organs.

In certain embodiments, there is a shared line for sample collection. An analytical fluid collection line could be used where sampling is done from each organ. The ion mobility-mass spectrometry (IM-MS) or electrochemical sensor connections can be made at the MicroClinical Analyzer which is part of the interconnected system of modules. Thus the basic interconnect system technology shown in the present invention could easily be extended to include numerous types of analytical instrumentation and control modules suitable for monitoring and stabilizing multi-organ or multi-tissue construct bioreactor systems. A key advantage of this approach is that it allows the wash, arterial, venous, and waste channels to be placed around the circumference of each microfluidic chip for an IOM module, such that the interconnects are realized simply by mounting the interconnect unit and its tubing to prepunched holes on either end of the microfluidic chip.

Figure 13:
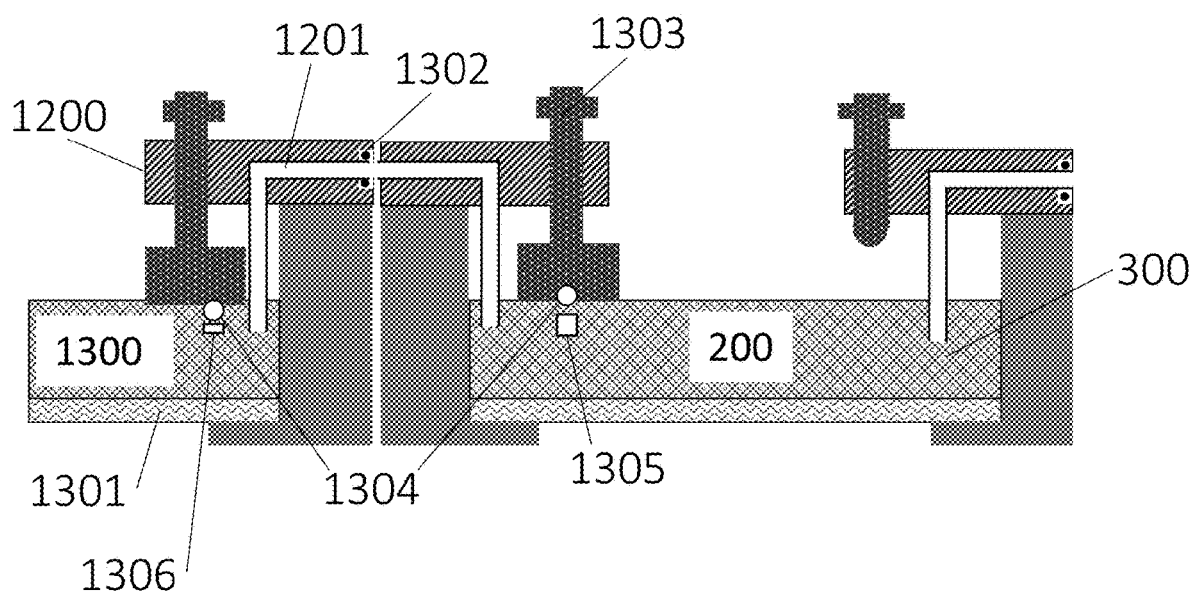
FIG. 13 shows a cross-section of an interconnect system connecting two IOMs according to one embodiment of the present invention.

FIG. 13 shows a cross-section of an interconnect system connecting two IOMs. The upstream organ 200 and its integrated monolithic microfluidic 300 are connected fluidically by interface tubing 1201 and connection busses 1200 to the downstream organ, organ N-1, 1300. Both organs have glass coverslips 1301 beneath them to facilitate imaging of the organs throughout the experiment. Sealing O-rings 1302 ensure that a gas- and water-tight connection is formed between the upstream and downstream organs. Interconnection bus control valve knobs 1303 allow manual operation of the interconnection bus valves. In this embodiment, upstream and downstream valves compress a rigid ball 1304 into an elastomeric channel, thus leaving channel 1305 open and channel 1306 closed.

Figure 14:
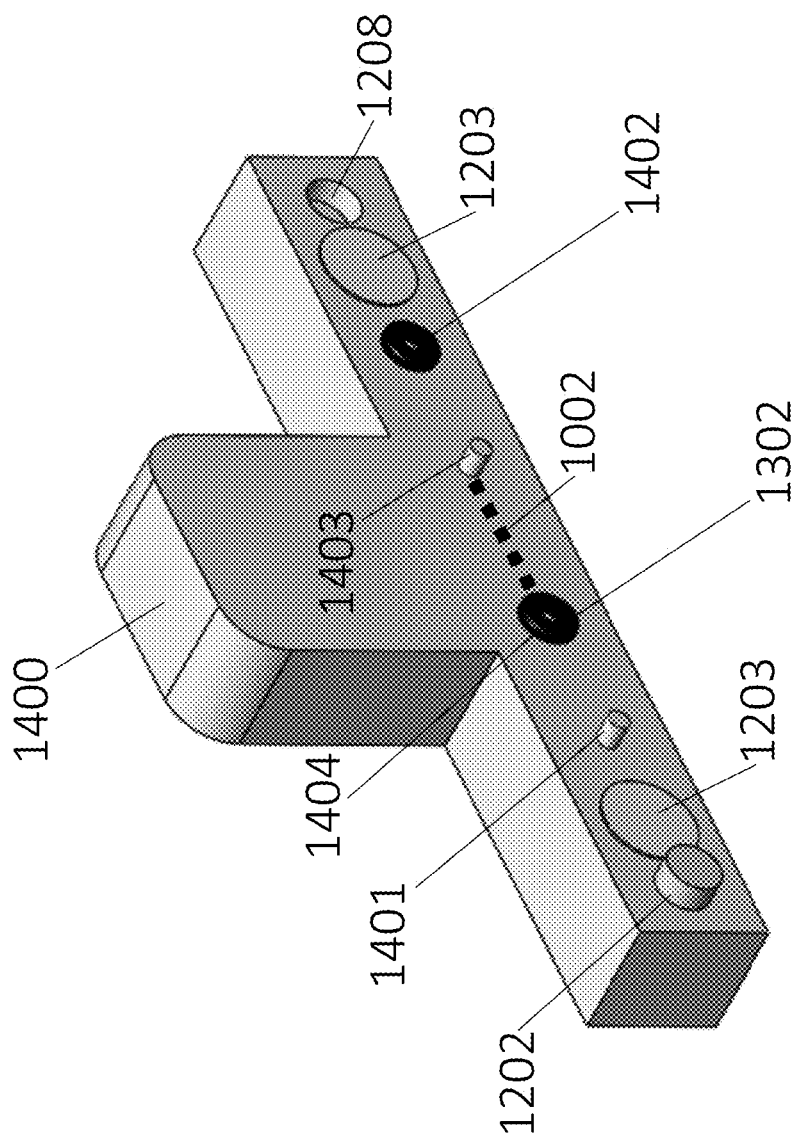
FIG. 14 shows an interconnection cover that terminates a line of IOMs according to one embodiment of the present invention.

FIG. 14 shows an interconnection cover 1400 that terminates a line of IOMs. Alignment pin 1202 fits into an opposite alignment hole on the upstream organ. The cover's alignment hole 1208 fits into the upstream organ's interconnection alignment pin. Magnets 1203 facilitate alignment and attachment. A flow stopping peg 1401 terminates the waste line of the upstream organ via its O-ring or similar washer. Similarly, the downstream wash line is occluded by a rubber stopper 1402. An O-ring 1302 prevents fluid leakage during the operation of the system. The upstream organ's arterial line's flow is routed through the interconnection cover via a tubing port 1403. This port can be connected to the upstream organ's venous line 1404 via internal tubing 1002 or selectively occluded.

Figure 15:
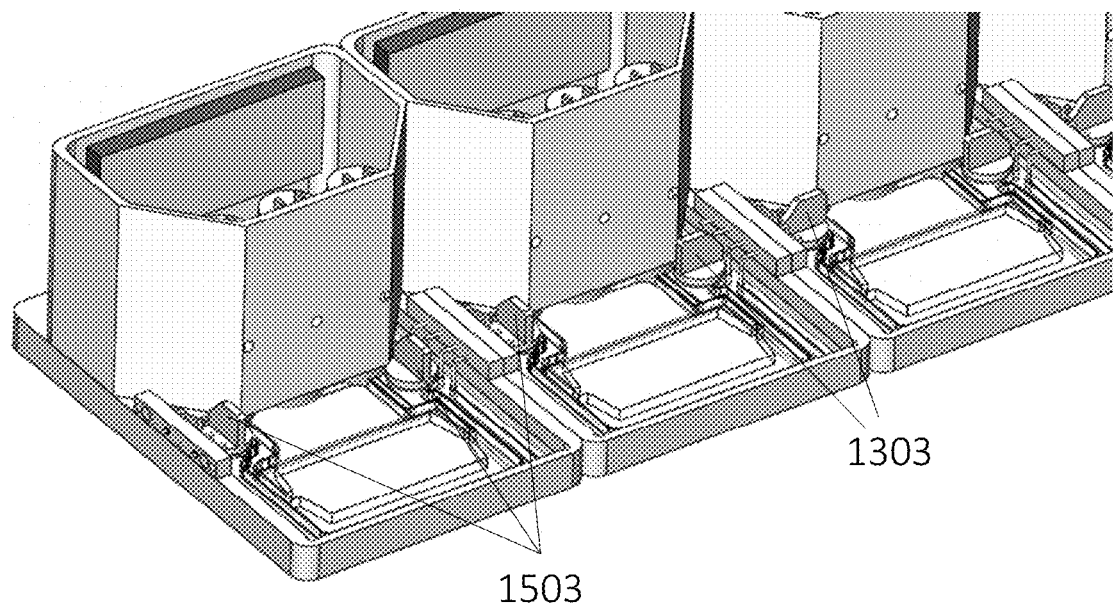
FIG. 15 shows multiple interconnecting organ Perfusion Controllers according to one embodiment of the present invention.

FIG. 15 shows multiple interconnecting organ Perfusion Controllers. Fluidic interface between the organs is controlled by interconnection bus control valve knobs 1303. An interconnection cover is required to complete the fluidic circuit. In certain embodiments, interconnect covers do not require the shunt (bridge 1002 as shown in FIG. 10) within the cover. Note that in the leftmost module three control knobs 1503 are set to the Sterilize/Wash Mode to sterilize the interconnects of the leftmost module, whereas upstream control knobs 1303 are set in the Run position.

Figure 16:
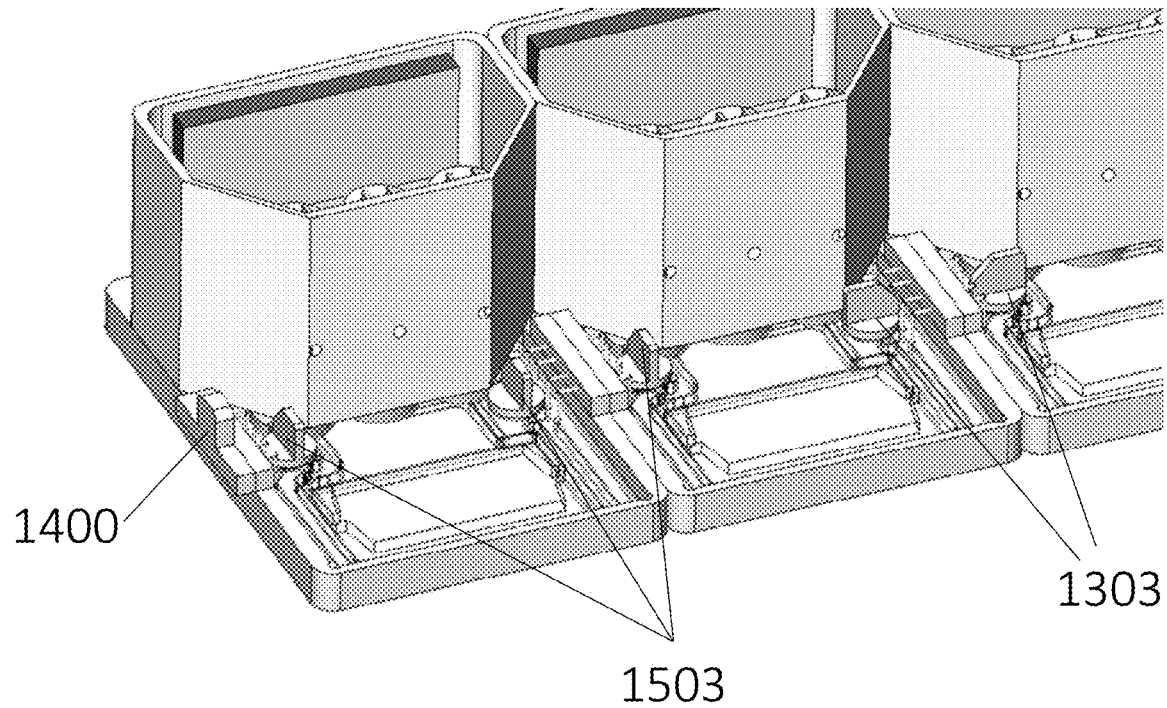
FIG. 16 shows a view of the terminal cover required for proper operation of the interconnection sterilization procedure and termination of the arterial and venous busses according to one embodiment of the present invention.

FIG. 16 provides a view of the terminal cover required for proper operation of the interconnection sterilization procedure and termination of the arterial and venous busses. The interconnection cover 1400 can selectively enable or disable flow across the arterial and venous bus lines during normal operation of the system. During sterilization, the terminal cover allows the wash and waste lines to be connected at the distal end of the system, thus enabling sterilization wash solution to flow throughout the entire system and sterilize any new module-to-module connections, with excess fluid entering the waste line and being flushed out of the system.

Figure 17:
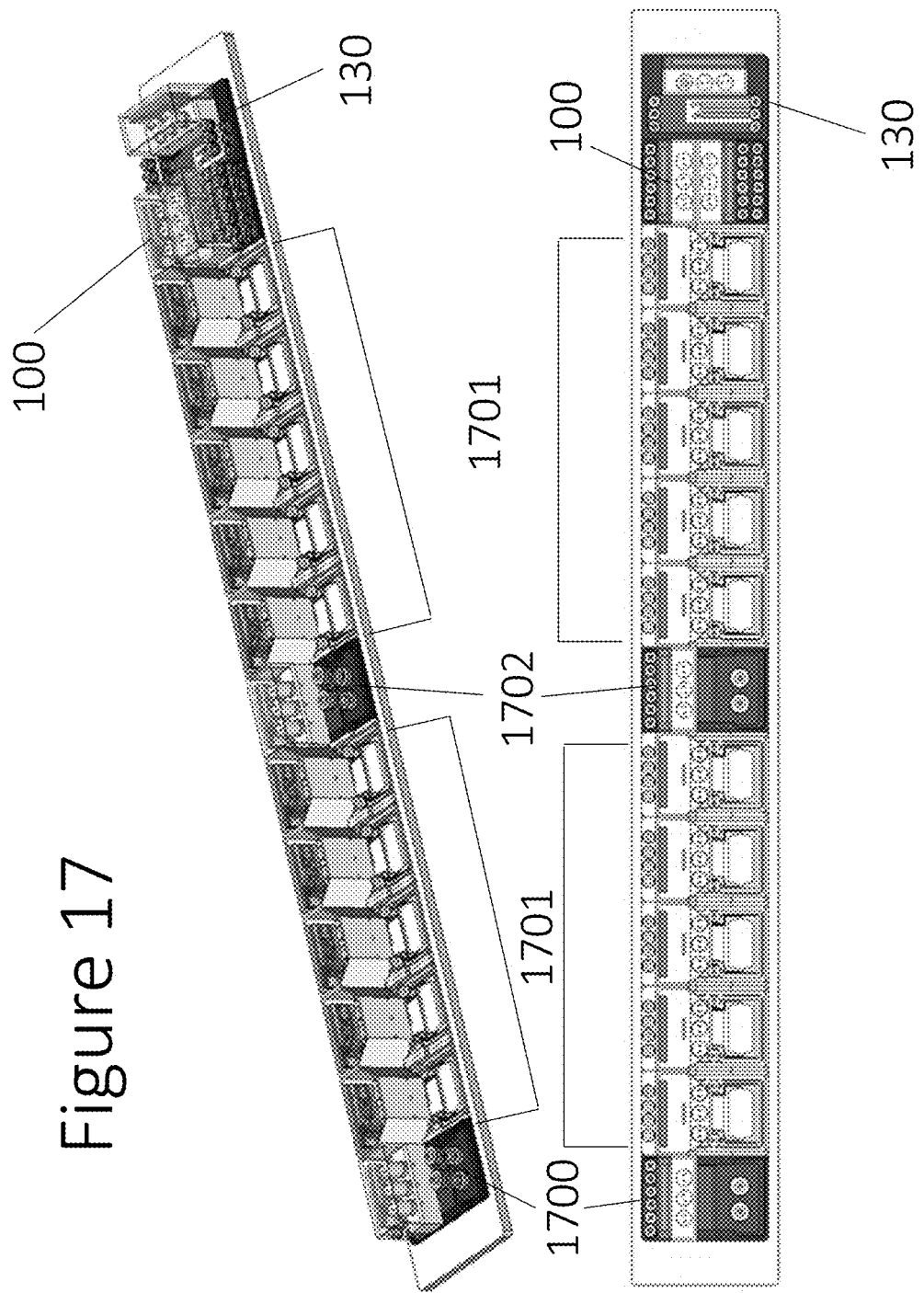
FIG. 17 shows a system-level view of a fully populated tray of IOM modules according to one embodiment of the present invention.

FIG. 17 is a system-level view of a fully populated tray of IOM modules according to one embodiment of the present invention. From the left, the first module 1700 provides sterilization, wash and waste operations and reservoirs. The next five modules 1701 are for organs. The seventh module is a Cardiopulmonary Assist Module 1702, followed by five more organ modules 1701, MicroFormulator 100, and the MicroClinical Analyzer 130.

The interconnection module 1700 drives fluid through the wash and waste busses. The Cardiopulmonary Assist Module 1702 drives fluid through the arterial and venous busses, oxygenates the media, and removes excess carbon dioxide. These modules are in turn connected to Perfusion Controllers 1701, a MicroFormulator 100, and a MicroClinical Analyzer 130. The interconnection module 1700 contains the pump and valve systems for properly rinsing newly interconnected organs introduced to the system and controlling arterial and venous flow. Multiple interconnecting organ Perfusion Controllers 1701 are sterilized by these upstream modules 1700. A MicroFormulator 100 is connected to replace any hormones, growth, or signaling factors required by the system. A MicroClinical Analyzer 130 is also present in this system to analyze samples from the organ Perfusion Controllers. In this embodiment, these custom delivery and analysis modules are able to communicate fluidically via bus lines with the connected Perfusion Controllers 1701.

Figure 18A:
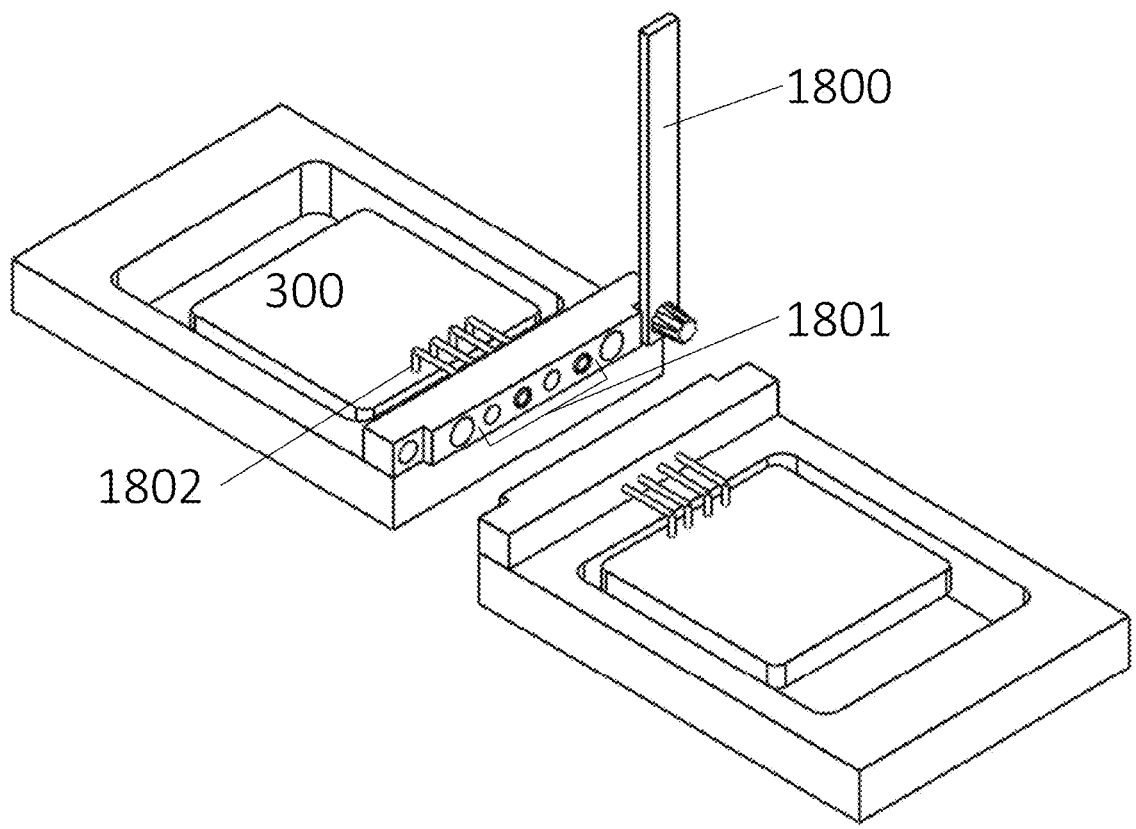
FIG. 18A shows ports having a rotating covers that can minimize the risks of contamination, fluid loss, and introduction of air bubbles for IOM modules that are not connected to another module through the interconnect system according to one embodiment of the present invention.

As shown in FIG. 18A, the interconnect system can have a rotatable port cover 1800 that minimizes the risks of contamination, fluid loss, and introduction of air bubbles for TOM modules, e.g., TOM module 300 shown in FIG. 18A, that are not connected to another module through the interconnect system, for example while a module is being handled or transferred from one work station to another. Separate, unattached covers (not shown) could also be used, but run the risk of being contaminated or lost. As shown in FIG. 18A, the rotatable port cover 1800 is disposed between a left-hand side (first) interface and the right-hand side (second) interface, retractably attached to an end portion of the first interface, and operably rotating between a close position (FIG. 18E) and an open position (FIG. 18A) along a rotation direction parallel to the second surface of the first interface. The rotatable port cover 1800 can also serve as a magnet separator. The shape of the groove 1804 and the mating surface 1810 (FIGS. 18C and 18D) can be designed such that the cover retracts upon opening so that edge of the TOM is not obstructed by the rotatable port cover 1800 when the rotatable port cover 1800 is in an open position, as shown in FIG. 18A. The proper choice of magnet pairs can assure that a single design of the rotatable port cover can fit either the left- or right-hand ports of the TOM interconnect. The role of the cam-actuated rotating cover is to separate the magnets that connect a pair of IOMs. In this embodiment, fluidic interface ports 1801 interface to the TOM 300 via tubing connection ports 1802.

Figure 18B:
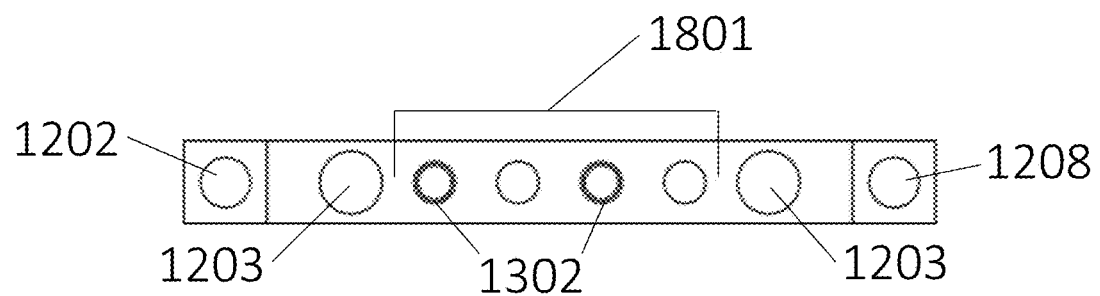
FIG. 18B shows an end view of the tubing connection interface according to one embodiment of the present invention.
Figure 18:
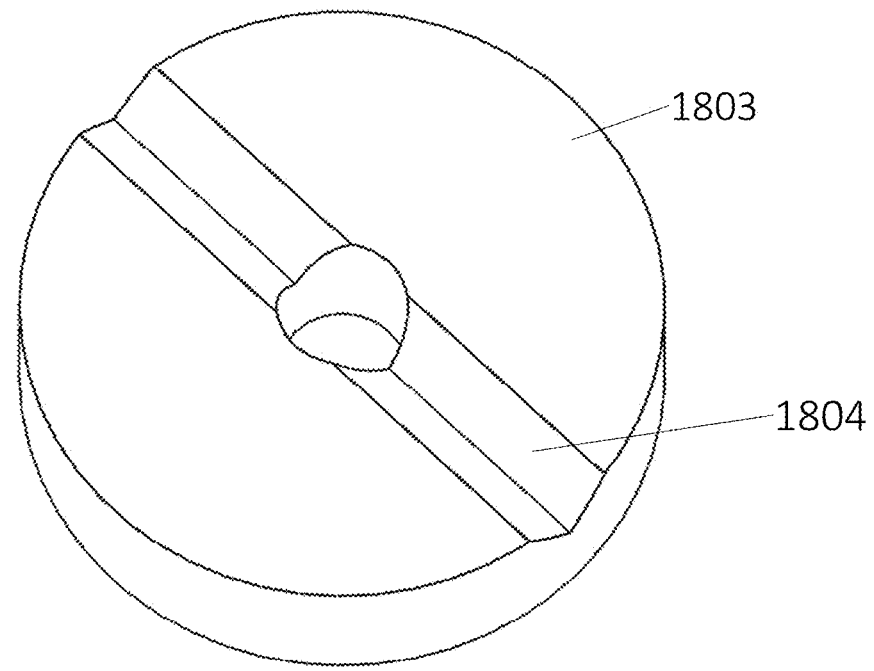
FIG. 18C shows a cover cam required for the operation of the cover according to one embodiment of the present invention.
FIG. 18D shows a view of a face of the rotating cover according to one embodiment of the present invention.
FIG. 18E shows a cross-sectional view of the rotating cover in the closed position and the tubing connector ports according to one embodiment of the present invention.
FIG. 18F shows a cross-sectional view of two connected Perfusion Controllers with their rotating covers in the open position according to one embodiment of the present invention.

FIG. 18B is a close-up view of the tubing connection interface. The cover (not shown) mounts into a socket on the tubing connection interface. The cover's pin fits into an opposite alignment hole on the upstream organ. The alignment hole 1208 fits into the upstream organ's interconnection cover's alignment pin. Magnets 1203 facilitate alignment and attachment of the fluidic interface ports 1801. O-rings 1302 prevent fluid leakage during the operation of the system.

Figure 18D:
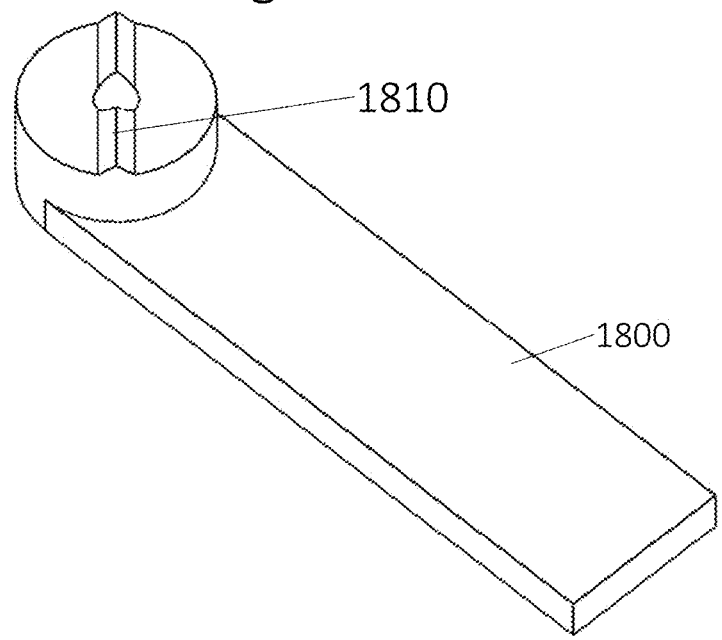

FIG. 18C shows an embodiment of a cover cam 1803 with cam groove 1804 required for the operation of the cover. FIG. 18D shows a view of an embodiment of the face of the rotatable port cover 1800 with cam ridge 1810. The act of lifting the rotatable port cover by rotating it causes the rotatable port cover to pull away from the body of the Perfusion Controller.

Figure 18E:
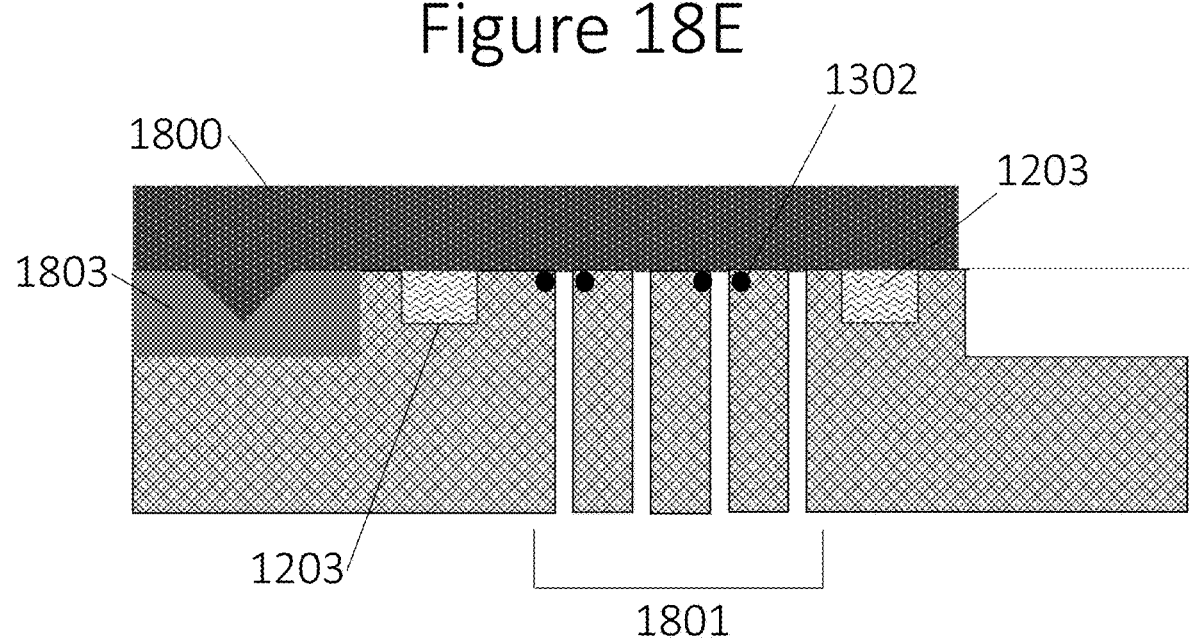

FIG. 18E shows a horizontal cross-sectional view of the rotating cover and the tubing connector ports. In this figure, the rotatable port cover 1800 is in a close position to protect/seal the fluidic interface ports 1801 for preventing leakage and contamination of fluid and/or introduction of air bubbles for the microfluidics module when it is not connected to another. A cover cam 1803 allows the rotatable port cover to be fixed in place flush against the interface ports to prevent leakage or contamination. O-rings 1302 prevent fluid from leaking out of the system. Magnets 1203 facilitate alignment and connection of two interconnects.

Figure 18F:
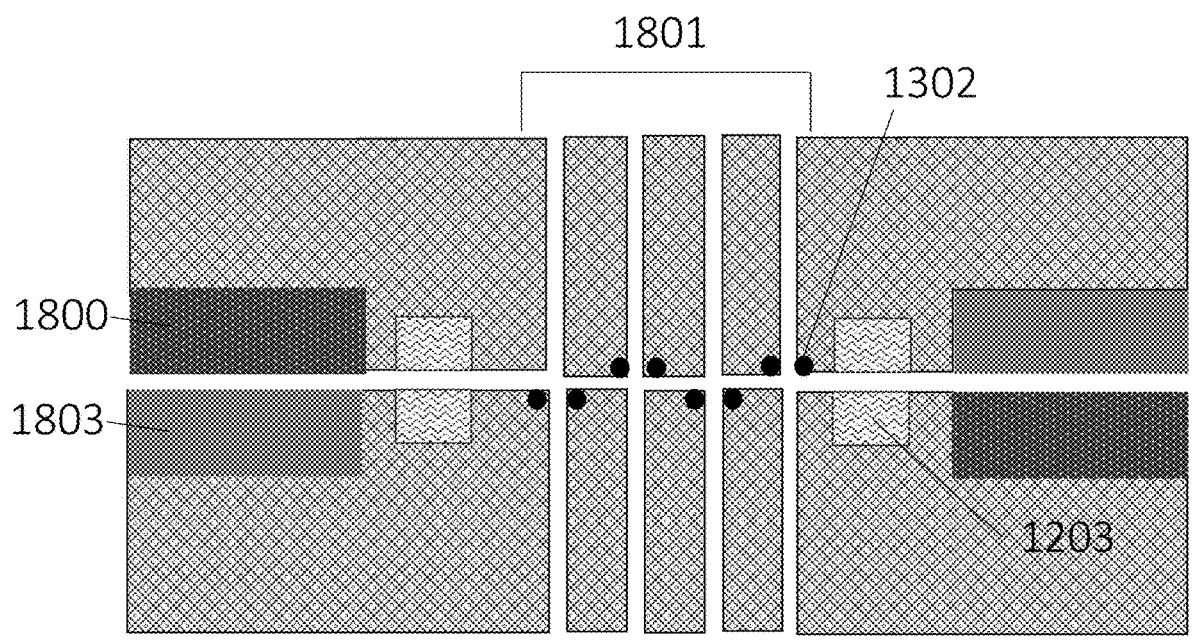

FIG. 18F shows a cross-sectional view of two connected Perfusion Controllers with the interconnect covers 1800 of each raised. Magnets 1203 facilitate alignment and attachment in this embodiment of the system. O-rings 1302 prevent fluid from leaking out of the system. The raised cover of one module fits into the matched recess of the other module.

Figure 19A:
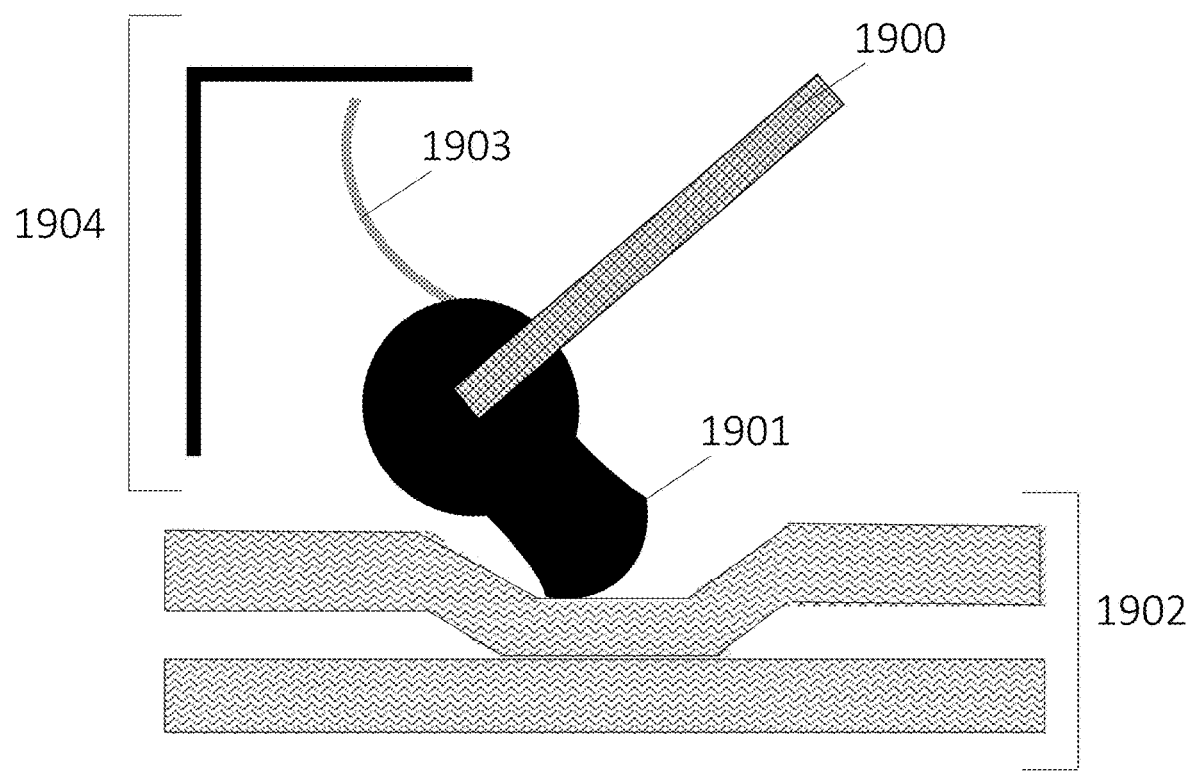
FIG. 19A shows a toggle valve for interconnect control that compresses the microfluidic channels according to one embodiment of the present invention.

FIG. 19A shows a toggle valve for interconnect control that compresses the microfluidic channels, as an alternative to the normally closed Rotary Planar Valve. In this embodiment, the valve is controlled by a handle 1900 which allows a compression actuator 1901 to occlude the microfluidic channel 1902 (not to scale). The handle is held in place by a bistable spring 1903 and housing assembly 1904.

Figure 19B:
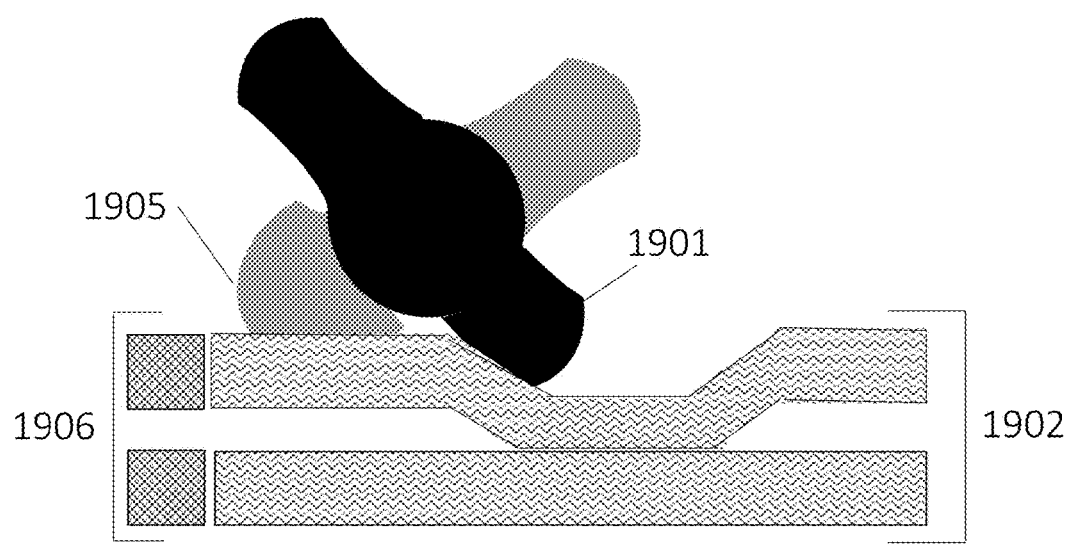
FIG. 19B shows a double-pole, single-throw opposite toggle valve for interconnect control that compresses the microfluidic channels according to another embodiment of the present invention.

FIG. 19B shows a double-pole, single-throw opposite toggle valve of similar design. In this embodiment, the foreground compression actuator 1901 compresses the foreground microfluidic channel 1902 and the background actuator 1905 compresses a microfluidic channel in the background 1906 (partially hidden).

Figure 19D:
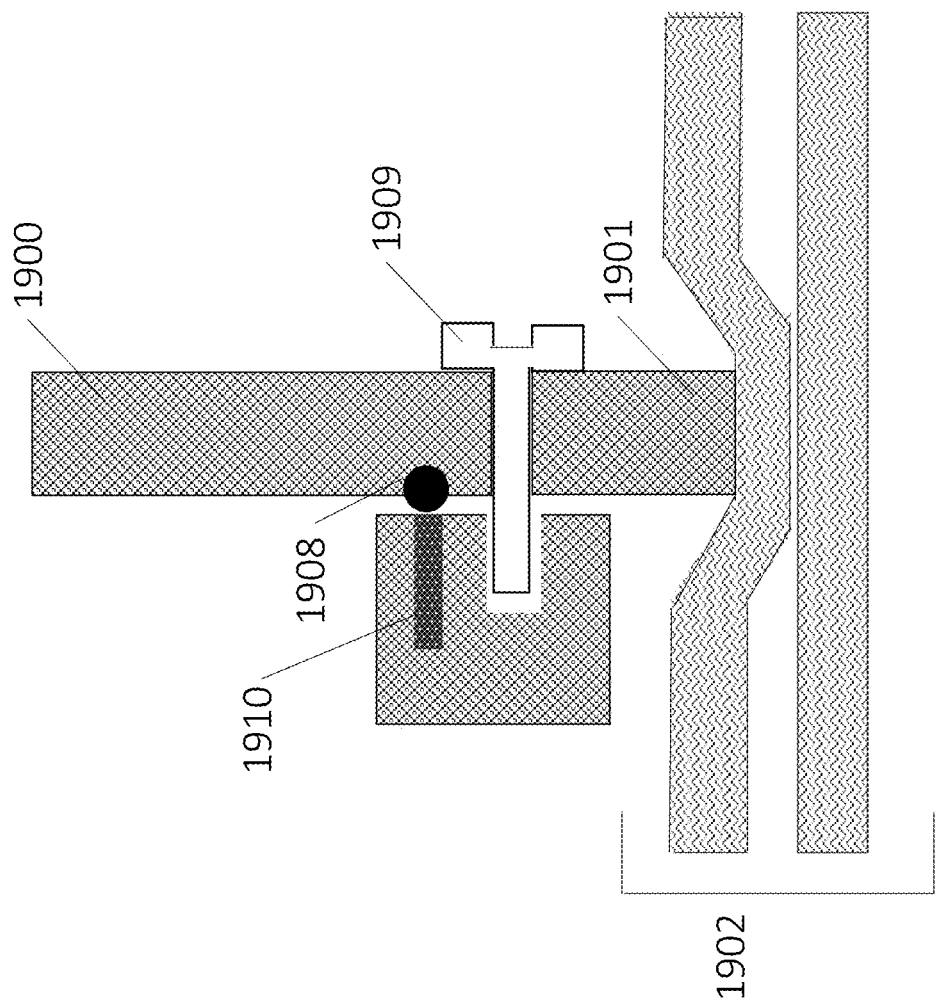
FIG. 19D is a cross-sectional view of the detent in a toggling interconnect valve according to one embodiment of the present invention.
Figure 19C:
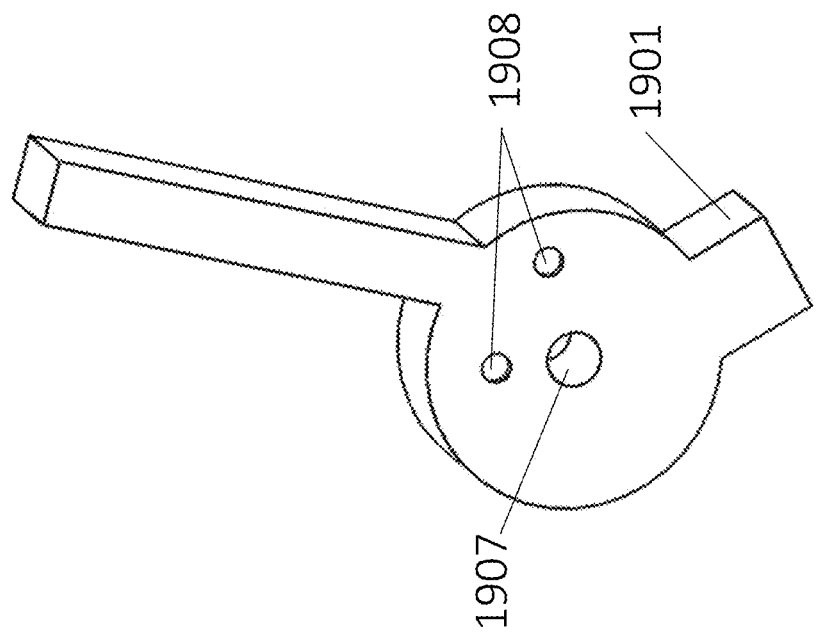
FIG. 19C shows a toggle valve for interconnect control that compresses the microfluidic channels according to yet another embodiment of the present invention.

FIG. 19C shows another embodiment of a toggle valve. In this embodiment an axle hole 1907 central to the actuator facilitates rotation into one of the two states controlled by ball detents 1908 which allows the compression actuator 1901 to occlude the microfluidic channel (not shown).

FIG. 19D is a cross-sectional view of this detent valve. A shoulder screw 1909 holds the actuator in place. The handle 1900 can be rotated into one of two states controlled by the ball detents 1908 and captive spring-loaded ball 1910. In this exemplary embodiment, the microfluidic channel 1902 is occluded by the compression actuator 1901.

EXAMPLE II

Multi-Microformulators for Push-Pull Perfusion of Multiple Open Reservoirs

The MicroFormulator 100 shown in FIGS. 1 and 17 above is described in PCT publication Nos. WO 2012/048261, WO 2013/086505, and WO 2014/081840, and is used to prepare and deliver custom formulations of cell culture media, including drugs, toxins, and growth factors, with the output being delivered to a single bioreactor, organ-on-a-chip, or other fluidic reservoir, or single set of such interconnected devices. The following describes how the integration of computer-controlled microfluidic MicroFormulators, additional computer-controlled valves, and fluidic distribution and collection networks are used to deliver solutions or mixtures of solutions independently to a multiplicity of fluidic reservoirs, such as wells in a cell-culture well plate, multiple tissue or cell-culture bioreactors, or different organs in a coupled, in vitro organ-on-chip microphysiological system, as well as remove fluid independently from each of these reservoirs.

While this could be accomplished by creating a separate MicroFormulator for each reservoir and adding a capacity to also remove fluid from that reservoir, the need for multiple MicroFormulators can be eliminated by the use of a single MicroFormulator that is connected to one or more selector valves to address individual wells or sets of wells in subzones of the well plate. The use of microfluidic splitters would allow the output of a single MicroFormulator to deliver fluid to two or more wells. In one embodiment, a single MicroFormulator, four selector valves, and 24 splitters are used to deliver fluids to all wells in a 96-well plate. The pump of the MicroFormulator is used to withdraw fluid from wells prior to addition of more or different fluids or to obtain samples for off-line analysis. In another embodiment, four selector valves and four pumps create four MicroFormulators, each of which is connected to a 24-port selector valve to enable the delivery of fluid individually to each well of a 96-well plate by means of a fluid-delivery network, and the use of four additional selector valves, four additional pumps, and four 24-port selector valves and the associated fluid delivery network would allow removal of fluid individually from each of these wells. Together, such a system could be configured as a "Smart Lid" that would rest on top of a standard 96-well plate and provide these functions locally to the well plate beneath the Smart Lid. The Smart Lid could also support a variety of sensors, actuators, and controllers, all operated by one or more on-board microcontrollers.

In certain aspects, the present invention relates to an approach to distribute the fluid-handling operations across the system with a large number of fluid-handling units, so that a single well plate can undergo fluid-handling operations over a substantial fraction of the duration of the experiment. With a fluid handler dedicated to a single well plate, it would no longer be necessary to replace pipettes after a fluid handing operation—it may be sufficient to replace the fluidics module only at the end of a long-term experiment.

Accordingly, the present invention overcomes limitations of existing fluid-handling pipetting robots and enables the delivery of a physiologically realistic, time-controlled concentration profile of drugs or toxins to cells being cultured in a well plate. Having the pumps, valves, splitters, fluid delivery networks and other sensors and actuators mounted on the lid of the well plate allows fluid-handling operations to be performed in a massively parallel fashion, with different well plates being able to be controlled independently and asynchronously, rather than having the fluid delivery process limited to operations performed serially by a single fluid-handling robot. In contrast to other approaches (Flex-Cell or Cell ASIC), there are no tethers between the Smart Lid to an external controller, since the control of the pumps, valves, sensors and actuators is performed by on-board microprocessors that communicate with other computers wirelessly. Battery power can operate the system when the well plate and lid are not located in a docking station that provides power, vacuum, or other gases. This system will be more readily accepted by the drug discovery/development communities than the lower-throughput organ-on-chip approach. In effect, inventors are bringing the robot to the well plate, in contrast to the common approach of bringing the well plate to the robot. In certain aspects, the novelty of the present invention includes the integration of pumps, valves, splitters, fluidic networks, sensors and actuators on the lid of a standard well plate.

Traditional instrumentation associated with advanced cellular assays is typically benchtop in nature and poses a critical limitation to the adoption of this technology by the biopharma community. For instance, microfluidic devices often utilize multiple syringe pumps costing $2,000 or more each, or on-chip pneumatic peristaltic pumps that require precise microfabrication and multiple solenoid valves, a computer, and an external source of pressurized gas at a cost of about $500 per pump and the need to tether the device to the solenoid pneumatic controller by a bundle of plastic tubes. For the past decade, under the direction of Dr. John P. Wikswo, the Vanderbilt Institute for Integrative Biosystems Research and Education (VIIBRE) has been developing instrumentation and techniques to control single cells and small cell populations [1-6].

In 2010, VIIBRE introduced a new on-chip peristaltic pump that requires purchase of only a stepping motor (about $15) and a controller (about $50) but was somewhat labor intensive to fabricate [7]. This work led to the development of an entirely new class of rotary, planar peristaltic micropumps (RPPMs) and rotary planar valves (RPVs) that cost at least an order of magnitude below commercial instruments for precise temporal control of biological fluids [8]. While low-cost, compact, and easy-to-fabricate RPPM arrays can be viewed as general purpose biological research instruments for dynamic in vitro control of cellular chemical and fluidic environments, more importantly, RPPM and RPV arrays that cost about $15/channel enable the creation of compact, low-cost MicroFormulators that can deliver on-demand custom mixtures. The present invention would support and be supported by a number of associated microfluidic and microfabrication technologies [8-16].

In certain aspects, the key of the present invention is the use of a multiport, rotary planar valve that can be implemented in one of several embodiments, such as the missing-ball, open rotary planar valve (NO-RPV), and the fixed-ball, rotating-actuator, normally closed rotary planar valve (NC-RPV). In certain embodiments, the present invention is based on the NC-RPV, but other valve implementations could also be used to practice the present invention. As described in FIGS. 1 and 2 of PCT publication No. WO 2014/123600, an exemplary embodiment of a NC-RPV has a fluidic channel that connects five input channels to a common output line. A rotating actuator depresses all balls except those under a detent in the rotating actuator. Any channel whose ball is allowed to rise into the detent in the rotating actuator allows fluid to be drawn through the fluidic channel beneath. The balls are held in position by a small plastic cage.

Figure 20:
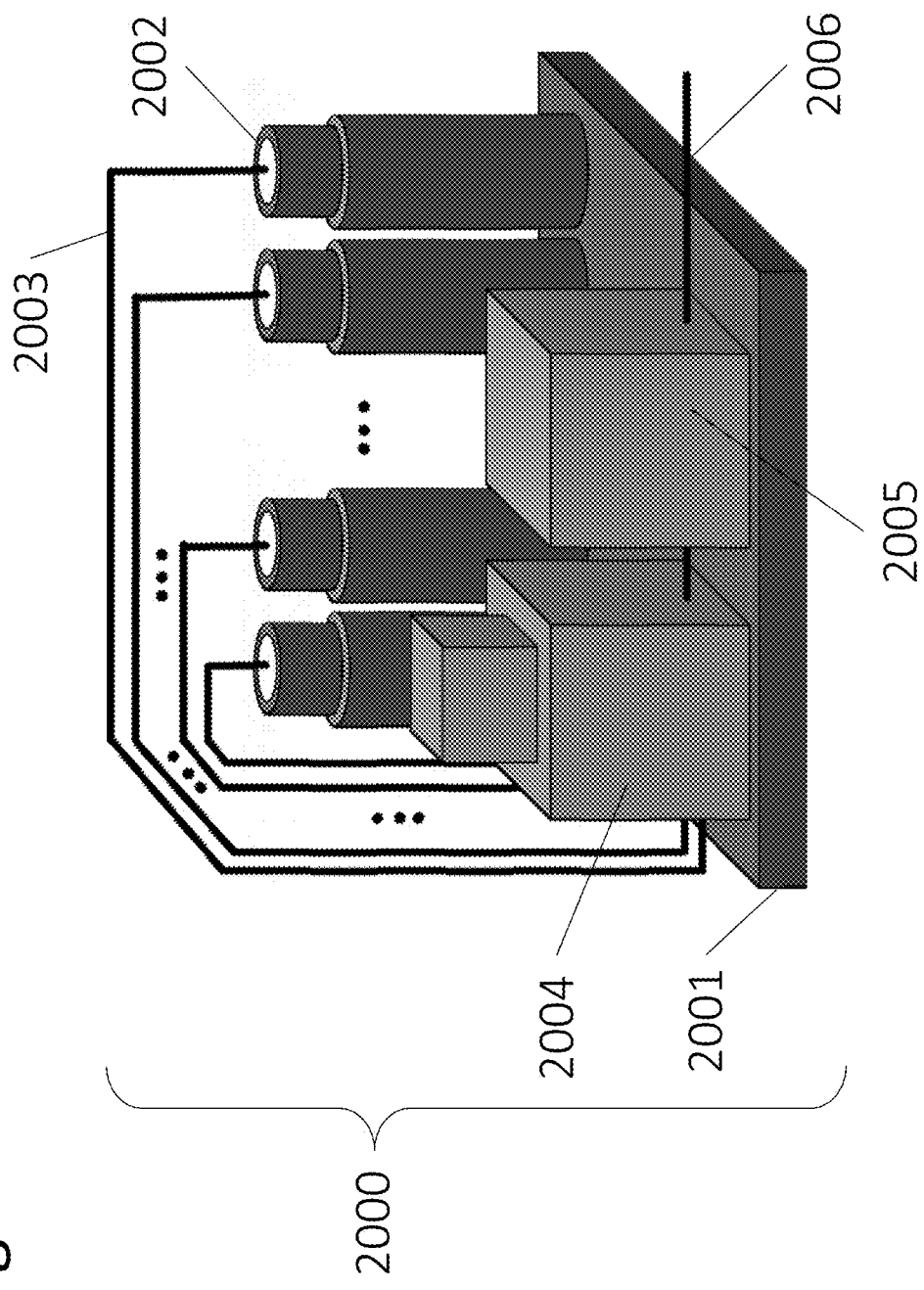
FIG. 20 shows a MicroFormulator system according to one embodiment of the present invention.

The first MicroFormulator was developed by Carl Hansen [17-19]. Typically, these MicroFormulators require a large number of pneumatic control lines for each valve in the fluidic circuit and are limited to low volumes as defined by the size of the microfluidic shuttles and mixers. The present invention relaxes the limitation on the volumes that can be produced and delivered by using higher capacity pumps and multiport rotary mechanical valves rather than single-port pneumatic ones. The RPPM-RPV MicroFormulator is described in PCT publication Nos. WO 2012/048261 and WO 2013/086505. FIG. 20 shows the components of one MicroFormulator implementation 2000 as described in the two PCT publications: There is a base plate 2001, two or more fluid reservoirs 2002 that are connected by fluid lines 2003 to an input selector valve assembly 2004. Given the setting of the input selector valve, the pump assembly 2005 withdraws fluid from the selected reservoir and delivers it to the single output tube 2006, which in turn is connected to a single organ-on-chip, bioreactor, or reservoir.

Figure 21:
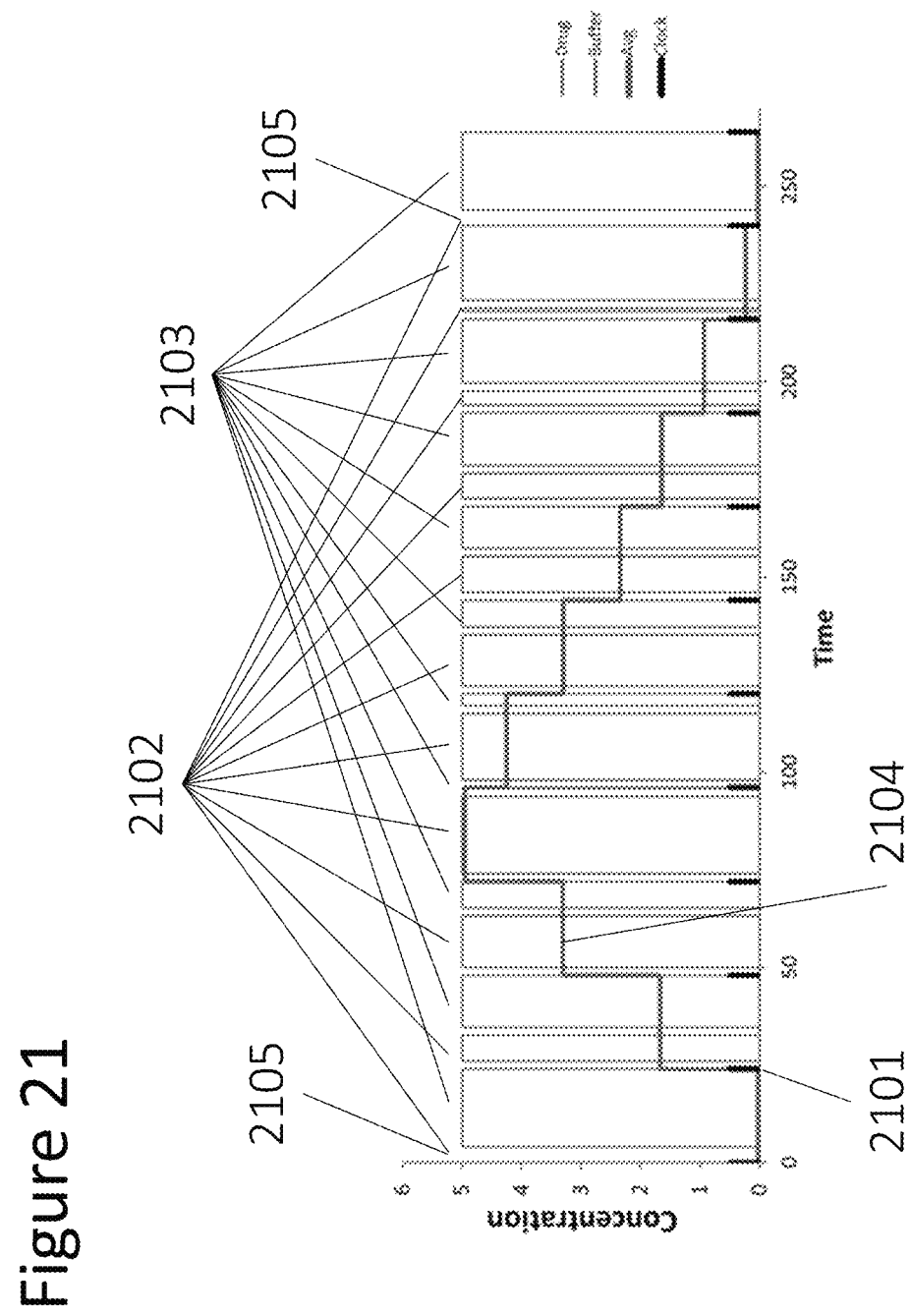
FIG. 21 shows a chart of a complex concentration vs time drug delivery profile using time-division multiplexing to create a gradual increase and decrease in drug concentration over time in a MicroFormulator according to one embodiment of the present invention.

In contrast to a pipette-oriented fluid-handling robot, a MicroFormulator can provide a complex concentration vs time drug delivery profile using time-division multiplexing as shown in FIG. 21 to create a gradual increase and decrease in drug concentration over time, as would occur in oral delivery of a drug to a human or an animal. In this approach, the duration with which two or more solutions are drawn from their respective reservoirs and fed into a common line is varied to approximate the desired wave form. The smoothness of the wave form is determined by the clock rate at which the desired wave form is reconstructed, and by the mixing of the solutions either in the outlet tubing or in a downstream reservoir or mixer.

The pharmacokinetic (PK) time course would be different for intramuscular, intraperitoneal, skin, or inhalation delivery, all of which could be simulated with the time-division multiplexing process supported by a MicroFormulator 2000. Assume that the system operates based upon a regular clock pulse 2101 that repeats after a chosen sampling interval. Immediately after a clock pulse, in this example drug is delivered 2102. After the delivery of every aliquot of drug, an aliquot of buffer or other drug-free media 2103 is delivered. In FIG. 21, note that there is no drug in the first or last aliquot, ensuring that the initial and final concentrations of drug in the delivery profile 2104 are zero. Through diffusional and convective mixing, the interspersed aliquots of drug and non-drug will be combined to produce a smooth drug concentration profile. Should any step-like features remain in the profile, it would be straightforward to reduce the clock pulse interval, consistent with the Shannon-Nyquist sampling theorem. At present, the minimal valve-open interval for the MicroFormulator is approximately one second, although with anticipated technical improvements to the valve controller, this interval should be reduced. Hence, for accuracy it is assumed that the practical minimum is ten times the absolute minimum, i.e., 10 seconds. Given the hour time scale of many human PK drug delivery protocols, the ratio of seconds to hours indicates that the MicroFormulator has perfectly adequate temporal resolution and dynamic range. The MicroFormulator can prepare mixtures of reagents, drugs, toxins, and metabolites limited only by the number of ports on the input selector valve 2004 in FIG. 20.

Figure 22A:
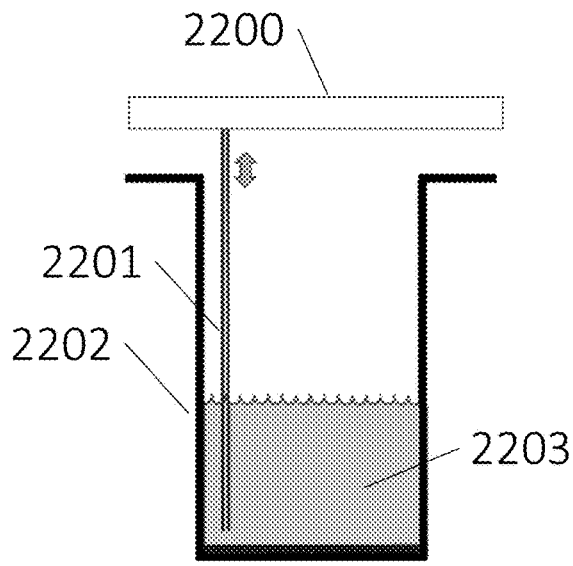
FIG. 22A shows a MicroFormulator head tube-support plate to maintain a single fluidic tube above one well of a multiwell plate according to one embodiment of the present invention.
Figure 22B:
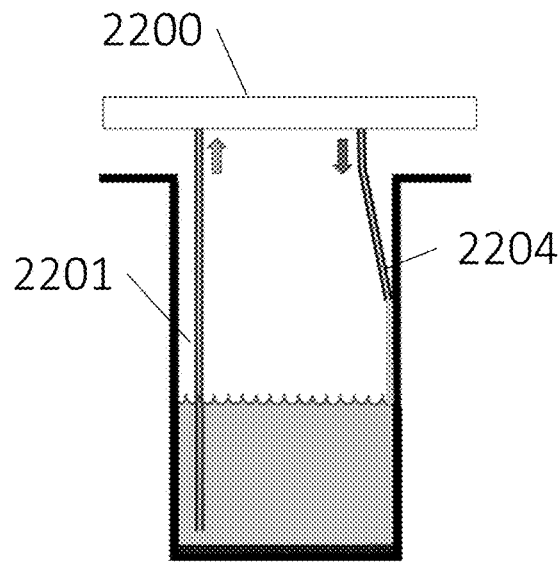
FIG. 22B shows a MicroFormulator head tube-support plate used to maintain sets of two separate tubes in a well according to one embodiment of the present invention.
Figure 22C:
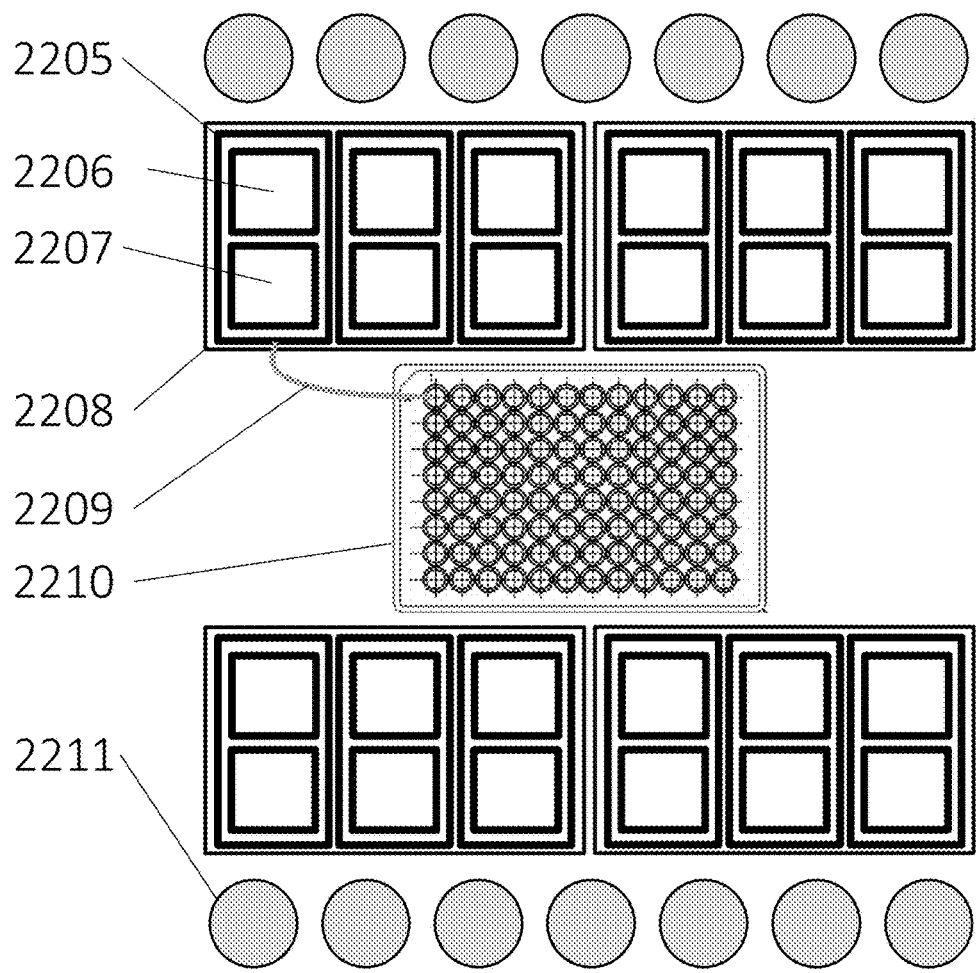
FIG. 22C shows twelve MicroFormulators, each with an input-selector RPV and a Rotary Planar Peristaltic Micropump (RPPM) to address 12 wells according to one embodiment of the present invention.

The challenge is to apply the MicroFormulator concept to multiple wells in a well plate, as shown in FIG. 22C. FIG. 22A shows a MicroFormulator head tube-support plate 2200 that is shown to maintain a single fluidic tube 2201 above one well 2202 of a multiwell plate. This tube is used to both deliver and remove fluid 2203 from that well, for example by connecting it to the tube 2006 at the output of the MicroFormulator in FIG. 20. In this case, one of the ports of the input selector valve 2004 of that MicroFormulator would be assigned to waste removal, and the other four ports, in this example, would be used to provide drug and media. As many additional tubes 2201 could be added to the plate 2200 as there are wells 2202 to address.

Alternatively, the tube-support plate could be used to maintain sets of two separate tubes in the well, a long tube 2201 and a short tube 2204, as shown in FIG. 22B. If the tube 2204 is used to deliver fluid and the tube 2201 to remove it, the separation of the two tubes ensures diffusional and convective mixing of the fluid in the well to accelerate media change by flow-through of media. Alternatively, the tube 2201 could be used for delivery and the tube 2204 for removal, wherein the shorter length of the tube 2204 could serve as means to set the fluid level in the well by providing constant or on-demand suction to that tube. Should the fluid level rise above the lower end of the tube 2204, the fluid would rise no further as long as adequate suction was applied.

This concept can be extended to address all of the wells in a 96-well plate, to create a multichannel MicroFormulator that becomes an integral part of a smart well plate. For example in FIG. 22C, and in this example mounted in groups of three 2208, twelve MicroFormulators 2205, each with an input-selector RPV 2206 and an RPPM 2207 could address 12 wells in well plate 2210 using tubes such as 2209. The MicroFormulators can draw fluids from or return fluids to reservoirs 2211. Or, by using a fluidic splitter, these 12 MicroFormulators could be used to address 12 groups of four wells each, thereby providing 4 biological replicates for each concentration vs time profile in 48 wells. Eight-fold splitters would allow addressing of each well in a 96-well plate, in groups of eight. Hence multiple fluidic control units would enable massively parallel, asynchronous pharmacokinetic (PK) control of well plates without the restriction of a central fluid-handling robot. However, it is critical to reduce the size and cost of each fluidic control unit so that hundreds or even thousands could be used at one time. The present invention presents several means to accomplish this.

Figure 23A:
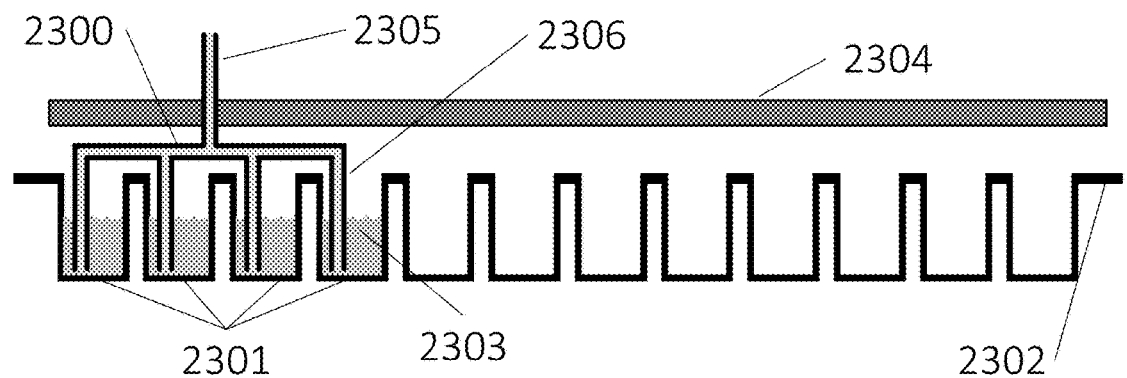
FIG. 23A shows a MicroFormulator head tube-support plate that is shown to maintain a four-tube splitter above four wells of a multiwell plate according to one embodiment of the present invention.

Splitters will allow a single with its input selector valve 2004 and pump 2005 as shown in FIG. 20, to address multiple wells by connecting to the output tube 2006. FIG. 23A shows a single four-fold splitter 2300 that connects four wells 2301 in a well plate 2302 to interface with the fluid 2303. Multiple splitters are supported in rigid positions by a lid or plate 2304. Each splitter has a common tube 2305 that connects to the single μF. Delivery needles 2306 in each well will always be in contact with the fluid in the well. Splitters are balanced to ensure equal delivery to the four wells.

Figure 23B:
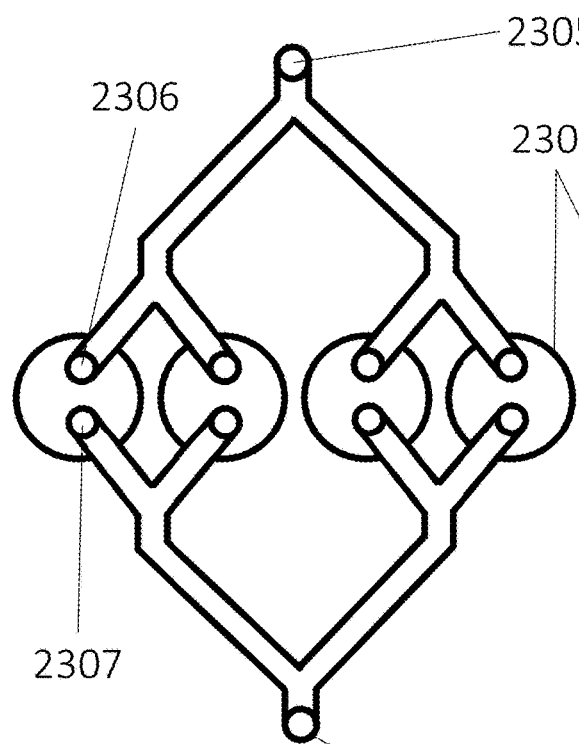
FIGS. 23B and 23C show two alternative configurations of four-well delivery and removal suction splitters according to embodiments of the present invention.
Figure 23C:
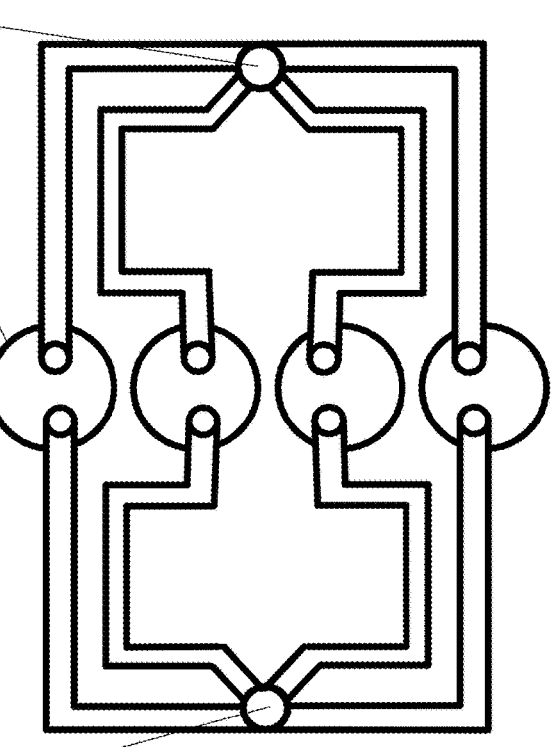

Using the configuration of FIG. 23A, a separate set of suction needles can be added to remove fluid from the wells. FIGS. 23B and 23C show two alternative configurations of delivery and removal suction splitters with separate needles, wherein the path lengths between the common tube 2305 and the end of the delivery needles 2306 are the same to ensure fluidic balance and hence equal delivery. Similarly, there is an equal path length between the end of each removal needle 2307 and the common removal suction port 2308. The configuration on FIG. 23C is less prone to flow disruption by bubbles than the configuration in FIG. 23B. Hence each splitter assembly could have either just a delivery line (FIG. 23A), or both a delivery and a suction line (FIG. 23B). In the case of a single delivery line, that single line could be used for suction and removal of fluid from the well or reservoir by reversing the direction of the pumps, whose output would be directed to a waste reservoir.

The multiple suction splitters that are required for an entire well plate could be connected collectively to a single vacuum pump, or to a valve network to control suction. However, one of the limitations of splitters is that it may be difficult to achieve the requisite balance between all wells addressed by the splitter. Particular attention must be paid to the amount of fluid withdrawn from each well to avoid drawing air into the fluidic splitter, since once a single branch of a suction splitter begins to draw air, the difference in the viscosity of air and water will make it very hard to thereafter remove any fluid from the other wells.

Let us next consider the possible configurations of a single-tube system as shown in FIG. 22A, in which a single pump is used to both deliver and remove fluid from each well or set of wells coupled by splitters. For this example, it is assumed that the input selector valve 2004 (FIG. 20) has either five or eight ports, but other numbers of ports can also be utilized to practice the present invention. There are a number of different configurations wherein splitters and µFs can be combined.

Eight standard µFs (each having two motors) with five- or either-port input RPVs only (16 motors) and no output valves, and eight 4× splitters would address one-third of 96 wells.

A five- or eight-port input RPV µF with an eight-port output RPV (3 motors) could address 8 individual wells. With 8 sets of four-well splitters, this could address 32 wells, or one-third of a well plate.

Three five- or eight-port input RPV µFs with an eight-port output RPV (9 motors) would address 24 individual wells. Using this with 24 sets of 4 well splitters would address all 96 wells of a well plate.

Six five- or eight-port input RPV µFs with eight-port output RPV (18 motors) would address 48 individual wells, such that with 48 sets of two-well splitters, it would be possible to address all 96 wells in a well plate.

Twelve five- or eight-port input RPV µFs with eight-port output RPV (36 motors) would address all 96 individual wells.

Six five- or eight-port input RPV µFs with 24-port output RPV (12 motors) would address all 96 individual wells in a plate.

FIGS. 24A-24C present one of the embodiments of a 96-Channel MicroFormulator, wherein a well plate 2302 has its own dedicated fluid delivery system for stand-alone physiological PK drug delivery. FIG. 24A shows eight single-channel µFs 2000, each connected by means of a length of tubing 2401 to a four-well splitter 2402 mounted in a rigid sub-plate 2403 that addresses one-third of a well plate at a time. FIGS. 24B and 24C show close-up views of a portion of this system.

FIGS. 25A and 25B show how this process can be applied to one-third (FIG. 25A) or one-quarter (FIG. 25B) of a well plate at a time using appropriately configured sub-plates 2402 and 2502, respectively. The sub-cover can be moved from the first section to the second or third section for total coverage of the 96-well plate. If cross-contamination is a problem, the needle array will have to be flushed internally and washed externally between sections. Alternatively, additional MicroFormulators could be added to allow independent operation of multiple sub-plates simultaneously. For example, to fully connect to each well in the well plate 2302 in FIG. 24 would require 48 separate motors.

The delivery needle can also be used for fluid removal as long as the fluid level never drops to the point of air entering the tube, which would imbalance the splitter. The well can be overfilled, since the suction line would ensure that the volume of fluid in the well never exceeds a certain amount. The strategy of overfilling each well and removing the excess fluid would ensure that the proper concentration is delivered to each well. The MicroFormulator can hence be used to control the concentration of drug that is delivered over the course of time.

It is necessary to determine whether the suction lines for fluid removal are independent, grouped, or common. A common suction could be controlled by a single solenoid valve connected to an external vacuum pump or suction line. Anything else requires either multiple solenoid valves, RPVs to connect wells to vacuum or an RPV, or an individual RPV for each suction line. The limitation of suction on splitters is that sucking air will imbalance the splitter, and it is difficult to provide a high enough resistance at the end of the suction tube within the well to ensure that balance between the tubes is maintained even when sucking air.

The number of MicroFormulators needed to address a well plate is determined by the pump rate and the required pump duty cycle. For example, if the RPV in the µF can deliver fluid at 40 µL/min, the delivery of 100 µL per well each hour will require four pumps. Hence this requires that each well-plate have four µF modules, each addressing 24 wells, with one RPV following the input selector valve that has a number of ports consistent with the number of components to be combined by the µF, e.g., five or eight in the examples discussed so far. For a plate divided into thirds (FIG. 25A), one eight-port output selector valve for each µF would then allow the µF to address the eight splitters. If instead, the plate were divided into quarters (FIG. 25B), then the eight-port output selector valve could select between any of six four-port splitters and two additional lines, for example one for waste and one for connection to a washing fluid to enable both forward and reverse fluid flushing/washing of the system.

Figure 26A:
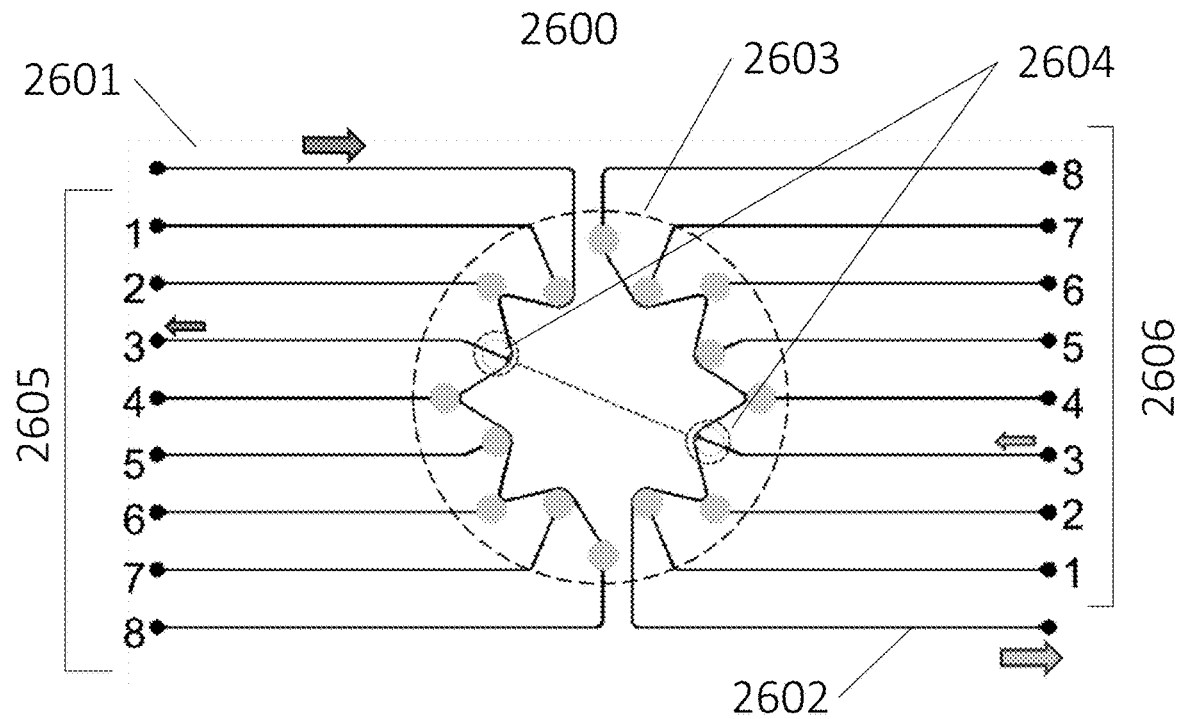
FIG. 26A shows an 8×2 rotary planar selector valve for simultaneous controlling both delivery and suction according to embodiments of the present invention.

The development of an 8×2 selector valve 2600 as shown in FIG. 26A enables simultaneous control of both delivery and suction. In one embodiment as shown in FIG. 26A, the common inlet port is a port 2601, and the common outlet port is a port 2602. As with other RPVs, there is a rotary actuator 2603, in this embodiment with a pair of detents on opposite sides, such that as the actuator 2603 is rotated, opposite pairs of inlet lines 2605 and outlet lines 2606 are connected to the common inlet port 2601 and outlet port 2602. The pairs of inlet and outlet lines 2601 and 2602 can each be connected to a separate bioreactor or an individual well in a well plate.

Figure 26B:
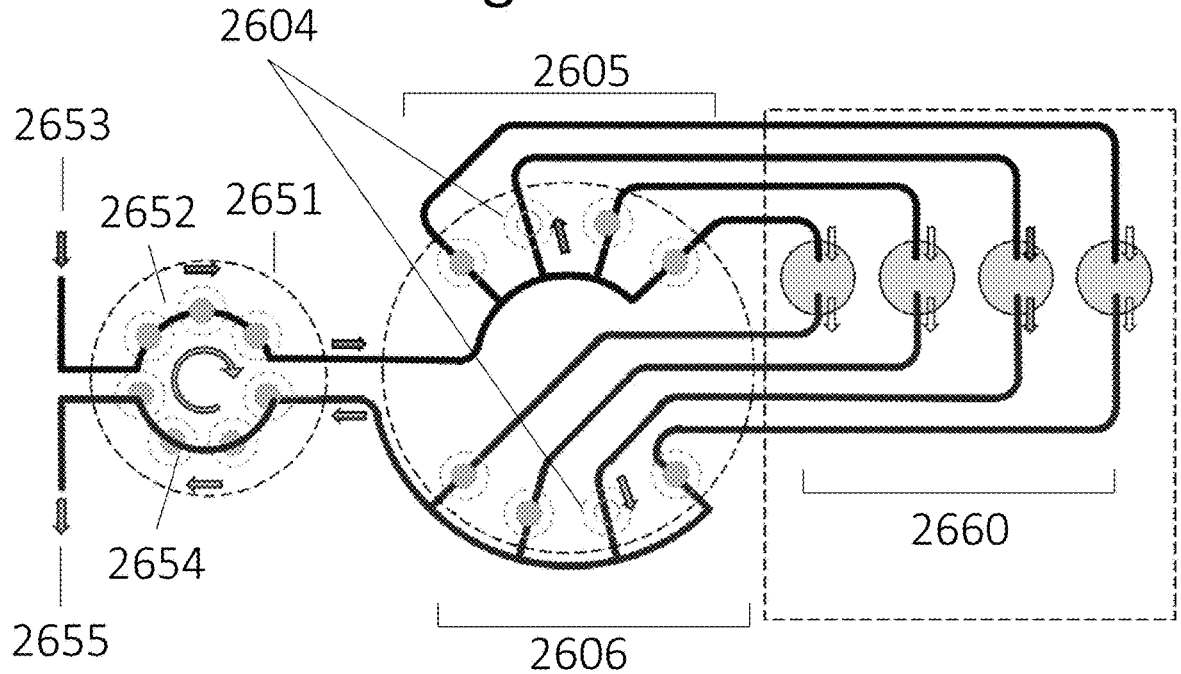
FIG. 26B shows a push-pull architecture configured for a 4×2 rotary planar selector valve with an integrated dual-sided Rotary Planar Peristaltic Micropump according to embodiments of the present invention.

FIG. 26B shows this type of push-pull architecture configured for a 4×2 selector valve 2650 with an integrated dual-sided pump 2651. The inlet pump 2652 draws fluid 2653 from an input selector valve (not shown, but equivalent to valve 2004 in FIG. 20) and delivers it to the selected inlet line 2605 for delivery to the selected well in a well plate or a bioreactor 2660. Simultaneously, an output pump 2654 withdraws fluid from the selected well 2660 and delivers this fluid 2655 to either a waste line or an output director valve (not shown). The limitation of this design is that it does not allow independent control of the input and output pumps, and hence the only way to control the level in a well is to use the long-tube/short-tube approach, wherein if excess fluid is delivered to a well, the shorter tube on the output will determine the volume of fluid in the reservoir. It is worthy of note that it is also possible to add a second concentric set of detents in the actuator to allow an alternative, possibly more complex addressing of both the input and output lines.

Figure 27A:
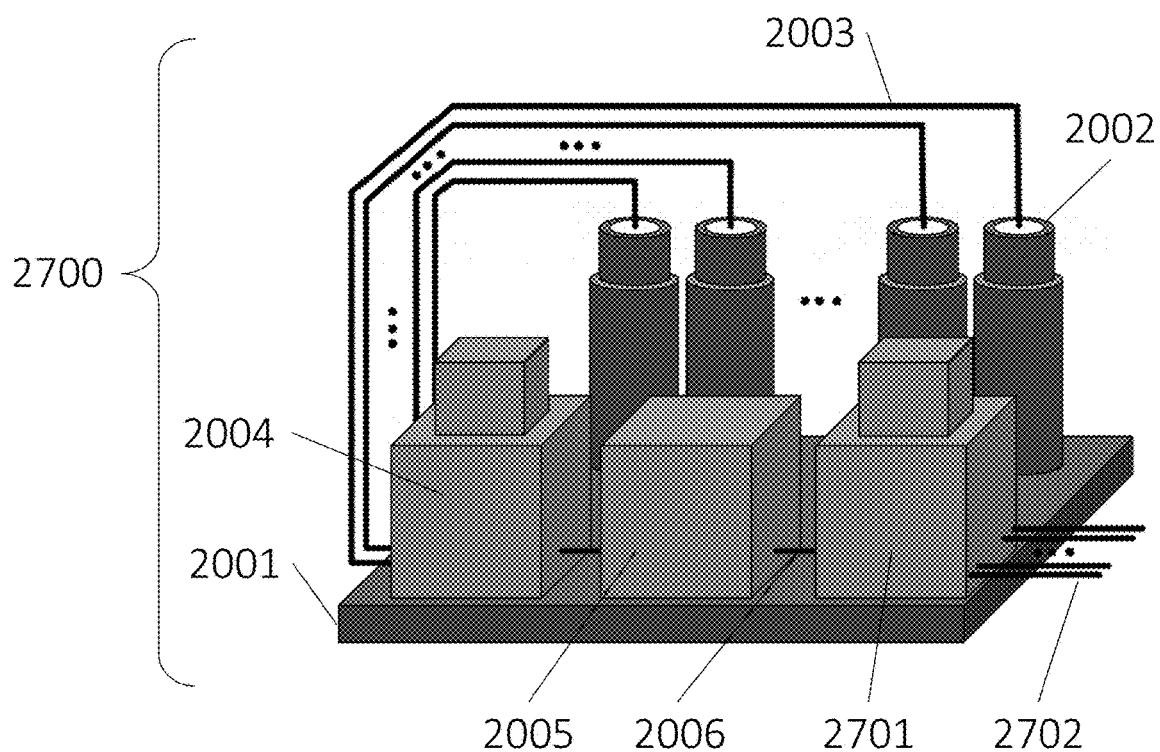
FIG. 27A shows a three-motor MicroFormulator implementation to independently deliver and remove fluid from four wells, or reservoirs, or organs-on-chips according to one embodiment of the present invention.
Figure 27B:
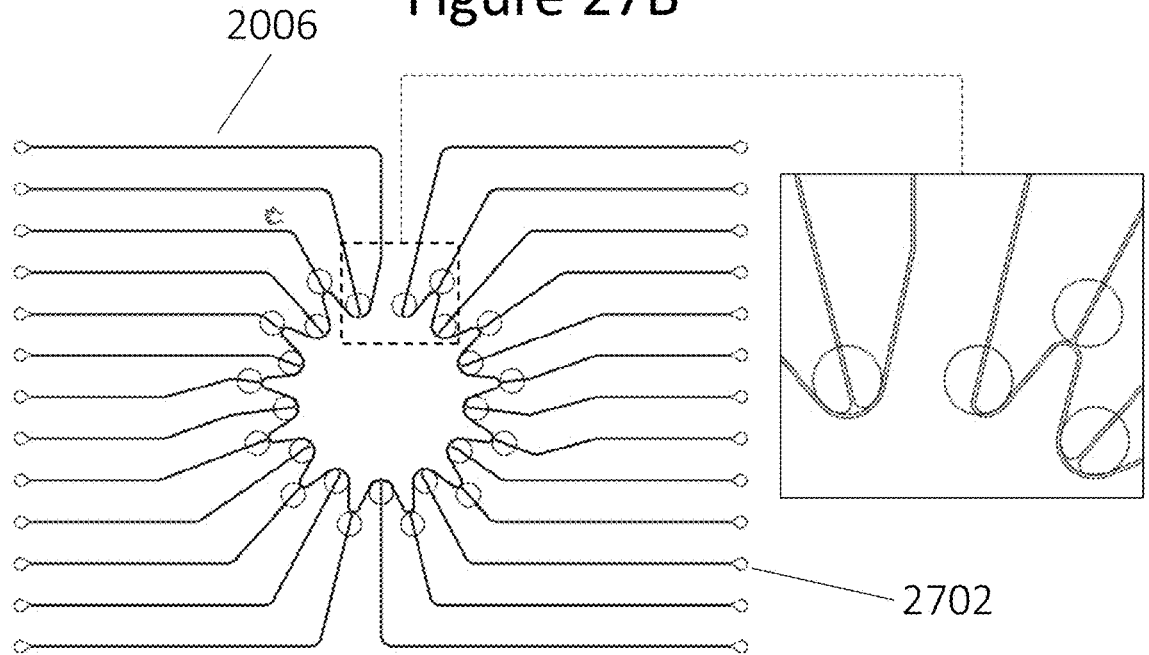
FIG. 27B shows a layout of a 24×1 Rotary Planar Valve (RPV), where the input line is connected to any of 24 output lines according to one embodiment of the present invention.

Given the need to deliver the output of a MicroFormulator to one of a multiplicity of wells or bioreactors, it is worthwhile to expand upon the design 2700 shown in FIG. 27A to include three motors, the third of which drives an input director valve 2701 that directs to flow 2006 from the input pump 2005 to one of a multiplicity of input lines 2702, each of which in turn is connected to an individual bioreactor or well in a well plate. FIG. 27B shows the layout of a 24×1 RPV, where the input line 2006 can be connected to any of 24 output lines 2702.

Figure 28A:
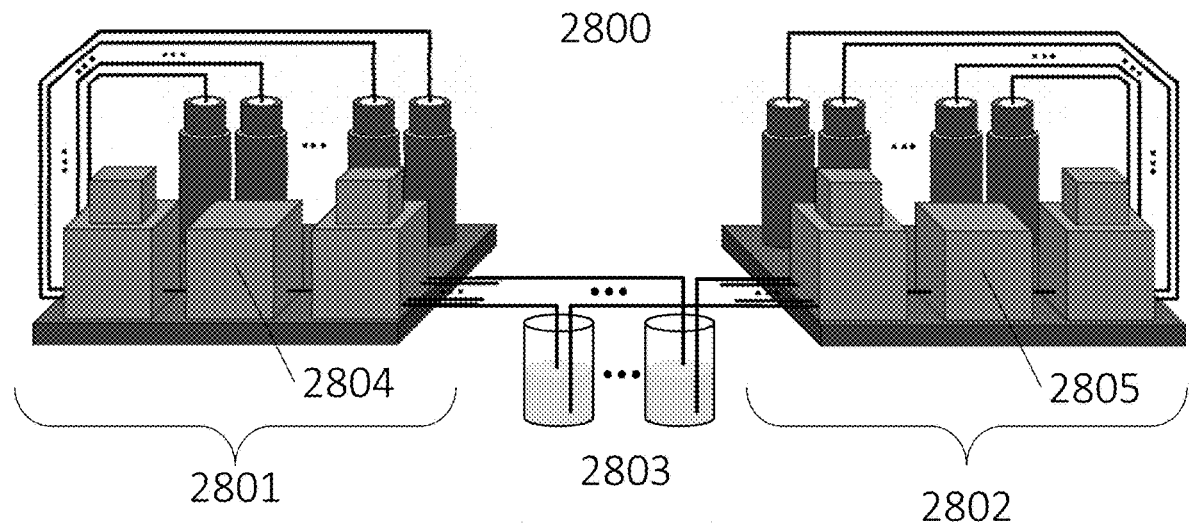
FIG. 28A shows an implementation of two, three-motor MicroFormulators connected as a single unit to wells to provide independent fluid delivery and removal according to one embodiment of the present invention.

FIG. 28A shows how two, three-motor MicroFormulators can be connected as a single unit 2800 to wells such that one input MicroFormulator 2801, for example that shown by 2700 in FIG. 27A, delivers fluid individually to each of 24 wells 2803. A second, output MicroFormulator 2802 can independently remove fluid from each of the 24 wells 2803. The advantage of this push-pull architecture is that it provides full, independent control of the volume of fluid in each well. A well can be filled by having the input (fill) pump 2804 on and the removal (output) pump 2805 off. A well can be washed or have its media changed by having the input (fill) pump 2804 on and the removal (output) pump 2805 on. A well can be drained by having the input (fill) pump (2804) off and the removal (output) pump 2805 on, as long as the withdrawal tube reaches near to the bottom of the well.

Figure 28B:
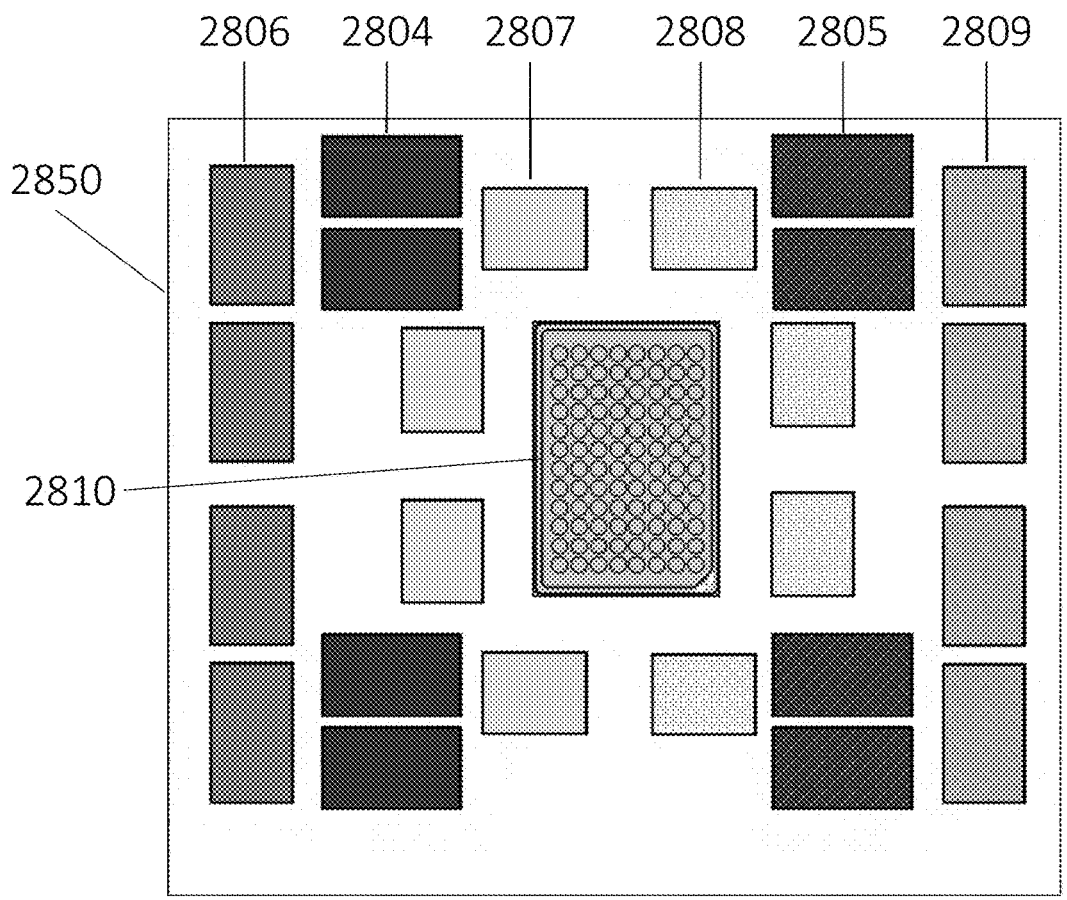
FIG. 28B shows a schematic layout of a 96-channel MicroFormulator according to one embodiment of the present invention.

FIG. 28B presents a schematic layout of a 96-channel MicroFormulator 2850 that combines four of the three-motor input MicroFormulators 2801 with four of the three-motor output MicroFormulators 2802 as a single unit with four input selector valves 2806, four input pumps 2804, four 24-port input director valves 2807, four output-director valves 2808, four output pumps 2805, and four output director valves 2809. In effect, the configuration of FIG. 28B is simply four units of the configuration in FIG. 24A, wherein each set of these four combined units addresses 24 of the wells in a 96-well plate. With this design, an input selector valve 2806 can select between various input reservoirs not shown that, through time-division multiplexing, be pumped by the input pump 2804 into the 24-port input selector valve 2807 and hence directed to a single well of the well plate 2810. By symmetry, an output selector valve 2808 can determine from which well fluid will be drawn by the output pump 2805. The output director valve 2809 can then determine to which reservoir the output from the well is delivered. In one embodiment, the input selector and output director valves are both five-port, but any number of ports could be designed into these valves. It is important to realize that one or more outputs of any of the output director valves 2809 could be sent to one or more of the input selector valves 2806, thereby allowing recirculation or fluid exchange between different wells in the well plate.

Figure 28C:
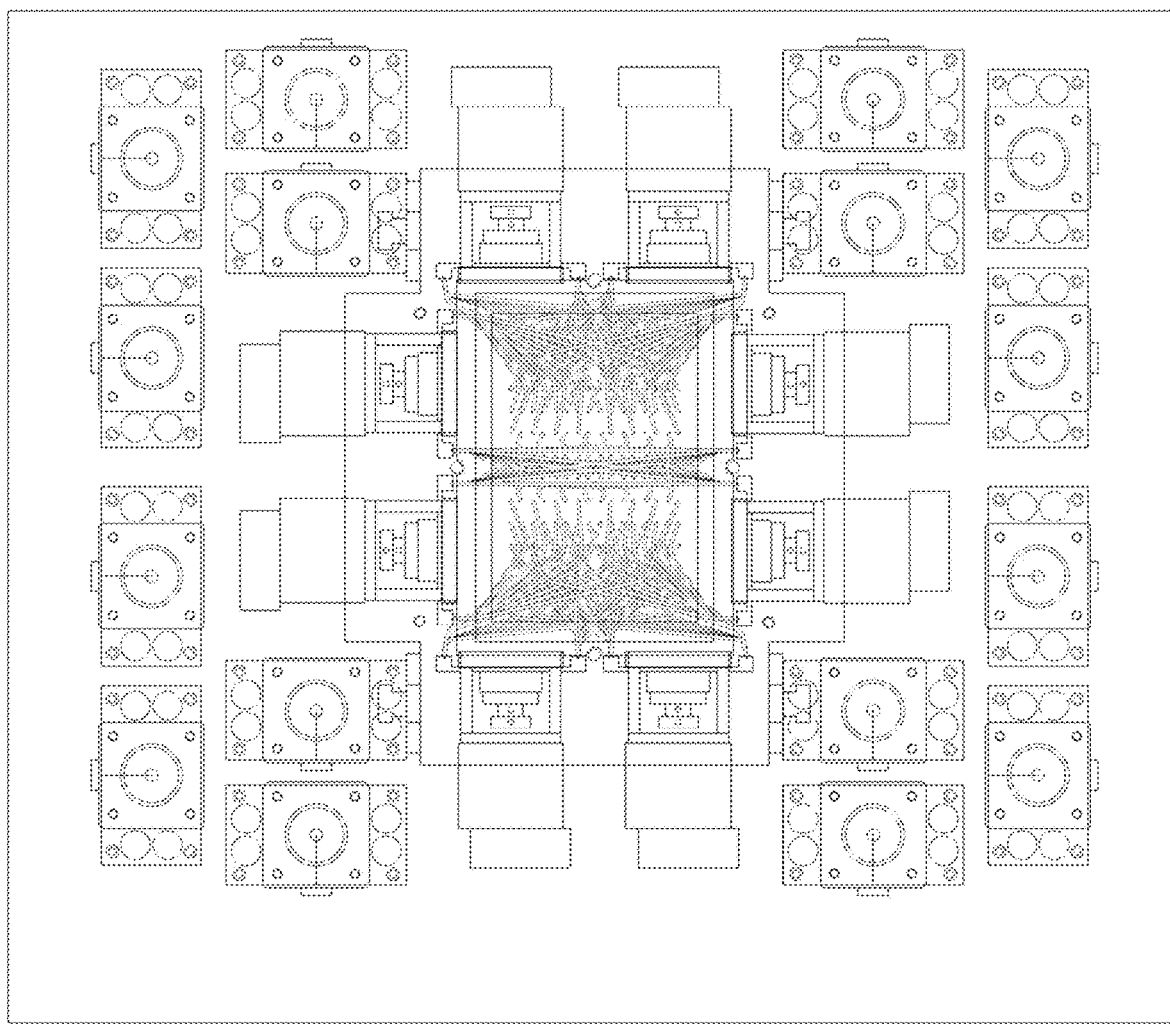
FIG. 28C shows a view of the 96-port, push-pull MicroFormulator using NEMA-17 motors and plastic tubing to connect to the well plate according to one embodiment of the present invention.
Figure 28D:
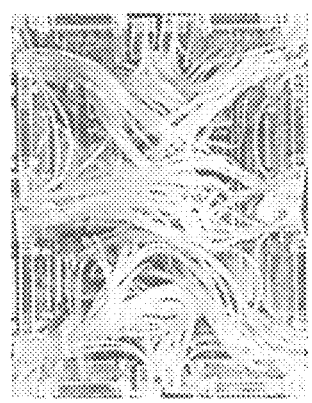
FIG. 28D shows an actual tubing network according to one embodiment of the present invention.

FIG. 28C shows a plan-view line drawing of one embodiment of the 96-port, push-pull MicroFormulator using NEMA-17 motors and plastic tubing to connect to the well plate. This instrument is designed to occupy one shelf of a standard incubator. FIG. 28D shows a rendition of the actual tubing network. Not shown is the means to raise the array of needles, connected by tubing the pumps and valves so that a well plate can be inserted underneath the needle array, which is subsequently lowered to add or remove fluid from each well. The needle array can then be raised to remove the well plate and replace it with another. The entire system shown in FIGS. 28A-28D can operate as an integrated instrument on one shelf of a conventional cell-culture incubator.

Figure 29A:
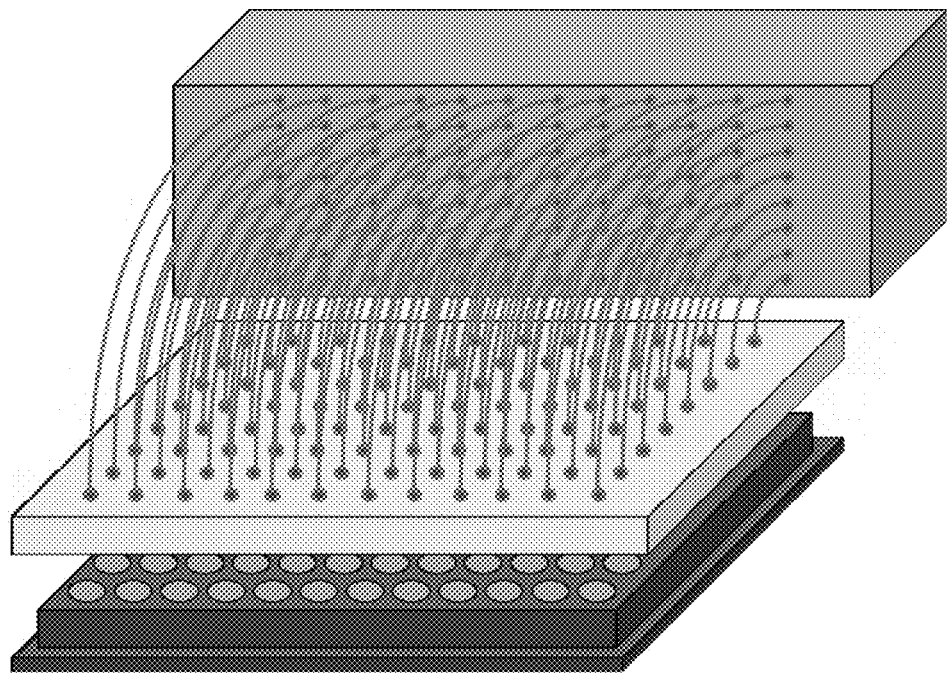
FIG. 29A shows connections of a remote controller to the single delivery/removal needle in each well of a 96-well plate according to embodiments of the present invention.
Figure 29B:
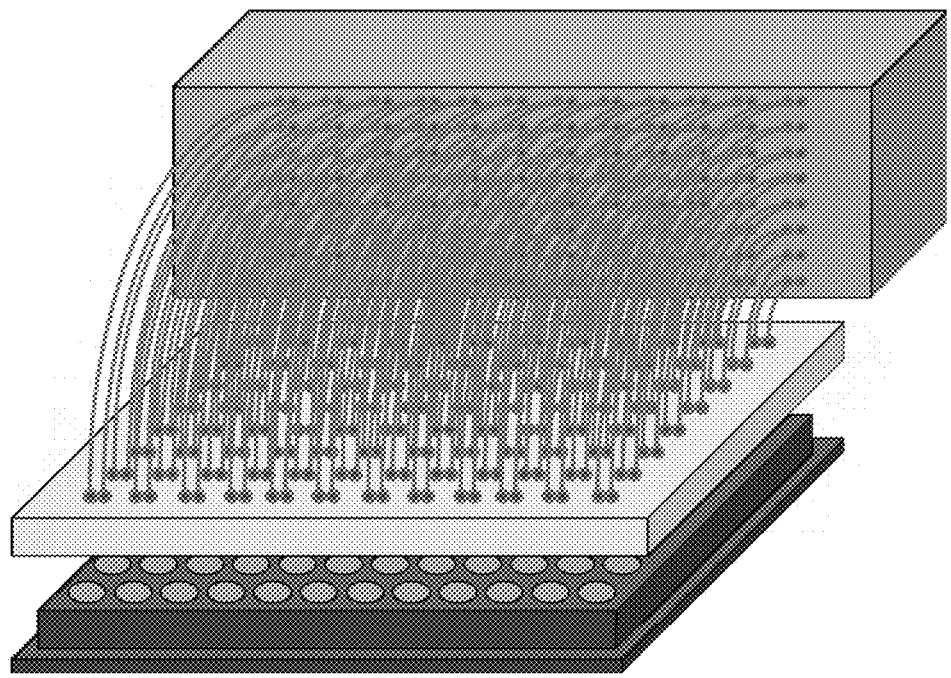
FIG. 29B shows connections of a remote controller to the dual delivery/removal needles in each well of a 96-well plate according to the embodiments of the present invention.

As shown in FIGS. 29A and 29B, the connection of a remote controller to the single delivery/removal needle in each well of a 96-well plate as shown in FIG. 22A requires 96 tubes. The use of separate delivery and withdrawal needles as shown in FIG. 22B requires 192 tubes, which complicates assembly and maintenance of the system. Hence there is merit in devising a means in which the fluidics for the pumps, valves, tubing, and needles can be integrated into a single, monolithic assembly or multiple simpler sub-assemblies.

Figures 30A, 30B, 30C:
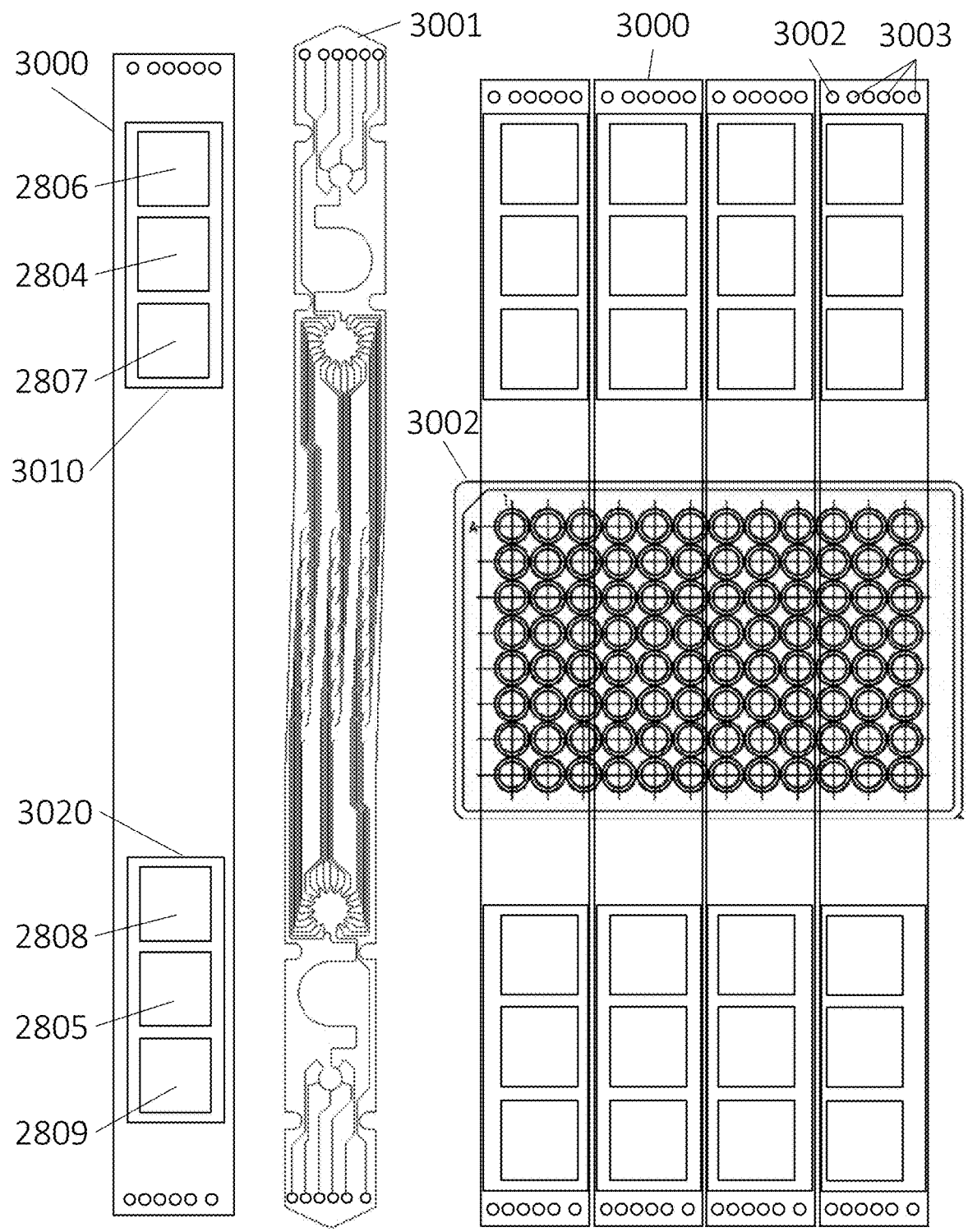
FIGS. 30A-30C show schematically reduction of the motors from twenty-four NEMA-17 stepping motors on a single frame shown in FIG. 28 to four microfluidic strips, each of which has six NEMA-8 stepping motors according to embodiments of the present invention.

FIG. 30 shows the benefits of reducing the motors from NEMA-17 stepping motors in FIG. 28 to NEMA-8 stepping motors. In this case, the six motors and all of the fluidics of a 24-channel push-pull module, i.e., a system 2800 shown in FIG. 28A, can be integrated into a single microfluidic strip, shown conceptually as a system 3000 in FIGS. 30A and 30C and more realistically as a strip 3001 in FIG. 30B. Four of these 24-well push-pull modules can be placed in parallel, such that the 12 motors on the delivery (push) side of the 96-channel push-pull MicroFormulator fit compactly along one edge of the well plate 3002, and the 12 motors on the removal (pull) side of the 96-channel push-pull MicroFormulator fit compactly along the other edge of the well plate. One end of the strip has a three-motor MicroFormulator delivery module 3010 and, at the other end, a three-motor MicroFormulator removal module 3020. The design in FIG. 30B shows six ports at either end of the fluidic strip. Five of these 3003 on the delivery (upper) end are for input fluids as in the MicroFormulators described above, while the sixth 3002 is directed towards a waste reservoir that is used in backflushing the pump 2804 and the input director valve 2807 through a twenty-fifth position of the input director valve. The sixth port at the lower, removal end of strip 3001 has the same purpose for washing the removal portion of the fluidic circuitry. Hence we demonstrate in this embodiment how to utilize 24 motors that populate four six-motor fluidic modules to address each well in a 96-well plate with both delivery and removal of fluid, and provide each well with a physiologically realistic PK drug exposure profile using time-division multiplexing.

The fabrication of the fluidic strip 3001 can be accomplished by a number of different microfluidic molding and fabrication technologies. A key point is that in the embodiment in FIG. 30B at least the portion of the fluidics that provide the microfluidic pump and valve capabilities needs to be fabricated from an elastomer. There are no viable ways to use standard subtractive machining to define the surface structure of elastomeric materials. Some techniques exist for additive machining but the resolution is low and high aspect ratio structures are difficult or impossible to achieve. Casting is the most efficient way to create structures in elastomers but it is often difficult to have a large range of feature sizes spanning 3-4 orders of magnitude in dimension in the same part. The current invention offers an intermediate casting step in order to realize complex structures in elastomers that can include different feature production methods and span as much as six orders of magnitude in reproducible structure dimensions.

To demonstrate the feasibility of this embodiment, a rigid master mold was first machined using standard machining technologies. This mold was used in combination with other molds to create an elastomeric secondary master mold that had the negative features of the desired pattern. This secondary elastomeric mold was then used in combination with other rigid and elastomeric molds to define the complex cavity in which the desired part was cast.

The use of primary and secondary masters/molds enables the hybrid soft/rigid casting of elastomeric materials to achieve complex monolithic shapes. Standard CNC machining techniques with ball end mills are used to create in rigid materials a positive of the fluidic lumen and other complex structures for casting the soft surfaces of the main mold. This includes holes that will become posts in the secondary mold that will form the holes for the inlet and outlet tubing and the holes for the well-plate delivery and removal tubes. Casting an elastomer on these machined layers creates the flexible secondary-mold whose surface is the negative of the desired complex structure. The flexible parts of the main casting structure are then held in a machined rigid frame while the next elastomer is cast in it.

By drilling holes into the primary mold, a negative of the lumen of a tube that is connected to a machined fluidic channel is created in the secondary master. A hole that coincides with the hole in the primary mold but somewhat larger is also drilled in the secondary mold forming a cylindrical cavity when the secondary mold is assembled with casting from the primary mold. The resulting structure is a cylindrical tube that extends perpendicular to the plane of the fluidic channel. Aspect ratios of greater than 15 to 1 have been demonstrated using this technique.

The ends of the posts that form the holes for the input and output tubing are threaded through close-fitting holes in the upper surface of the rigid casting frame that is used to form the top of the secondary mold, thereby avoiding the problem of membranes that seal vias in typical molds where the lid to a mold is pressed against posts.

The rigid casting frame may have some additional structure that allows for additional complexity in the finished casting. This additional structure may be machined into the rigid material or may be another elastomer layer. Using elastomeric materials as the molding surface allows for easy parting of complex structures that may include negative relief or high aspect ratio structures on multiple surfaces.

In the present form, a machined acetal layer is used to cast the elastomeric fluidic casting master by placing laser cut acrylic layers around the acetal in such a way as to confine all six sides of the structure. A hole cut in one end of the acrylic allows for the injection of the PDMS and another hole in the opposite end allows air to escape. PDMS must be completely degassed before injection into the mold to prevent formation of bubbles. The casting is then allowed to cure at room temperature for up to 16 hours to prevent heat-cure related shrinkage. After the room temperature cure, the mold is placed in a 60° C. oven for at least 6 hours to complete the cure. After the mold is allowed to cool, parting may begin. Once cooled, 2-propanol is used to ease the parting process by minimizing the autoadhesion of the PDMS to the mold surfaces. After parting from the initial mold, the elastomer part is vapor silanized with a fluorosilane and inserted into another laser cut acrylic molding frame where the process is repeated with the silanized elastomer replacing the acetal from the previous procedure. When demolding is complete, the new elastomer piece is dried thoroughly and cleaned with cellophane tape before plasma bonding to another PDMS part to complete the fluidic structure, as shown schematically in FIG. 31.

Figure 31A:
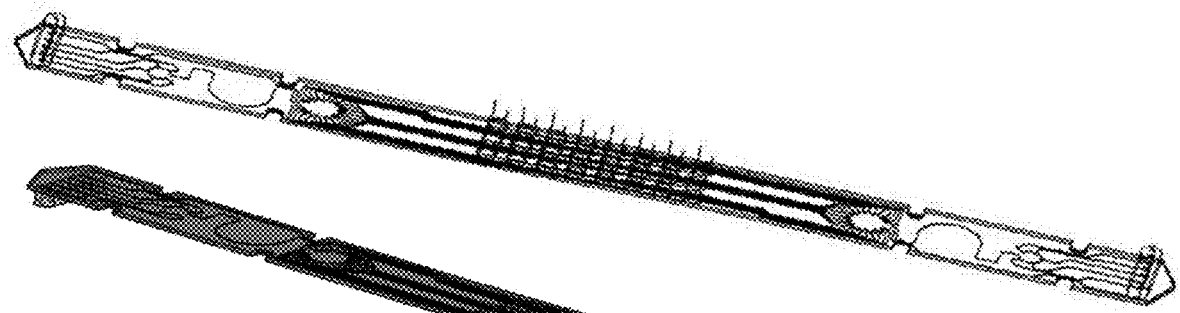
FIG. 31A-31C shows schematically multiple views of an integrated, 24-well, push-pull MicroFormulator elastomer fluidic circuit according to embodiments of the present invention.
Figure 31B:
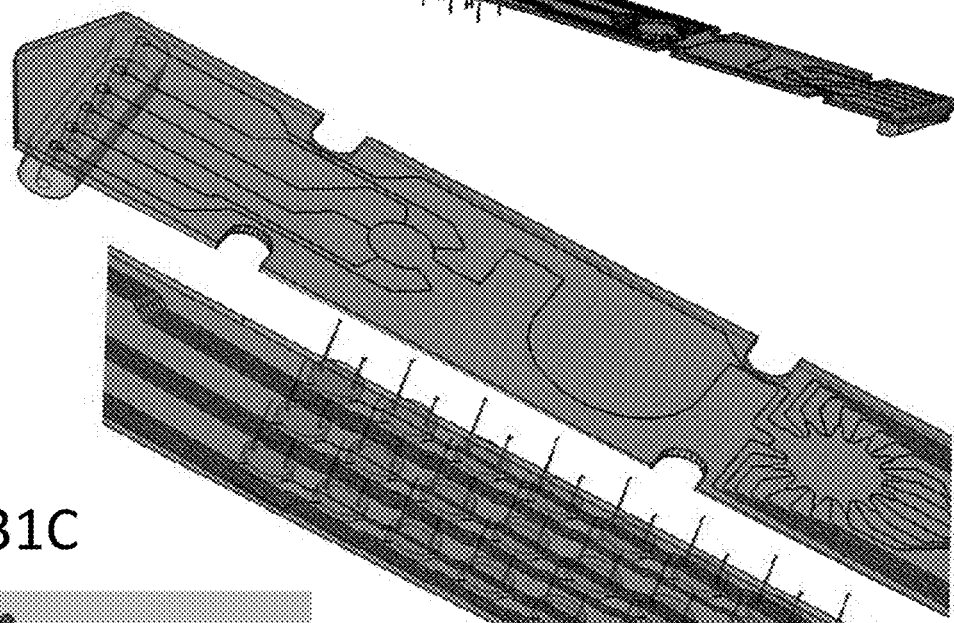
Figure 31C:
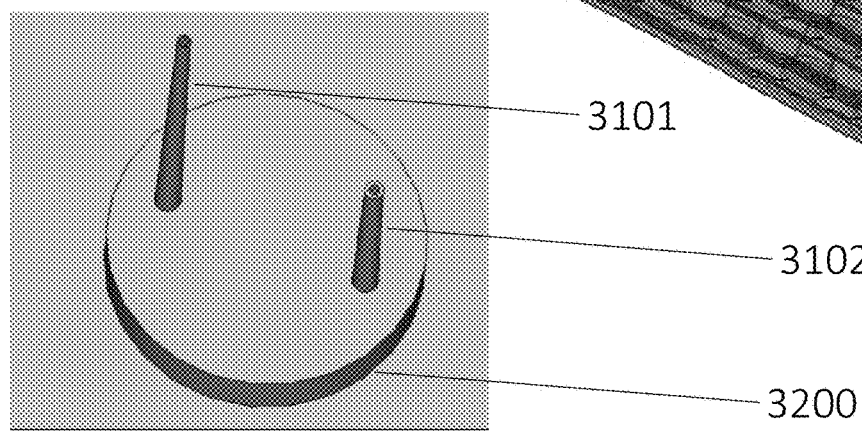

FIG. 31A shows wire-frame and perspective views of the complete elastomer piece. FIG. 31B shows close-ups of the RPV-RPPM-RPV fluidic circuitry at one end of the piece, and the needle array in the middle. FIG. 31C shows a close up of the long, hollow needle 3101 that reaches to near the bottom of the well, the shorter needle 3102 that can be used for either delivery of fluid or removal of fluid above the end of that needle, and the shoulder 3200 that locates the needles in the well.

The design shown in FIGS. 30A-30C allows for fluids to be added and subtracted to open-top fluid containers that use gravity to constrain the fluid. The design also allows for design adjustments to the access depth of the fluidic channel, therefore providing a means to have access to a fixed volume. By programming the depth of access in the chamber, minimum fluid levels of each access fluidic may be set.

Volume resetting procedures include pulling fluid from a fluid compartment until air is drawn into the fluidic channel, therefore resetting the fluid level to a fixed volume each time the procedure is performed.

Both sides may function as inputs and outputs. In one embodiment, the central interface is connected to a well plate, the depth of penetration of the interface being one-third and two-thirds of the working volume of the well, which allows volume resetting procedures to be performed at both volumes. This facilitates accurate dilutions and refilling procedures to be performed throughout experimental protocols.

A modular connection system allows interfacing to multiple device types from a single perfusion system. Direct connection to experimental fluidics as well as bubble traps and filters is possible.

Machine-programmable actuation surfaces allow the valve to be open through a sweep between angles or for only one angle of the motor. Complex fluidic circuits are possible and can allow recirculation, back-washing of filters, and reverse flow in selected segments of fluidics.

Channel widths may be selected based on fluid conduction requirements. Thinner channels will have a lower fluidic volume but increase fluidic resistance.

In the pump and valve region of the fluidic circuit 3001, the compression-zone channel segment dimensions are dependent on the compression actuator size.

Hence, in one aspect, the present invention relates to a molded fluidic module that allows access to a multitude of chambers, vials, wells or other fluid compartments is fabricated using the multi-surface elastomeric molding process described above. The resulting device has structures that allow a direct interface with existing or custom-designed fluidic chambers. In one embodiment, the device is interfacing with one-fourth of a 96-well plate. The approach could be readily extended to any configuration of a well plate, including the addressing of one or two tubes on both sides of a each well and transwell in a transwell plate, in which one pair of tubes controls fluid delivery and removal in each transwell insert, while the second pair of tubes controls fluid delivery and removal in the well beneath each insert.

It would also be possible to fabricate the requisite fluidics by utilizing multiple flat layers bonded sequentially or simultaneously to define the fluid channels. Ultimately, all or part of the fluidic circuit 3001 will be fabricated by injection molding, thereby reducing the cost to the point that the fluidics will be considered disposable and readily exchanged by disconnecting the drive motors and actuator heads (3010 and 3020 in FIG. 30) from the fluidics by a latching mechanism. Note that the delivery tubes and needles for each well could be an integral part of the single disposable microfluidic device, or the delivery tubes and needles could be an integral part of the well plate itself, with the microformulator fluidic circuitry then connecting to an interface connector that is part of the well plate.

At present, the control of each of the stepping motors is performed by a microprocessor-enabled control unit that includes the stepping motor driving electronics. Ultimately the three motors at each end of the 24-channel module (3010 and 3020 in FIG. 30) will be controlled by a shared SmartMotor controller board that includes a wireless communications controller, a microprocessor to interpret commands to the unit and to sense and transmit as required the encoded position of each motor, and three microprocessors that control the delivery of stepping commands to each motor through a stepping-motor driver circuit. The use of wireless control of the motors would eliminate the need for a control tether. An incubator docking station could provide the DC power to drive the pumps and valves in either the incubator or other stations. A rechargeable battery within the lid could provide power to the system while in transit between incubator and other stations.

Given that only the region of the fluidic circuit 3001 immediately beneath the six motors needs to be elastomeric, it will be possible to fabricate the needle array by mass-producible injection molding of either polystyrene or cyclic-olefin copolymer or another material, thereby minimizing the use of elastomers in the system to reduce drug and toxin uptake by the elastomer. Initially, devices have been made using the elastomer PolyDimethylSiloxane (PDMS), but they could be produced using other materials such as Sty-rene Ethylene Butylene Styrene (SEBS), which is less prone to the absorption of hydrophobic drugs, hormones, metabolites, and other molecules.

FIGS. 32A-32C shows one such means to implement a mass-produced needle array that provides push-pull fluidic access to each well in a 96-well plate. As shown in FIGS. 32A and 32B, the fluid level 3203 would not exceed the level set by the short needle 3202 and would not be less than the level of fluid 3205 set by the long needle 3201. The needles would be located in the well by means of a shoulder 3200. FIG. 32C shows how the needle arrays required to push-pull address all wells in a well plate could be created using a set of 12 parallel, planar needle arrays 3205, each of which has eight needle pairs that couple to a single row of eight wells 3206 in a 96-well plate. The needle array itself is, in this embodiment, created by bonding together a central planar section 3207 (FIGS. 32D and 32E) that has the microfluidic channels on each side, which can be produced either by injection molding or hot embossing, for example in polystyrene. The channels on each side are sealed by a thin planar layer 3208 (FIG. 32D) that need not have channels and can be bonded to the central section 3207 (FIGS. 32D and 32E) by either ultrasonic welding, thermal bonding, or adhesive. The 12 strips 3205 shown in FIG. 32C can in turn be connected to the pump and valve fluidics to create four 24-well modules 3000 shown in FIG. 30C by means of flexible fluidic strips that include the pump and valve fluidics, or by flexible connector strips (not shown) that couple the needle array to the pump and valve fluidics.

Channels within these laminar versions may be embossed, etched, molded, or laminated on any of the surfaces. Once the pieces are bonded together, the fluid channel is formed between layers.

Fluid ports at the end of each needle may be configured to allow liquids to flow into and out of the bottom of the needles at any desired angle; this may be appropriate when adding fluid at high rates into compartments where cell culture is performed and it is desirable to avoid damaging the cell by direct impact by rapidly flowing fluid.

Figure 33A:
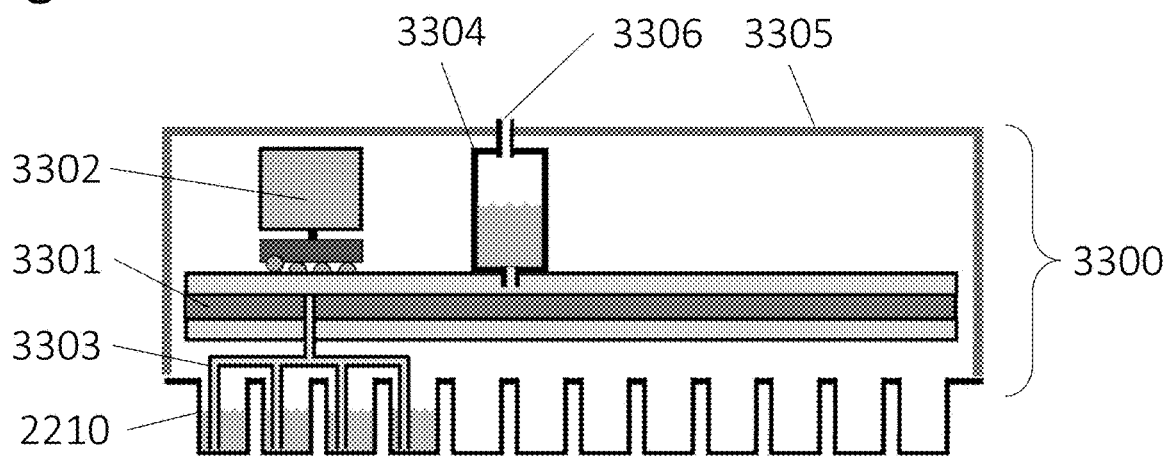
FIGS. 33A and 33B show the fluidic network supported on a planar substrate having the pumps' and valves' motors and fluid reservoirs above the substrate and the needles below according to another embodiment of the present invention.
Figure 33B:
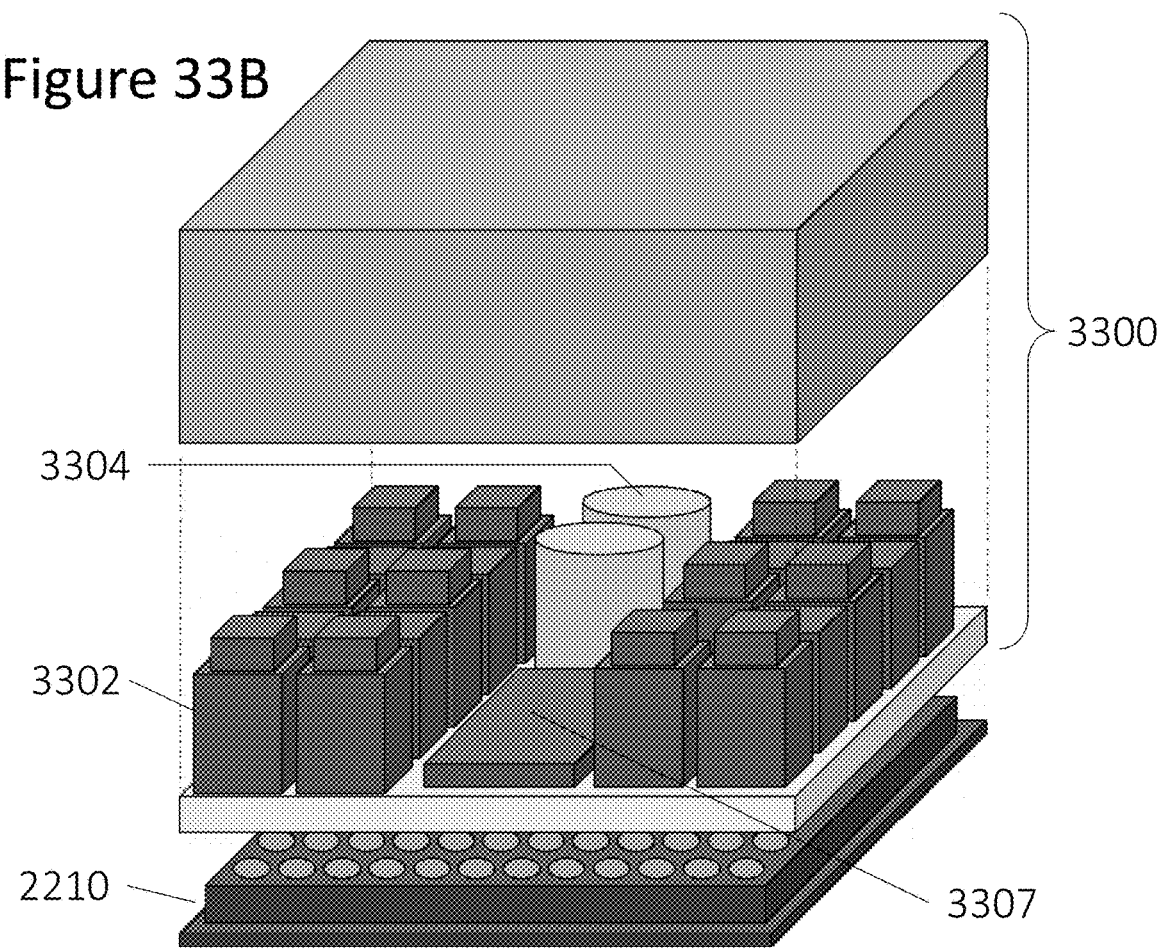

In another, more compact embodiment shown in FIGS. 33A and 33B, the fluidics would be supported on a planar substrate 3301 that would have the pumps and valves motors 3302 and fluid reservoirs 3304 above the substrate, and the needles 3303 below. The fluidic channels in that substrate could be on the top side or the bottom side of the substrate, or both.

The pump heads could be either above the substrate, which would require fluidic vias through the plate for each needle as shown, or the pump heads could be below the plate (not shown), which would only require holes for the shafts. Alternatively, the pump heads below the substrate could be driven magnetically from magnetic rotors above the substrate (not shown). The entire unit could be enclosed by a cover 3305 that provides a hermetic seal around the control electronics 3307 and motors 3302, with external vents or ports 3305 to provide access to internal fluid reservoirs 3304. This approach obviates the need to provide strain reliefs for tubing connected to fluid reservoirs.

If all of these pumps and valves were placed within a covered lid of the well plate, and the pumps and valves controlled wirelessly, then the assembly of the MicroFormulators with pumps and valves, reservoirs, and control electronics could be handled as a single unit, termed a Smart Lid 3300.

If a well plate is 96 channels, which is 8×12 wells, then one could make a Smart Lid that was divided into two 4×12 sections, each with a pair of 24-port valves as described above. The Smart Lid could have gas and vacuum reservoirs, or connections to a bus that provided access to vacuum or pressurized gas, possibly using the sterilizable interconnect system described above.

The pumps used in the present invention can be, for example, rotary planar peristaltic micropumps (RPPMs), more conventional peristaltic pumps, piezoelectric diaphragm pumps with check valves, Quake pneumatic pumps, or other pumps with the requisite pumping rates and delivery pressures. Alternatively, pneumatic pressure or suction delivered to each reservoir could be used to control fluid delivery and withdrawal, respectively.

As pumps and valves get even smaller, it will eventually be possible to apply these principles to individual wells. The demonstration of the approach to sets of four wells in some of the examples above is simply in recognition of the present capabilities and is in no way meant to represent a limitation to the power or flexibility of the approach.

The valves used in this can be, for example, rotary planar valves, Quake valves, Mathies valves, TURN valves, TWIST valves, solenoid valves, rotary HPLC-type valves, diaphragm valves, or other valves that provide the requisite functions. Normally closed valves would minimize the power requirements.

A Smart Lid docking station could include electric power, vacuum, pressurized gas, or other types of interface and control connections.

Sensors incorporated into the Smart Lid might include, but not be limited to, the measurement of flow rate, pressure, temperature fluid volume/level in the well, concentrations (e.g., glucose, lactate, pH, oxygen, etc.), cellular fluorescence or other optical, mechanical, electrical or chemical readouts of the fluids being controlled within the Smart Lid, or in the wells, or within the cells being cultured in the wells. Sensors for tilt, rotation, and/or acceleration would provide quality control information.

The Smart Lid could have bar-code identification and/or wireless electric identification to facilitate control, storage, and retrieval of multiple units.

The Smart Lid can be used to control the gas mixtures ($O_2$, $CO_2$, $N_2$, etc.) above the well plates, either for the entire well plate or sub-zones.

Support fluidics within the lid could include bubble traps, debris filters, sampling ports or channels, compliance chambers, and in-line sensors such as those listed above. Sensors could determine whether bubble traps or debris filters needed to be emptied.

The use of metering pumps, such as the RPPMs, and appropriate control software will allow the determination of the volume of fluid in each channel segment, tube, and needle, and this information can be used to control fluid delivery, line washing, and other fluid control functions.

Controlled removal of sample for off-line analysis can be accomplished by using the pumps and valves to transfer selected volumes of fluid either to empty wells, or to vials contained within the Smart Lid.

The present invention would thereby provide users of conventional well plates with the ability to control the delivery and sampling of fluids in the wells of a well plate with a level of temporal control heretofore not possible.

The control electronics and mechanisms within the lid could be hermetically sealed to simplify sterilization.

A washing station could be used to cleanse the interior and exterior of all surfaces in contact with either the well plate or the fluids within it, either prior to first use or during the transfer of the lid from one well plate or well plate zone to another.

A sterilizing station could use solvents, detergents, UV light, gamma rays or other standard sterilizing techniques to sterilize the Smart Lid.

The Smart Lid can contain a key that matches the corner on a standard well plate to ensure proper alignment of the Smart Lid with the underlying well plate.

The motors that drive the pumps and valves can either be stepping motors, DC gear-head motors, brushless DC gear-head motors, or other motors. The motors could either be conventional motors with external controllers, or smart motors with integrated microcontrollers and position/velocity encoders.

The computer software operating either in the microcontrollers within the Smart Lid or in an associated computer would perform functions such as pump speed and duration of fluid delivery, valve position, sensor output, input to mechanical, electrical, optical or chemical actuators built into the lid, all in a user-definable sequence or protocol. The software would log all steps in protocols and all error reports, and operating conditions as desired, and support storage and retrieval of protocols to allow accurate repetition of operations in a series of experiments.

The microcontrollers on the Smart Motors or within the Smart Lid would record all key information to support the record keeping required for Good Manufacturing Practice (GMP), Good Laboratory Practice (GLP), and other procedural standards, including the storage of log and error files.

The Smart Lid could be designed to interface with a standard 96-well plate, standard plates with fewer or more wells, or custom plates that were optimized for mechanical and fluidic interface to the Smart Lid.

The filling and emptying of the individual wells can be tracked by the computer software that operates the pumps and valves. In the current embodiment, the µF-96 is being run by our Automated Multi-Pump Experiment Running Environment (AMPERE) software (FIGS. 34A-34D). This program has the capabilities to command single motors and valves as a function of time (FIGS. 34A and 34B), track the volume of fluid and/or the concentration of a drug as a function of time (FIG. 34C), and control the filling and emptying of individual wells or groups of wells (FIG. 34D.

Figure 35:
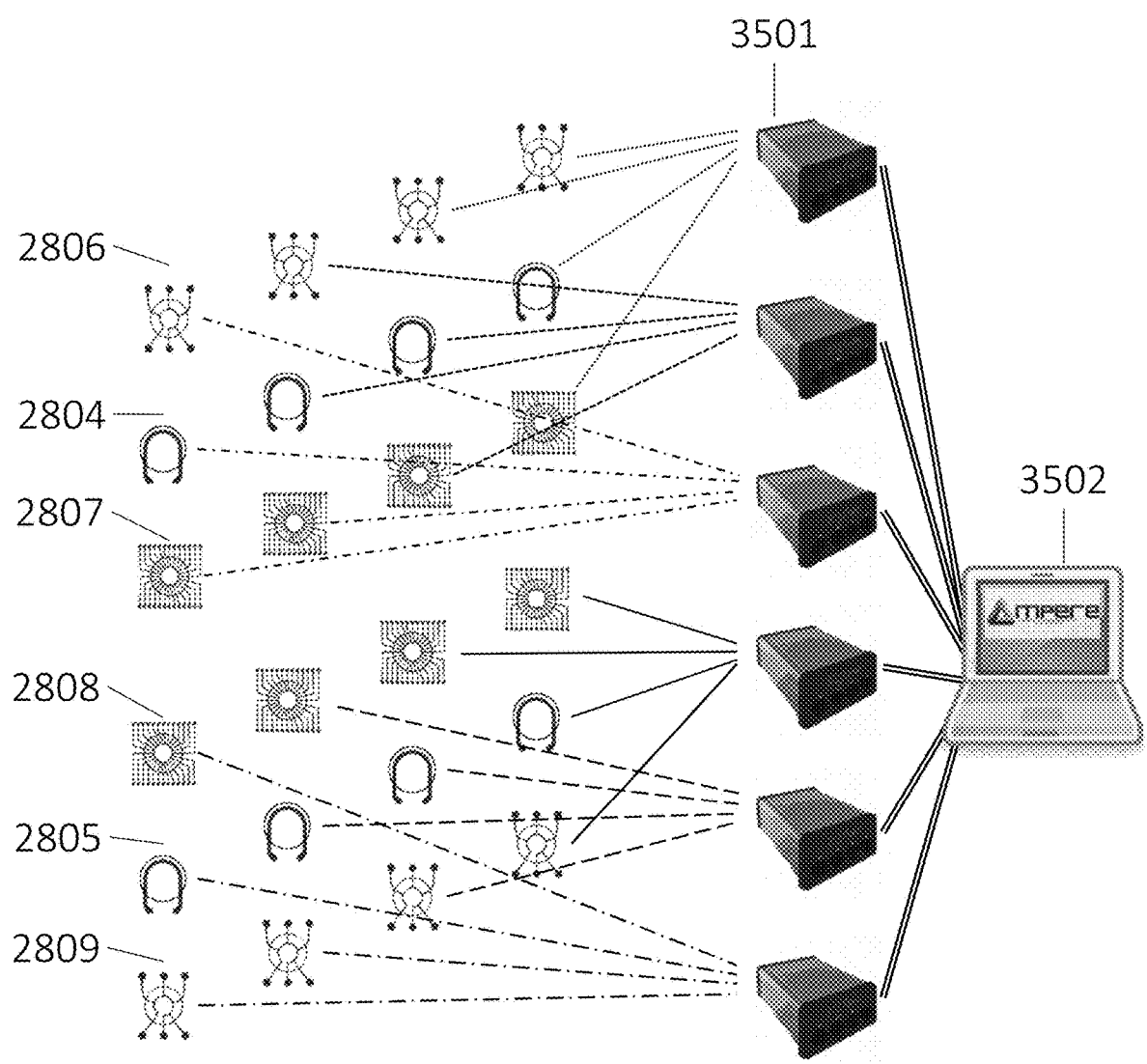
FIG. 35 illustrates an embodiment of connections between the various MicroFormulator components shown in FIGS. 28B, 30A, and 30C, wherein a four-channel motor microcontroller provides the hardware interface between the stepping motor and the notebook computer that runs AMPERE.

FIG. 35 illustrates the connection between the various MicroFormulator components shown in FIGS. 28B, 30A and 30C, wherein a four-channel motor microcontroller provides the hardware interface between the stepping motor and the notebook computer that runs AMPERE. In this example, there are eight five-port valves 2806 and 2809, eight RPPMs 2804 and 2805, and eight twenty-four-port valves 2807 and 2808. In groups of four, these 24 devices are connected to six four-channel microcontrollers 3501 that support the communication between the motors and their encoders and the notebook computer that runs AMPERE 3502. AMPERE supports the construction of detailed commands to each microcontroller that governs the position and velocity of each stepping motor. In the future, the four-motor wired microcontrollers 3501 will be replaced by three-motor wireless Smart Motor boards. Hence in the current embodiment, the 96-channel push-pull well plate MicroFormulator/Smart Lid system includes 24 devices connected to 6 controllers. AMPERE is used as the interface to command the controllers. With Smart Motors, there will be eight sets of three motors.

The difficulty is designing protocols while synchronizing the eight 24-port valves, the eight pumps, and the eight five-port valves. Therefore, a tool is needed to orchestrate basic well plate commands. The tool will be able to be configured based on the hardware available and submit higher level commands to the individual devices to perform the appropriate operations. These commands can be bundled into protocols which can be saved, loaded, or scheduled. However, there is still complexity with creating well plate protocols from a user perspective. Macros can be employed that take user inputs and generate customized protocols. This will allow the user to easily create complex experiments without having to delve into the engineering level of controls.

Figure 34A:
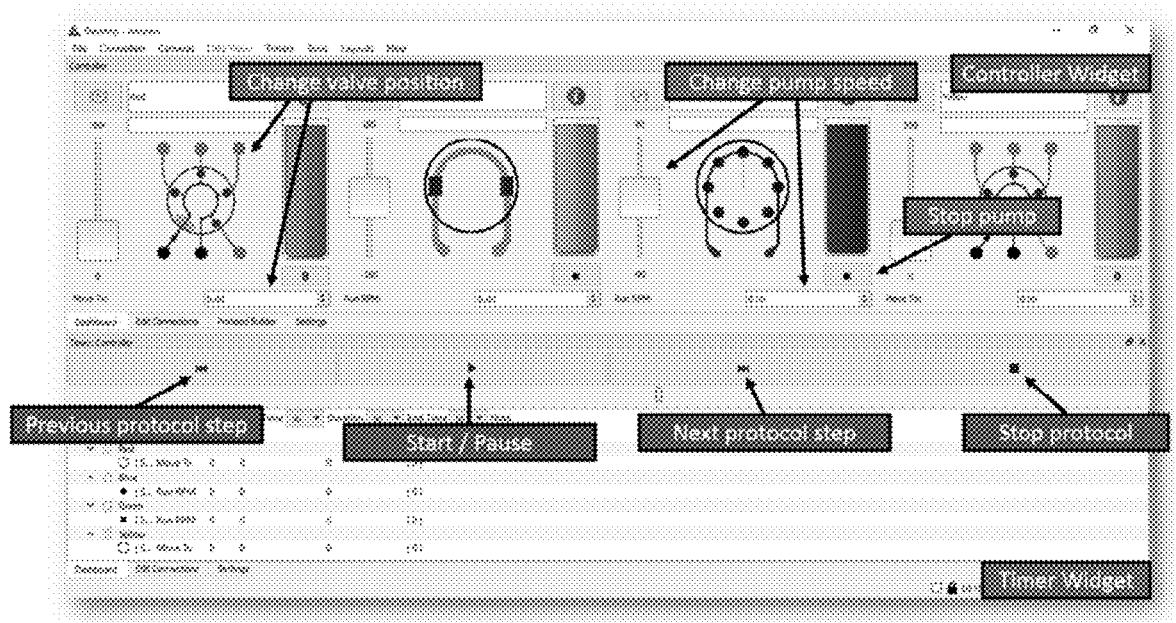
FIGS. 34A-34D show snapshots of Automated Multi-Pump Experiment Running Environment (AMPERE) software for the µF-96 according to one embodiment of the present invention. This program has the capabilities to command single motors and valves as a function of time (FIGS. 34A and 34B), track the volume of fluid and/or the concentration of a drug as a function of time (FIG. 34C), and control the filling and emptying of individual wells or groups of wells (FIG. 34D).
Figure 34B:
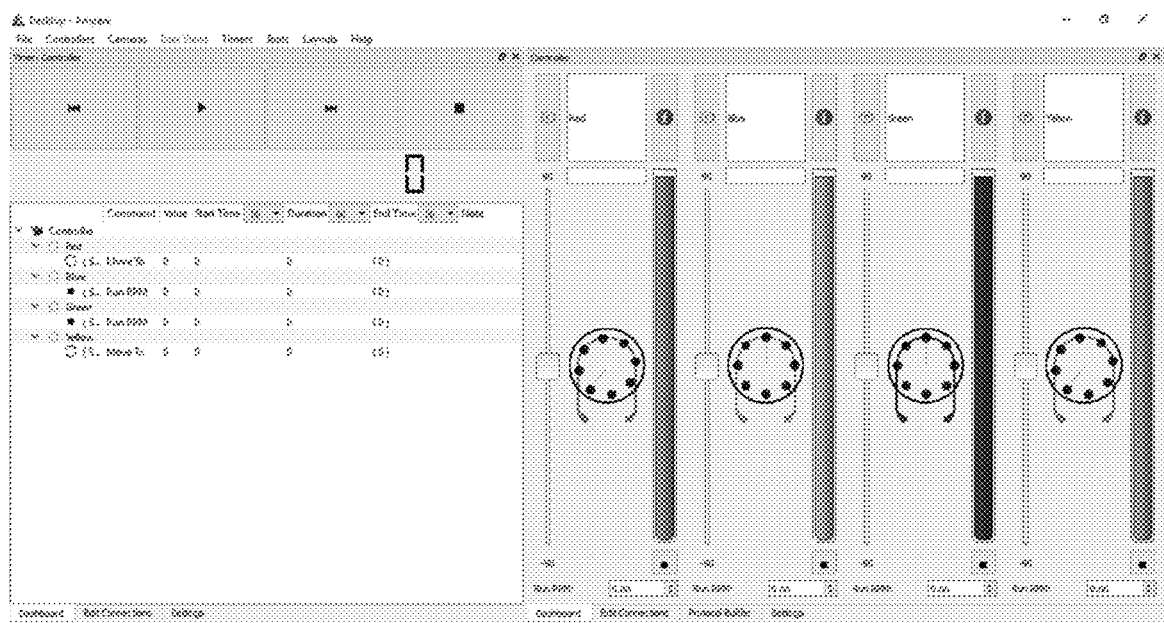
Figure 34C:
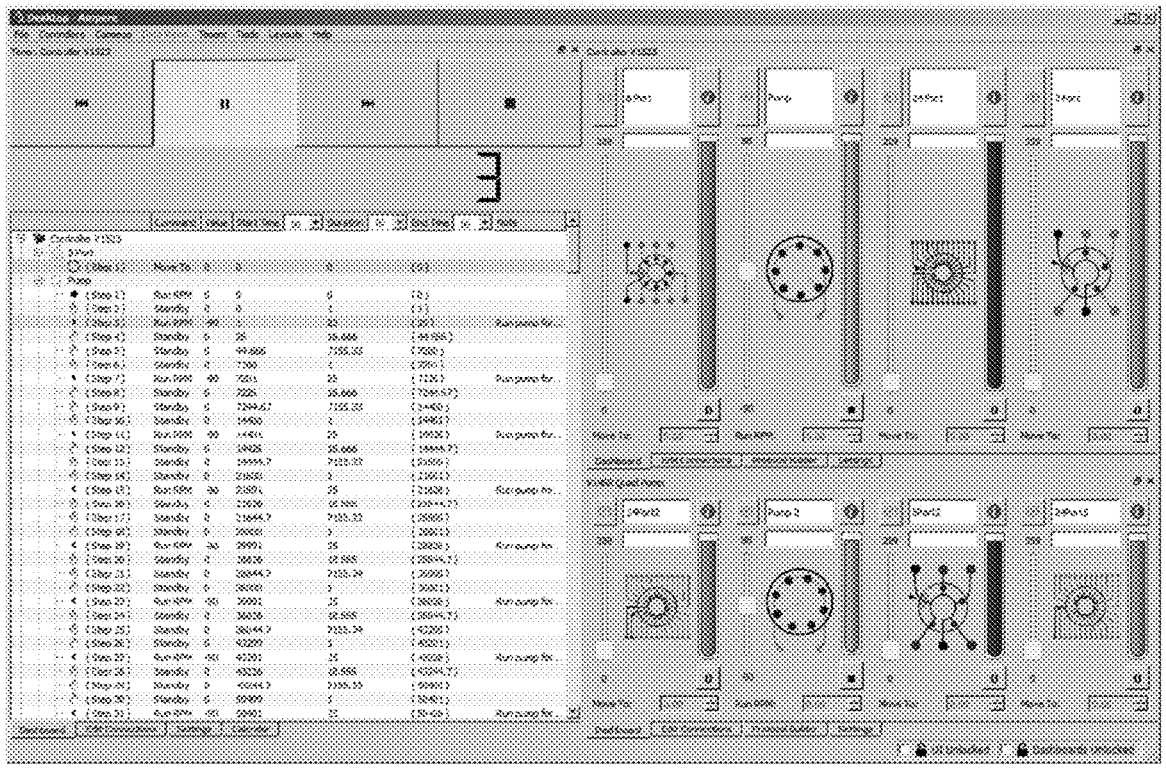
Figure 34D:
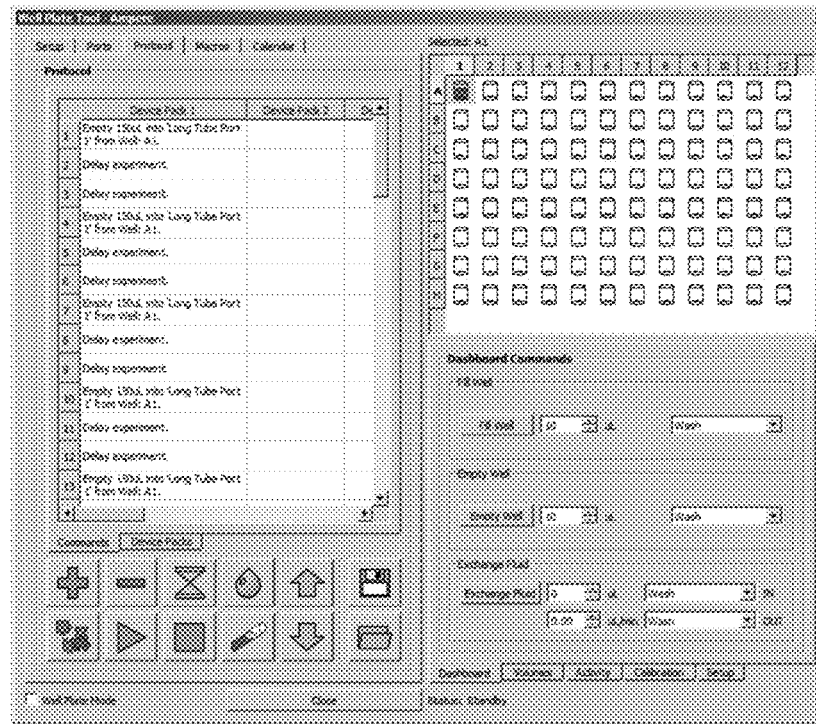

In a hierarchical command structure, AMPERE supports the construction of detailed commands to each microcontroller that governs the position and velocity of each stepping motor at customizable time points. The Well Plate Tool within AMPERE provides higher-level commands such as "Fill Well," "Empty Well," "Wash Tubing," "Prime Tubing," "Delay," which are then translated by AMPERE into specific sequences of motor commands that are then sent to the microcontrollers, for example in either a motor control module or in the Smart Motor electronics. These commands can be constructed in the tool to work in sequential steps. Lists of these commands can be saved into protocols, after which, the protocols can be loaded for a single use or scheduled to run at a particular date and time. Through biologist friendly interfaces, macros can be used to generate the complex protocols for the user. One example of a macro is one that would generate a protocol that will perform a drug delivery that achieves a specific pharmacokinetic (PK) dosing profile based on the parameters instructed by the user. This macro allows for customizable PK dosing profiles for individual wells. It will be possible to specify drug delivery to achieve a specific pharmacokinetic (PK) dosing profile, for example by selecting "Oral" or "Intravenous." Clicking and dragging will allow selection of particular sets of wells for a chosen PK dosing profile. FIG. 34A shows the AMPERE graphical user interface (GUI) for controlling individual pumps and valves. FIG. 34B shows a list of commands to drive four pumps as desired. FIG. 34C shows the GUI for operating three five-port valves, three twenty-four port valves, and two pumps. FIG. 34C shows the well-plate tool's graphical representation of fluid type and level in each well and the GUI that allows for customizable PK dosing profiles for individual wells. With the appropriate tubing connections between input selector and output director valves, AMPERE could be used to control fluid removal from one well and its delivery to another well. If the µF-96 is used to deliver drugs or hormone mixtures to another well plate or a coupled system of multiple organs-on-chips, AMPERE can be used control hormone, drug, or nutrient concentrations in these organs or wells.

This same approach can be used to configure, control, and interconnect multiple Perfusion Controllers, MicroClinical Analyzers, and MicroFormulators.

In summary, VIIBRE's long-term development of compact, low-cost microfluidic pumps and valves to support a number of Tissue Chip/MicroPhysiological Systems has led to the development of a new technology that supports a new level of temporal control of media and drug concentrations in each well of a 96-well plate. Whether for conventional well-plate biology, pharmacology, toxicology, and systems biology, or for the control of differentiation of induced pluripotent stem cells for medicine and tissue regeneration, the ability of VIIBRE's MicroFormulators to control concentrations without removing a well plate from an incubator and placing it underneath a fluid-handling robot will lead to new advances in biology and medicine. In essence, our μF technology is bringing the robot to the well plate, in contrast to the current practice of bringing the well plate to the robot. VIIBRE's current short-term objective is to reduce the cost and increase the ease of use of these devices to make them an invaluable contribution to biology and medicine.

EXAMPLE III

Devices for Fluidic Control within and Between Engineered Tissue Constructs, Microbioreactors, and Well Plates This example discusses how the previously described invention can be modified and optimized for the control of fluids as specifically required for the long-term culture of cells in tissue chips or organs-on-chips, which can be thought of as two- or three-dimensional microbioreactors for culturing adherent or non-adherent cells with and without a supporting matrix.

Figure 36:
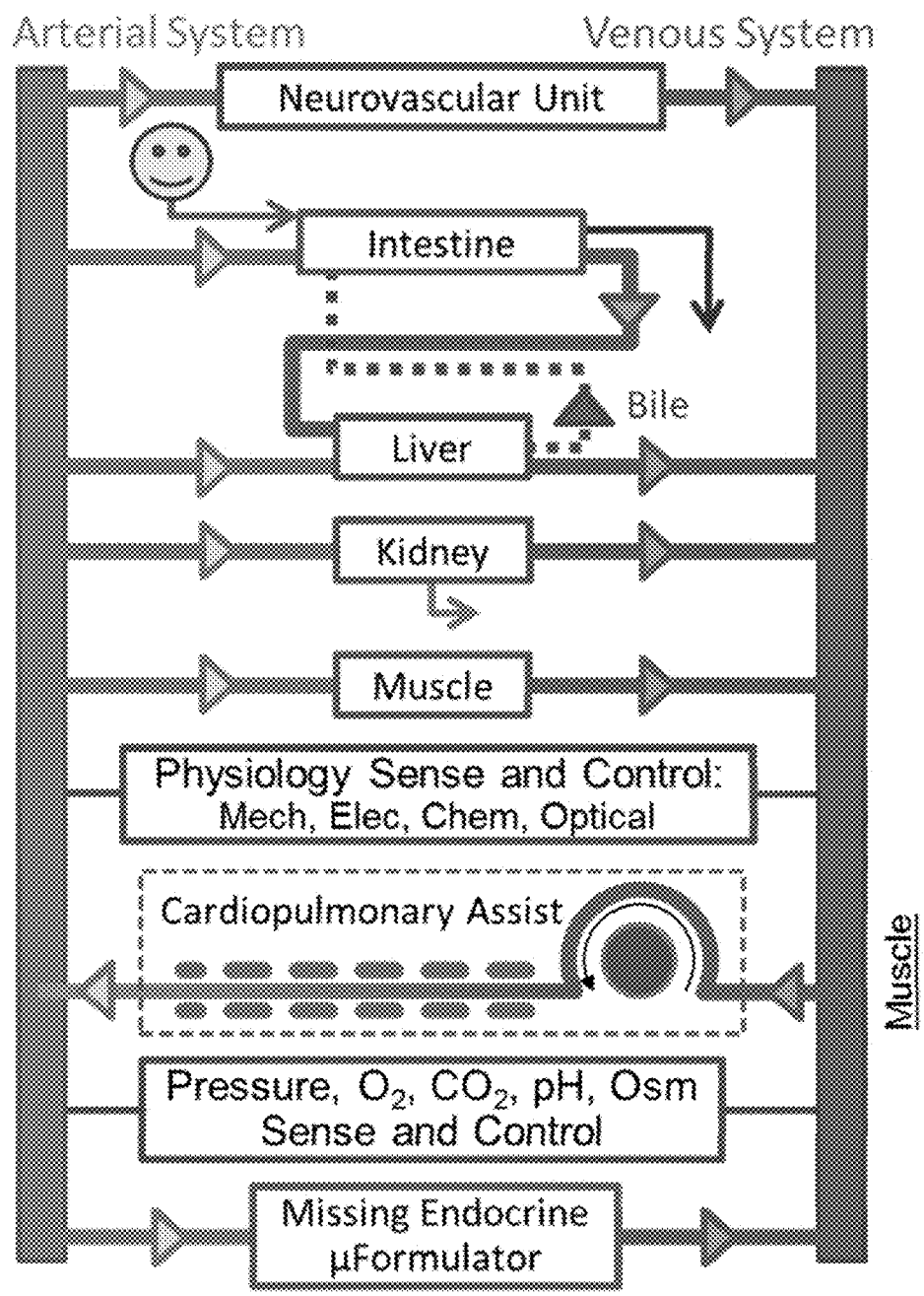
FIG. 36 shows schematically a coupled-organ microphysiological system (MPS) according to one embodiment of the present invention.

As organs-on-chips are being coupled together, there is a need for a missing endocrine organ-system MicroFormulator that can provide endocrine control for the integrated organs-on-chips described above. FIG. 36 shows the schematic layout for one such system, which includes a neurovascular unit/blood-brain barrier, a liver, a kidney, and skeletal muscle. The control and sensing functions can be provided by the various modules, for example as described in FIG. 17. To put this in perspective, we are developing an in vitro, three-dimensional, multi-compartment, organotypic model of a human neurovascular unit (NVU) that includes a neural compartment coupled to a realistic blood-brain barrier (BBB). The BBB model is being used with the multimodal instrumentation and analysis platform described above to examine the role of the BBB in modulating chemical body-brain interactions, to characterize the interactions of glia, astrocytes, pericytes, endothelial, and neural cells in the brain and its barriers, and to assess the effect of a wide range of drugs, chemicals, and xenobiotics on the brain. The current and predicted clinical use of this model rests on its versatility to accommodate cells (e.g., brain endothelial cells) from patients with known pathologies who are (or not) exposed to a drug treatment. The clinical viability of the BBB model used has been shown in rigorous comparison studies against human brain in situ. The BBB system in its entirety will reveal neurotoxicity of drugs that are either currently used or considered for Phase 1 trials. The final BBB will support high-content screening. This research will offer novel and unbiased views of the correlations between large numbers of chemical signals in and to the brain, enabled by a powerful combination of (1) microfluidic devices; (2) state-of-art cell-culture and organotypic human brain-cell preparations; (3) analytical instruments such as miniature electrochemical sensors and an ion mobility-mass spectrometer (IM-MS); (4) computational bioinformatics techniques; and (5) control theory that is needed to regulate the coupled organ systems.

FIG. 36 is typical of the coupled-organ microphysiological systems (MPS) under development: it has no endocrine system. Hence these tissue-chip (TC) Homunculi have neither user-controlled levels of circulating hormones nor daily oscillations in concentrations of hormones, nutrients, or metabolites. Given the growing recognition of the significance of circadian rhythms in drug responses, it is of concern that so little attention is being paid to either endocrine regulation or circadian rhythms in either TC Homunculi or more standard in vitro, cell-based high-throughput studies of drug efficacy and toxicity. The present invention addresses this missing-organ problem using the Missing Endocrine Organ-System MicroFormulator (MEOS-μF) to create time-varying hormone concentrations in a TC Homunculus and determine whether these temporal variations affect Homuncular metabolism of a drug or toxin under test. If this breakthrough MEOS-μF technology allows us to demonstrate such effects in vitro, it will open the door to a breadth of studies in chronotherapy and chronotoxicity that heretofore could only be performed in animals. More important, the anticipated low cost of the MEOS-μF will make it possible to add endocrine function to patient-specific Homunculi, for example in a study of cancer metastasis and drug metabolism tailored to a particular patient's tumor using a liver-brain TC model derived from the patient's induced pluripotent stem cells (iPSCs), without the need to create individualized endocrine organs from iPSC cells. The MEOS-μF, with its ability to perfuse individually each well in a 96-well plate, could also allow exquisite temporal control of hormone, nutrient, and metabolite levels in well plates used for either conventional planar cell cultures or organoid models. This device will enable the recapitulation of the effects of important endocrine organs missing in most TC Homunculi, not with actual TC organs, but with a microfluidic device that allows us to explore at will the effect of both steady and time-varying hormone levels on the response of TC Homunculi to drugs and toxins.

Figure 37:
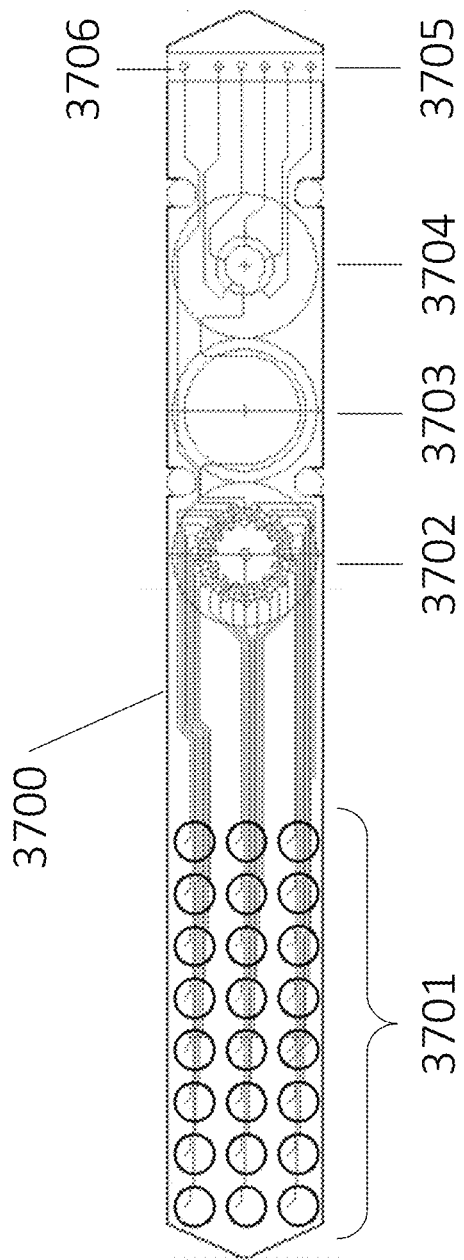
FIG. 37 shows schematically a microfluidic device configured to select hormones, nutrients, or drugs from any of twenty-four wells, and deliver them to five organ chips or reservoirs while allowing temporal control of concentrations through time-division multiplexing according to one embodiment of the present invention.

We now show how the 24-channel and 96-channel MicroFormulators (μF-24 and μF-96) described above (FIGS. 24, 28, and 30) can be modified to create a Missing Endocrine Organ-System MicroFormulator (MEOS-μF) that can be used to deliver, under time-division multiplexing, a time-varying formulation of nutrients, hormones, small signaling molecules, and drugs to recreate not only the PK temporal profile of drug delivery from either intravenous or oral dosing, but also recapitulate the diurnal (circadian) rhythm of both hormones and human activities. The microfluidic device 3700 shown in FIG. 37, derived from the 24-channel fluidic strip in FIG. 30B, would then allow the delivery, over the course of a one-month trial, time-dependent combinations of up to 24 nutrients, hormones, vitamins and drugs to reconstruct known hormonal circadian rhythms with at least hourly temporal resolution. The desired hormones would be stored in 24 hormone storage wells 3701, selected by a 25-port hormone selector valve 3702, pumped by the integral RPPM 3703, and then directed to the appropriate organ-chip by a five-port organ selector valve 3704. The chosen hormones or their time-division-multiplexed combination would then flow to the selected organ out of the five ports 3705. The sixth output port 3706 would be used with the twenty-fifth position of the valve 3702 for washing the valves and sending to waste any unused hormones stored in the pump and valves.

This system would then be able to provide different steady levels of the hormones, as well as levels that fluctuate in a physiologically realistic manner. This approach can then be used to examine the effects of circadian rhythms in hormone and nutrient levels on the metabolism and efficacy of a wide range of drugs and toxins, effects that are recognized but not well studied. One could make a reasoned argument that cell biology using immortalized cells cultured as monolayers on plastic in high glucose media is in fact studying cancerous, fat, lazy cells that gorge on food once a day, don't exercise, don't sleep, and do not experience fluctuations in thyroid, stress, sex or other hormones. Similar problems exist in the study of tissue chips and organs-on-chips. The Missing Endocrine Organ-System MicroFormulator addresses some of these limitations.

Figure 38:
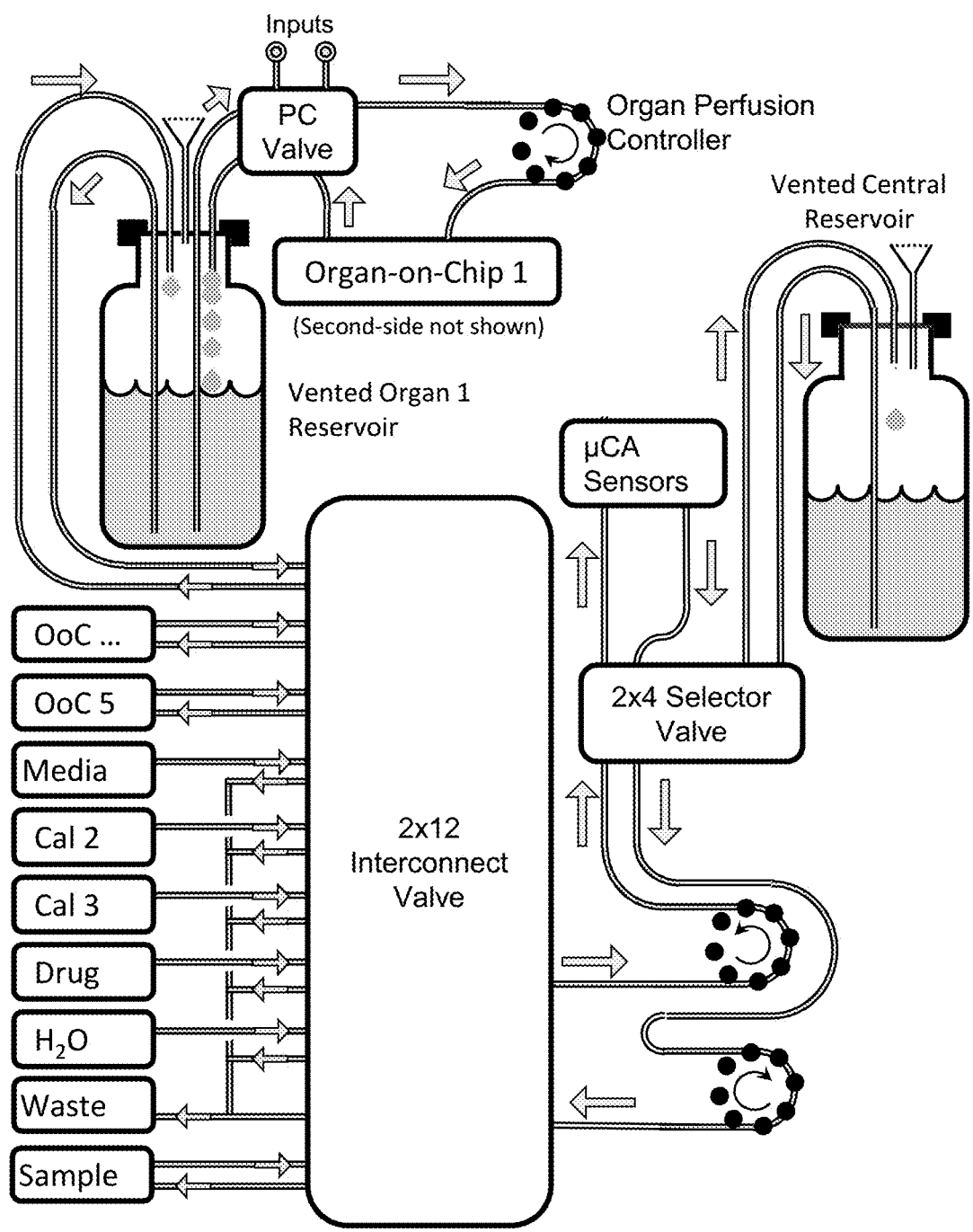
FIG. 38 shows a system used to study the interaction of organs-on-chips according to one embodiment of the present invention.

FIG. 38 shows a system used to study and control the interaction of multiple organs-on-chips. In the exemplary embodiment, central to this design is the use of a local Perfusion Controller for each organ, and a shared central reservoir. The functions shown in this design can be accomplished with integrated microfluidic modules derived from the three-motor fluidic strip described in FIG. 30B. This system allows control of local organ recirculation, including flow rate, local reservoir volume (which could be reduced with time), fluid replacement rate (which could increase with time). It also supports global mixing with the central reservoir using time-division multiplexing of fluid exchange to each organ. This can be used to compensate for nonuniform organ size, and will allow control of the global fluid replacement rate, the addition of media to replace withdrawal to waste or sampling, and the addition of H$_2$O to replace evaporation. It will allow control of the volumes of fluid in each organ, the vascular fluidic system, and any vascular or other reservoirs. It can be extended to include bubble traps and debris filters, either at the organ or system level.

Figure 39A:
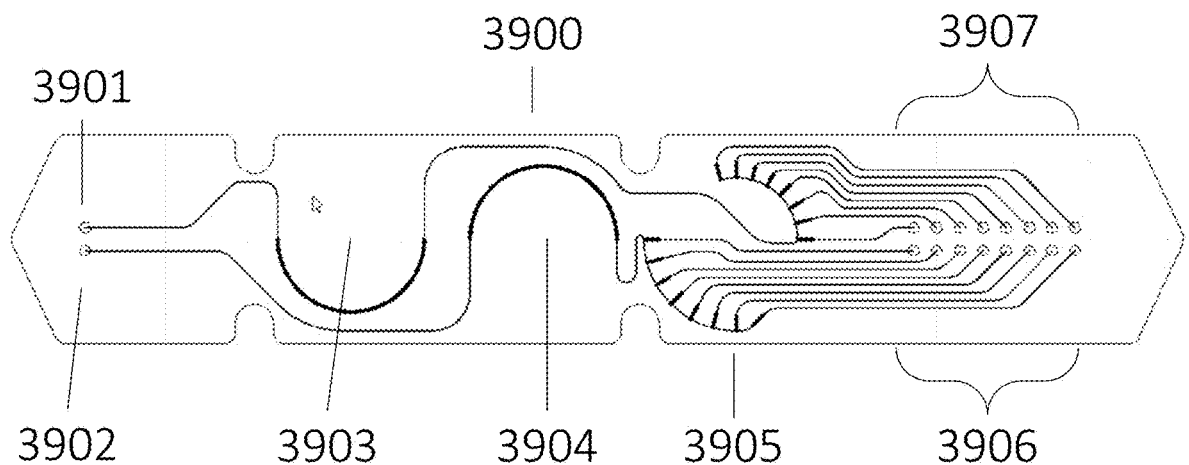
FIG. 39A shows a three-motor valve fluidic that has a pair of ports for connecting to the shared, central reservoir shown in FIG. 38 with separate delivery and removal pumps according to one embodiment of the present invention.

FIG. 39A shows a three-motor valve fluidic 3900 that has a pair of ports 3901 and 3902 for connecting to the shared, central reservoir in FIG. 38. These ports are connected to a fluid delivery pump 3903 and a fluid removal pump 3904, which in turn are connected to a 2×8 RPV 3905 that can deliver fluid from the central reservoir via port 3901 through the fluid delivery pump 3903 to tubing ports 3907 connected to the input needles of each local organ reservoir. The system can remove fluid from these local organ reservoirs through tubing ports 3906 that are connected to the fluid removal pump 3904, which then sends the fluid removed from the local organ reservoir to the common fluid reservoir via port 3902.

Figure 39B:
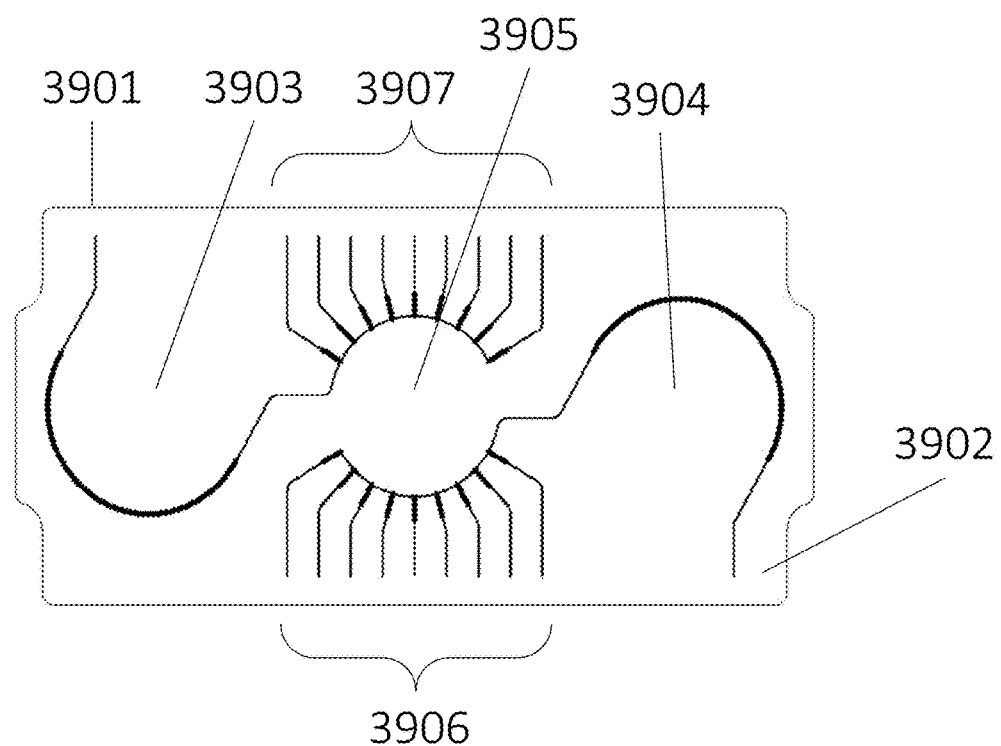
FIG. 39B shows another configuration of the valve according to another embodiment of the present invention.

FIG. 39B shows another configuration of this valve.

Figure 39C:
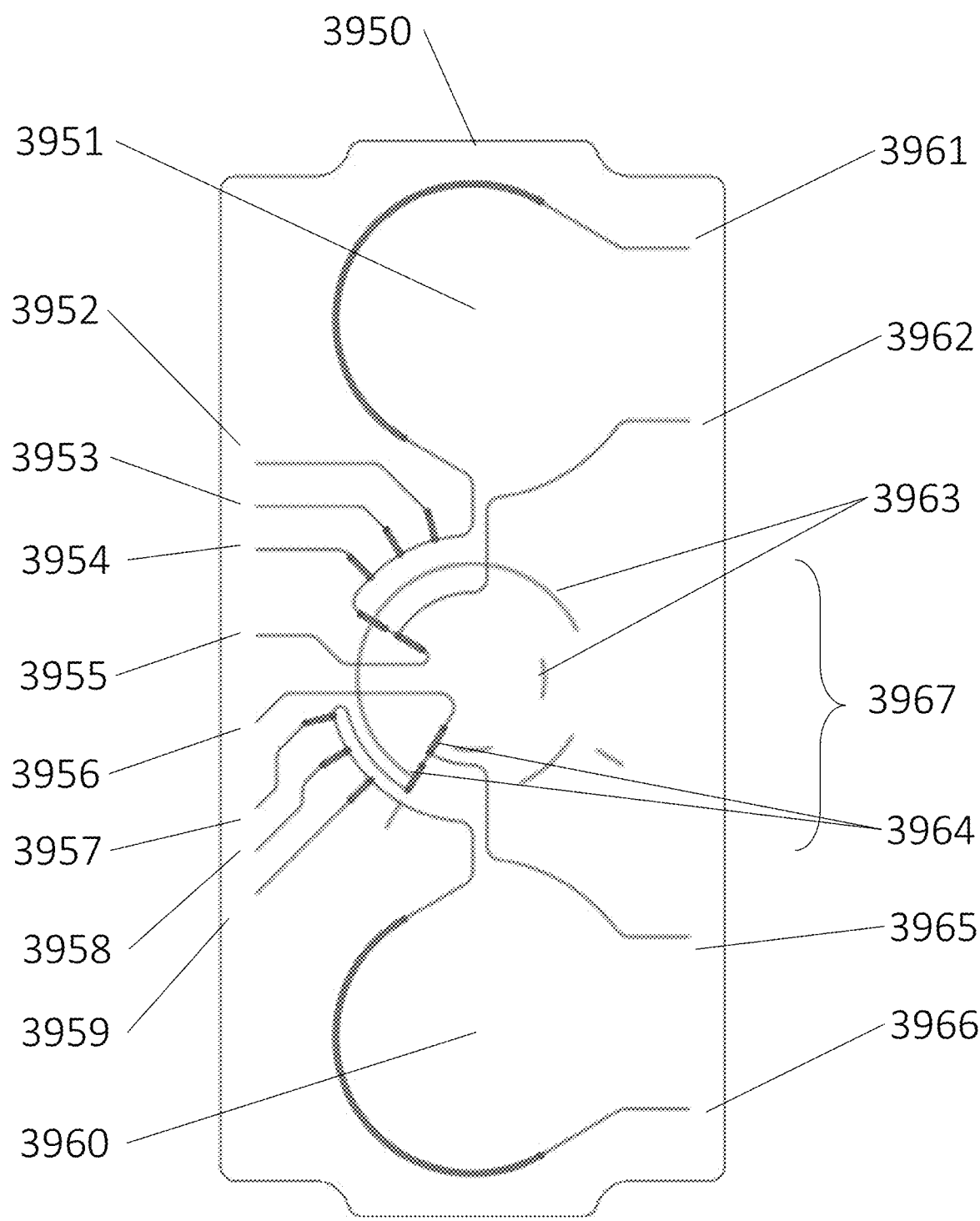
FIG. 39C shows a valve for controlling the recirculation of culture media in a two-sided organ-on-chip, with a separate pump for each side of the organ according to one embodiment of the present invention.

FIG. 39C shows a valve 3950 that can control the recirculation of culture media in a two-sided organ-on-chip, such as a brain-on-a-chip that has both a vascular compartment and a neural compartment separated by the blood-brain-barrier. The pump 3951 is the pump for organ-side 1. Port 3952 is input 1 to side 1, Port 3953 is input 2 to side 1, and port 3954 is input 3 to side 1. Ports 3955 and 3956 are outputs to side 1 and side 2, respectively. Ports 3957, 3958, and 3959 are inputs 1, 2, and 3 for side 2, respectively. The pump for organ side 2 is pump 3960. The fluidic input to organ 1 is port 3961, and the output from that organ is connected to port 3962. The rotary planar valve 3967 centered in this chip has actuation points marked by the short bars. Actuator 3963 is representative of the actuator detents for some common functions of the valve, whereas detents 3964 are required for recirculation. Port 3966 delivers fluid to organ side 2, and this fluid returns to the valve by port 3965.

This valve can support various modes: Inject media, inject drug, inject H$_2$O, recirculate to local reservoir, reverse flow to draw cells into device without going through a pump, and other modes. The valve actuator has four control quadrants that allow fluid to flow to side 1 only, side 2 only, sides 1 and 2, or neither side.

Figure 40A:
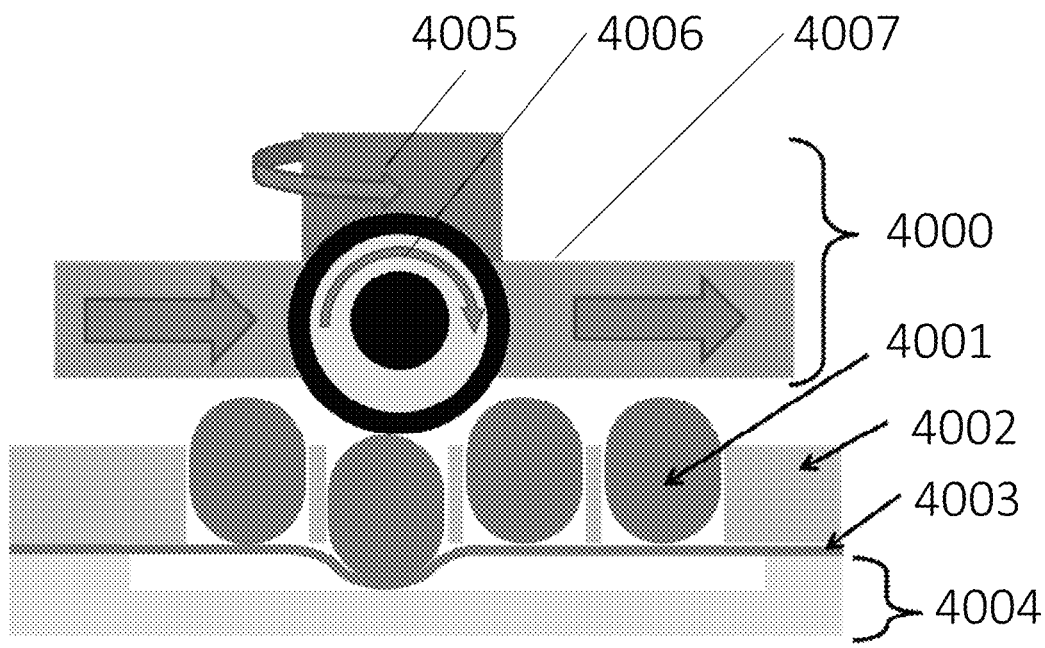
FIG. 40A shows schematically a hybrid rigid-elastomer, pin-driven, rotary planar peristaltic pump according to one embodiment of the present invention.
Figure 40B:
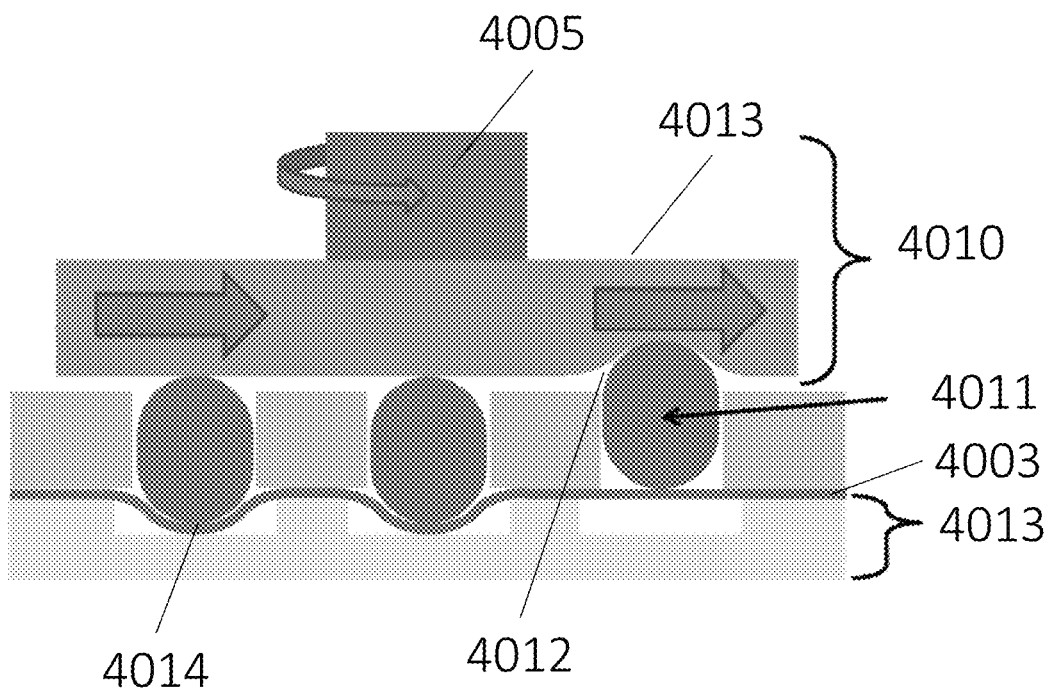
FIG. 40B shows schematically a hybrid rigid-elastomer rotary planar valve according to one embodiment of the present invention.

While each of the pumps and valves discussed so far could be fabricated from PDMS or another elastomer, there are alternative pump and valve geometries that could be used, for example the hybrid rigid-elastomer approach shown in FIG. 40. The pin-driven, peristaltic pump in FIG. 40A has a motor whose shaft 4005 rotates a pump actuator 4007 that drives a peristaltic pump roller 4006. This pump roller drive head 4000 sequentially depresses a multiplicity of actuator pins 4001. These pins sequentially depress an elastomer membrane 4003 that then leads to peristaltic pumping in the microfluidic channel 4004. The same principle can be applied to the rotary planar valve in FIG. 40B. The motor shaft 4005 rotates a valve actuator head 4010 that includes an actuator disk 4013 with detents 4012. When an actuator pin 4011 is pushed upward into the detent by the elastic compliance of the membrane 4003, the channel in the fluidic network 4013 beneath is then opened. Otherwise, the pins seal the channels, as in 4014.

The pins could be replaced with spherical balls or flexible levers. The advantage of the pumps and valves in FIGS. 40A and 40B is that the body of the valves can be fabricated from a hard thermoplastic, such as in cyclic olefin copolymer (COC), and have a minimal amount of elastomer.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

[1]. Prokop, A, Prokop, Z, Schaffer, D, Kozlov, E, Wikswo, J P, Cliffel, D, Baudenbacher, F. NanoLiterBioReactor: Long-Term Mammalian Cell Culture at Nanofabricated Scale, Biomed. Microdevices, 6, 325-339, 2004.

[2]. Werdich, A, Lima, E A, Ivanov, B, Ges, I, Wikswo, J P, Baudenbacher, F J. A Microfluidic Device to Confine a Single Cardiac Myocyte in a Sub-Nanoliter Volume on Planar Microelectrodes for Extracellular Potential Recordings, Lab Chip, 4, 357-362, 2004.

[3]. Wikswo, J P, Prokop, A, Baudenbacher, F, Cliffel, D, Csukas, B, Velkovsky, M. Engineering Challenges of BioNEMS: the Integration of Microfluidics, and Micro- and Nanodevices, Models, and External Control for Systems Biology, IEE Proc.-Nanobiotechnol., 153, 81-101, 2006.

[4]. LeDuc, P R, Messner, W C, Wikswo, J P. How Do Control-Based Approaches Enter into Biology?, Annu. Rev. Biomed. Engr., 13, 369-396, 2011.

[5]. Byrd, T F, Hoang, L T, Kim, E G, Pfister, M E, Werner, E M, Arndt, S E, Chamberlain, J W, Hughey, J J, Nguyen, B A, Schneibel, E J, Wertz, L L, Whitfield, J S, Wikswo, J P, Seale, K T. The Microfluidic Multitrap Nanophysiometer for Hematologic Cancer Cell Characterization Reveals Temporal Sensitivity of the Calcein-AM Efflux Assay, Sci. Rep., 4, Article 5117, 2014. PMCID: PMC4038811.

[6]. McKenzie, J R, Cognata, A C, Davis, A N, Wikswo, J P. Real-Time Monitoring of Cellular Bioenergetics With a Multianalyte Screen-Printed Electrode, Anal. Chem., 87, 7857-7864, 2015.

[7]. Darby, S, Moore, M, Wikswo, J P, Reiserer, R, Friedlander, T, Schaffer, D K, Seale, K T. A Metering Rotary Nanopump for Microfluidic Systems, Lab Chip, 10, 3218-3226, 2010. PMCID: PMC4156019.

[8]. Gould, P A, Hoang, L T, Scherrer, J R, Matloff, W J, Seale, K T, Curtis, E L, Schaffer, D K, Hall, D J, Kole, A, Reiserer, R S, Tidwell, H, Samson, P C, Wikswo, J P, Peristaltic Micropump and Related Systems and Methods, Pat. App. No. PCT/US2011/055432, filed Oct. 7, 2011.

[9]. Baudenbacher, F J, Wikswo, J P, Balcarcel, R R, Cliffel, D, Eklund, S, Gilligan, J M, McGuinness, O, Monroe, T, Prokop, A, Stremler, M A, Werdich, A A, Apparatus and Methods for Monitoring the Status of a Metabolically Active Cell, U.S. Pat. No. 7,704,745 B2, Apr. 27, 2010

[10]. Cliffel, D, Baudenbacher, F J, Wikswo, J P, Eklund, S, Balcarcel, R R, Gilligan, J M, Device and Methods for Detecting the Response of a Plurality of Cells to at Least One Analyte of Interest, U.S. Pat. No. 7,713,733 B2, May 11, 2010.

[11]. Block III, F E, Samson, P C, Wikswo, J P, Normally Closed Microvalve and Applications of the Same, Pat. App. No. PCT/US2013/071324, filed Nov. 21, 2013.

[12]. Wikswo, J P, Block III, F E, Samson, P C, Method for Sterile Fluidic Interconnection of Multiple Perfused Engineered Tissue Constructs and Microbioreactors, Pat. App. No. 61/932,841 (US Provisional), filed Jan. 30, 2014.

[13]. Seale, K T, Wikswo, J P, Schaffer, D, Reiserer, R S, Darby, S, Metering Rotary Nanopump, Method of Fabricating Same, and Applications of Same, Pat. App. No. US 20120015428 A1.

[14]. Wikswo, J P, Markov, D, McCawley, L J, McLean, J A, Cliffel, D, Reiserer, R S, Samson, P C, Perfusion Controller, Microclinical Analyzer and Applications of the Same, U.S. Provisional Patent App. No. 61/569,145, filed Dec. 9, 2011.

[15]. Wikswo, J P, Cliffel, D E, Markov, D A, McLean, J A, McCawley, L J, Samson, P C, Reiserer, R S, Block, F E, McKenzie, J R, Integrated Organ-on-Chip System and Applications of the Same, Pat. App. No. PCT/US2012/068771, filed Nov. 20, 2013.

[16]. Wikswo, J P, Samson, P C, Block III, F E, Reiserer, R S, Parker, K K, McLean, J A, McCawley, L J, Markov, D, Levner, D, Ingber, D E, Hamilton, G A, Goss, J A, Cunningham, R, Cliffel, D E, McKenzie, J R, Bahinski, A, Hinojosa, C D, Integrated Human Organ-on-Chip Microphysiological Systems, Pat. App. No. PCT/US2012/068725, filed Dec. 10, 2012.

[17]. Hansen, Carl L., Microfluidic technologies for structural biology, Ph.D. Dissertation, Caltech, May 28, 2004.

[18]. Hansen, C L, Classen, S, Berger, J M, Quake, S R. A Microfluidic Device for Kinetic Optimization of Protein Crystallization and In Situ Structure Determination, J. Am. Chem. Soc., 128, 3142-3143, 2006.

[19]. Diercks, A H, Ozinsky, A, Hansen, C L, Spotts, J M, Rodriguez, D J, Aderem, A. A Microfluidic Device for Multiplexed Protein Detection in Nano-Liter Volumes, Anal. Biochem., 386, 30-35, 2009.

What is claimed is:

1. An integrated bio-object microfluidics module, the bio-object including an organ, a group of cells, or tissues, comprising:

an input bus, and an output bus, being connectable to an interface that allows the integrated bio-object microfluidics module to be connected to another integrated bio-object microfluidics module, or other microfluidic module of a similar design;

an upstream interconnection bus control valve fluidic coupled to the input bus, and a downstream interconnection bus control valve fluidic coupled to the output bus;

an arterial bus line, a venous bus line, a wash bus line, and a waste bus line, each fluidically connecting between the upstream interconnection bus control valve and the downstream interconnection bus control valve;

an input control valve fluidically connecting to the arterial bus line, the upstream interconnection bus control valve, the bio-object and a plurality of inlets, and an output control valve fluidically connecting to the bio-object, the input control valve, the downstream interconnection bus control valve and a plurality of outlets;

a pump fluidically connecting between the input control valve and the bio-object;

wherein the plurality of inlets is adapted for providing a plurality of fluids, and the plurality of outlets is adapted for collecting waste and sample for analysis; and wherein each of the input control valve, the output control valve, the upstream interconnection bus control valve and the downstream interconnection bus control valve comprises a plurality of control ports, each control port being individually controllable in an open state in which a flow of fluid is allowed or a closed state in which a flow of fluid is occluded, such that the integrated bio-object microfluidics module is selectively operable in one of a Run Isolated Mode, a Run Interconnected Mode, and a Sterilize/Wash mode.

2. The integrated bio-object microfluidics module of claim 1, wherein each of the input control valve, the output control valve, the upstream interconnection bus control valve and the downstream interconnection bus control valve comprises a multiport, rotary planar valve.

3. The integrated bio-object microfluidics module of claim 1, wherein each of the upstream interconnection bus control valve and the downstream interconnection bus control valve comprises a plurality of toggle valves.

4. The integrated bio-object microfluidics module of claim 3, wherein each toggle valve comprises a compression actuator, and a handle engaged with the compression actuator for controlling the compression actuator to operably compress a microfluidic channel underneath.

5. The integrated bio-object microfluidics module of claim 3, wherein each toggle valve is a double-pole, single-throw opposite toggle valve comprising a foreground compression actuator, a background compression actuator, and a handle engaged with the foreground compression actuator and the background compression actuator for controlling them to compress a foreground microfluidic channel and a background microfluidic channel, respectively.

6. The integrated bio-object microfluidics module of claim 3, wherein each toggle valve comprises a body defining a central axle hole, two ball detents, a compression actuator and a handle respectively extending from the body such that the actuator and the handle are angled, wherein the body is rotatable into one of two states controlled by the two ball detents so as to actuate the compression actuator to occlude the microfluidic channel underneath.

7. The integrated bio-object microfluidics module of claim 1, further comprising a microcontroller for individually controlling each port of the input control valve, the output control valve, the upstream interconnection bus control valve and the downstream interconnection bus control valve.

8. The integrated bio-object microfluidics module of claim 7, wherein the microcontroller is provided with a wireless communication protocol.

9. An interconnect system usable for fluidically connecting a first microfluidics module to a second microfluidics module, comprising:
- a first interface and a second interface for the first microfluidics module and the second microfluidics module, respectively, each interface comprising:
  - a first surface, an opposite, second surface, and a body defined therebetween; and
  - connection busses defined through the body, the connection busses being fluidically connecting to a wash bus line, an arterial bus line, a venous bus line, and a waste bus line of a respective microfluidics module through interface tubing ports on the first surface of each interface, such that when connected, the wash bus line, the arterial bus line, the venous bus line, and the waste bus line of the first microfluidics module are fluidically connected to those of the second microfluidics module, respectively, through the connection busses on the second surface of the first and second interfaces; and
  - an alignment pin and an alignment hole spatially formed on the second surface of each interface such that when connected, the alignment pin of the first interface fits into the alignment hole of the second interface, and vice versa; and
- a rotatable port cover disposed between the first interface and the second interface, retractably attached to an end portion of one of the first interface and the second interface, and operably rotating between a close position and an open position along a rotation direction parallel to the second surface of said one of the first interface and the second interface, such that when in the close position, the rotatable port cover seals the connection busses of at least said one of the first interface and the second interface for preventing leakage and contamination of fluid and/or introduction of air bubbles for at least one of the first microfluidics module and the second microfluidics module when the first microfluidics module and the second microfluidics are not connected to each other, and when in the open position, the rotatable port cover retracts so that edges of the first microfluidics module and the second microfluidics module are not obstructed by the rotatable port cover.

10. The interconnect system of claim 9, wherein each interface comprises a pair of magnets formed on the second surface for facilitating alignment and attachment of the first and second interfaces.

11. The interconnect system of claim 9, wherein the connection busses on the second surface of each interface are configured such that the waste line of the first microfluidics module is occluded by a flow stopping peg, and/or the wash line of the second microfluidics module is occluded by a rubber stopper.

12. The interconnect system of claim 9, wherein the arterial bus line and the venous line of one of the first and second microfluidics modules are fluidically connectable via internal tubing or selectively occluded.

13. A microfluidics module tray, comprising:
- a plurality of microfluidics modules arranged in an array; and
- a plurality of interfaces, each interface being recited as claim 9,
- wherein each two adjacent microfluidics modules are interconnected by respective two interfaces.

14. The microfluidics module tray of claim 13, wherein the plurality of microfluidics modules comprises at least one integrated bio-object microfluidics module.

15. The interconnect system of claim 9, wherein the alignment pin is adapted to provide electrical power for driving on-module pumps, valves, or electronics of the first microfluidics module and/or the second microfluidics module.

16. The interconnect system of claim 9, wherein the rotatable port cover comprises:
- a cover cam with a cam groove rotatably attached to said end portion of said one of the first interface and the second interface; and
- a cam ridge formed at an end portion of the rotatable cover, the cam ridge being complementally engaged with the cam groove of the cover cam such that the rotatable cover is operably rotatable around the cover cam.

17. The interconnect system of claim 10, wherein the rotatable port cover comprises a magnet separator.

* * * * *